(12) United States Patent
Burkly et al.

(10) Patent No.: US 6,770,745 B2
(45) Date of Patent: Aug. 3, 2004

(54) COMMON GAMMA CHAIN BLOCKING AGENTS

(75) Inventors: Linda C. Burkly, West Newton, MA (US); Christopher D. Benjamin, Beverly, MA (US); Catherine Hession, Hingham, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 09/824,286

(22) Filed: Apr. 2, 2001

(65) Prior Publication Data

US 2002/0028202 A1 Mar. 7, 2002

Related U.S. Application Data

(63) Continuation of application No. 09/189,129, filed on Nov. 10, 1998, now Pat. No. 6,323,027, which is a continuation of application No. PCT/US97/07870, filed on May 9, 1997, which is a continuation-in-part of application No. 60/017,466, filed on May 10, 1996.

(51) Int. Cl.$^7$ ................................................ C07K 16/28
(52) U.S. Cl. .................................. 530/388.22; 435/344
(58) Field of Search .................. 530/388.22, 387.3, 530/387.9, 388.1, 388.15; 536/23.5

(56) References Cited

U.S. PATENT DOCUMENTS

| 5,510,259 A | 4/1996 | Sugamura et al. |
| 5,582,826 A | 12/1996 | Shinamura et al. |

FOREIGN PATENT DOCUMENTS

| EP | 0 125 023 A1 | * 11/1984 |
| EP | 0 578 932 A2 | 4/1993 |
| EP | 0 621 338 A2 | * 10/1994 |
| WO | WO 92/18534 | 4/1991 |
| WO | WO 9218534 A1 | * 10/1992 |
| WO | WO 93/16723 | 9/1993 |
| WO | WO 96/12733 | 10/1995 |

OTHER PUBLICATIONS

Hudson et al, Accession No. M83538, Sequence database genbank110, embl157, Jan. 10, 1992 (see attached sequence alignment).*

He, et al. "Blockade of T– and B–Lymphocyte Development by Antibody to the Gamma c Subunit of the Receptors for Interleukins 2, 4 and 7." Proc. Natl. Acad. Sci., USA, Jun. 1995, vol. 92; 5689–5693.

He, et al. "Expression and Function of the Gamma c Subunit of the IL–2, IL–4, and IL–7 Receptors: Distinct Interaction of Gamma c in the IL–4 Receptor." The American Assoc. of Immunologists, 1995, 1596–1605.

Jones, et al. "Replacing the Complementarity–Determining Regions in a Human Antibody with those from a Mouse." Nature, vol. 321, May 1986, 522–525.

Jones, P.T. "Immunological Techniques in Biochemical Research." Biochemical Society Transactions, 1992, vol. 20, 203–207.

Kondo, et al. "Functional Participation of the IL–2 Receptor Gamma Chain in IL–7 Receptor Complexes." Science, vol. 263, Mar. 1994, 1453–1454.

Kondo et al. "Sharing the Interleukin–2 (IL–2) Receptor Gamma Chain Between Receptors for IL–2 and IL–4." Science, vol. 263, Dec. 1993, 1874–1877.

Marks, et al. "Molecular Evolution of Proteins on Filamentous Phage." Journal of Biological Chemistry, vol. 267, No. 23, Aug. 1992, 16007–16010.

Mylvaganam, et al. "Structural Basis for the Binding of an Anti–Cytochrome c Antibody to its Antigen: Crystal Structures of FabE8–Cytochrome c Complex to 1.8 A Resolution and FabE8 to 2.26 A Resolution." Article No. mb981942, J. Mol. Biol. (1998) 281, 301–322.

Riechmann, et al. "Reshaping Human Antibodies for Therapy." Nature, vol. 332, Mar. 1998, 323–327.

Takeshita, et al. "Cloning of the Gamma Chain of the Human IL–2 Receptor." Science, vol. 257, Jul. 1992, 379–382.

* cited by examiner

Primary Examiner—Lorraine Spector
Assistant Examiner—Eileen O'Hara
(74) Attorney, Agent, or Firm—Biogen Idec MA Inc.

(57) ABSTRACT

The invention relates to antibodies which specifically bind to the gc chain of cytokine receptors, as well as to cell lines which produce such antibodies, pharmaceutical compositions, and methods of treating immunological diseases by treating patients with such antibodies.

1 Claim, 14 Drawing Sheets

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 1446 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vii) IMMEDIATE SOURCE:
      (B) CLONE: pLB001

(xi) SEQUENCE DESCRIPTION: SEQ ID NO: 1:

```
ATGGTGAAGC CATCATTACC ATTCACATCC CTCTTATTCC TGCAGCTGCC CCTGCTGGGA      60

GTGGGGCTGA ACACGACAAT TCTGACGCCC AATGGGAATG AAGACACCAC AGCTGATTTC     120

TTCCTGACCA CTATGCCCAC TGACTCCCTC AGTGTTTCCA CTCTGCCCCT CCCAGAGGTT     180

CAGTGTTTTG TGTTCAATGT CGAGTACATG AATTGCACTT GGAACAGCAG CTCTGAGCCC     240

CAGCCTACCA ACCTCACTCT GCATTATTGG TACAAGAACT CGGATAATGA TAAAGTCCAG     300

AAGTGCAGCC ACTATCTATT CTCTGAAGAA ATCACTTCTG GCTGTCAGTT GCAAAAAAAG     360

GAGATCCACC TCTACCAAAC ATTTGTTGTT CAGCTCCAGG ACCCACGGGA ACCCAGGAGA     420

CAGGCCACAC AGATGCTAAA ACTGCAGAAT CTGGTGATCC CCTGGGCTCC AGAGAACCTA     480

ACACTTCACA AACTGAGTGA ATCCCAGCTA GAACTGAACT GGAACAACAG ATTCTTGAAC     540

CACTGTTTGG AGCACTTGGT GCAGTACCGG ACTGACTGGG ACCACAGCTG GACTGAACAA     600

TCAGTGGATT ATAGACATAA GTTCTCCTTG CCTAGTGTGG ATGGGCAGAA ACGCTACATG     660

TTTCGTGTTC GGAGCCGCTT TAACCCACTC TGTGGAAGTG CTCAGCATTG GAGTGAATGG     720
```

```
AGCCACCCAA TCCACTGGGG GAGCAATACT TCAAAAGAGA ATGTCGACAA AACTCACACA      780

TGCCCACCGT GCCCAGCACC TGAACTCCTG GGGGGACCGT CAGTCTTCCT CTTCCCCCCA      840

AAACCCAAGG ACACCCTCAT GATCTCCCGG ACCCCTGAGG TCACATGCGT GGTGGTGGAC      900

GTGAGCCACG AAGACCCTGA GGTCAAGTTC AACTGGTACG TGGACGGCGT GGAGGTGCAT      960

AATGCCAAGA CAAAGCCGCG GGAGGAGCAG TACAACAGCA CGTACCGTGT GGTCAGCGTC     1020

CTCACCGTCC TGCACCAGGA CTGGCTGAAT GGCAAGGAGT ACAAGTGCAA GGTCTCCAAC     1080

AAAGCCCTCC CAGCCCCCAT CGAGAAAACC ATCTCCAAAG CCAAAGGGCA GCCCCGAGAA     1140

CCACAGGTGT ACACCCTGCC CCCATCCCGG GATGAGCTGA CCAAGAACCA GGTCAGCCTG     1200

ACCTGCCTGG TCAAAGGCTT CTATCCCAGC GACATCGCCG TGGAGTGGGA GAGCAATGGG     1260

CAGCCGGAGA ACAACTACAA GACCACGCCT CCCGTGTTGG ACTCCGACGG CTCCTTCTTC     1320

CTCTACAGCA AGCTCACCGT GGACAAGAGC AGGTGGCAGC AGGGGAACGT CTTCTCATGC     1380

TCCGTGATGC ATGAGGCTCT GCACAACCAC TACACGCAGA AGAGCCTCTC CCTGTCTCCG     1440

GGTAAA                                                               1446
```

(2) INFORMATION FOR SEQ ID NO: 2:

(i) SEQUENCE CHARACTERISTICS:
        (A) LENGTH: 482 amino acids
        (B) TYPE: amino acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 2:

```
Met Val Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro As  Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
            85                  90                  95

Asp Lys Val Gln Lys Cys Ser His Tyr Leu Phe Ser Glu Glu Ile Thr
        100                 105                 110

Ser Gly Cys Gln Leu Gln Lys Lys Glu Ile His Leu Tyr Gln Thr Phe
    115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
            165                 170                 175

Arg Phe Leu Asn His Cys Leu Glu His Leu Val Gln Tyr Arg Thr Asp
        180                 185                 190
```

```
Trp Asp His Ser Trp Thr Glu Gln Ser Val Asp Tyr Arg His Lys Phe
        195                 200                 205

Ser Leu Pro Ser Val Asp Gly Gln Lys Arg Tyr Met Phe Arg Val Arg
        210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Val Asp
                    245                 250                 255

Lys Thr His Thr Cys Pro Pro Cys Pro Ala Pro Glu Leu Leu Gly Gly
                260                 265                 270

Pro Ser Val Phe Leu Phe Pro Pro Lys Pro Lys Asp Thr Leu Met Ile
                275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
                340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
        370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
                435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys (2) INFORMATION FOR SEQ ID NO: 3:

(i) SEQUENCE CHARACTERISTICS:
        (A) LENGTH: 112 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (xi) SEQUENCE DESCRIPTION: SEQ ID NO: 3:

Leu Gln Glu Ser Gly Pro Gly Leu Val Ala Pro Ser Gln Ser Leu Ser
1               5                   10                  15

Ile Thr Cys Thr Val Ser Gly Phe Ser Leu Thr Ser Tyr Gly Val His
                20                  25                  30

Trp Val Arg Gln Pro Pro Gly Lys Gly Leu Glu Trp Leu Gly Val Ile
```

```
            35                  40                  45
Trp Ala Gly Gly Ser Thr Asn Tyr Asn Ser Ala Leu Met Ser Arg Leu
    50                  55                  60

Asn Ile Asn Arg Asp Asn Ser Lys Ser Gln Ile Phe Leu Lys Met Asn
65                  70                  75                  80

Ser Leu Gln Thr Asp Asp Thr Ala Ile Tyr Tyr Cys Ala Arg Glu Gly
                85                  90                  95

Ser Thr Val Asp Ser Met Asp Tyr Trp Gly Gln Gly Thr Thr Val Thr
                100                 105                 110
```

(2) INFORMATION FOR SEQ ID NO: 4:

(i) SEQUENCE CHARACTERISTICS:
        (A) LENGTH: 106 amino acids
        (B) TYPE: amino acid
        (C) STRANDEDNESS: not relevant
        (D) TOPOLOGY: linear (ii) MOLECULE TYPE: peptide (v) FRAGMENT TYPE: internal (xi) SEQUENCE DESCRIPTION: SEQ ID NO: 4:

```
Asp Ile Val Met Thr Gln Ser His Lys Phe Met Ser Thr Ser Val Gly
1               5                   10                  15

Asp Ser Ile Thr Ile Thr Cys Lys Ala Ser Gln Asp Val Thr Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ile Thr Pro Trp
                85                  90                  95

Thr Phe Gly Gly Gly Thr Lys Leu Glu Ile
                100                 105
```

(2) INFORMATION FOR SEQ ID NO: 5:

(i) SEQUENCE CHARACTERISTICS:
        (A) LENGTH: 319 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GATATCGTAA TGACCCAGTC TCACAAATTC ATGTCCACAT CAGTAGGAGA CAGTATCACC     60

ATCACCTGCA AGGCCAGTCA GGATGTGACT ACTGCTGTAG CCTGGTATCA ACAAAAACCA    120

GGGCAATCTC CTAAACTTCT GATTTACTGG GCATCCACCC GGCACACTGG AGTCCCTGAT    180

CGCTTCACAG GCAGTGGATC TGGGACAGAT TATACTCTCA CCATCAGCAG TGTGCAGGCT    240

GAAGACCTGG CACTTTATTA CTGTCAGCAA CATTATATCA CTCCGTGGAC GTTCGGTGGA    300

GGGACCAAGC TGGAGATCT                                                 319
```

(2) INFORMATION FOR SEQ ID NO: 6:

(i) SEQUENCE CHARACTERISTICS:

(A) LENGTH: 336 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CTGCAGGAGT CAGGACCTGG CCTGGTGGCG CCCTCACAGA GCCTGTCCAT CACTTGCACT      60

GTCTCTGGGT TTTCATTAAC CAGCTATGGT GTACACTGGG TTCGCCAGCC TCCAGGAAAG     120

GGTCTGGAGT GGCTGGGAGT CATTTGGGCT GGTGGAAGCA CAAATTATAA TTCGGCTCTC     180

ATGTCCAGAC TGAACATCAA CAGAGACAAT TCCAAGAGCC AAATTTTCTT AAAAATGAAC     240

AGTCTGCAAA CTGATGACAC AGCCATCTAC TACTGTGCCA GAGAGGGTTC TACGGTAGAT     300

TCTATGGACT ACTGGGGCCA AGGGACCACG GTCACC                               336

(2) INFORMATION FOR SEQ ID NO: 7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

AACTGCAGCG GCCGCCATGG TGAAGCCATC ATTACC                                36

(2) INFORMATION FOR SEQ ID NO: 8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GACTTTGTCG ACATTCTCTT TTGAAGTATT GC                                    32

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

CTGGATATCG TAATGACCCA GTCTCCA                                          27

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GTTAGATCTC CAGCTTGGTC CC                                                    22

(2) INFORMATION FOR SEQ ID NO: 11:

(i) SEQUENCE CHARACTERISTICS:
        (A) LENGTH: 22 amino acids
        (B) TYPE: amino acid
        (C) STRANDEDNESS: not relevant
        (D) TOPOLOGY: linear (ii) MOLECULE TYPE: peptide (v) FRAGMENT TYPE: internal (xi) SEQUENCE DESCRIPTION: SEQ ID NO: 11:

Ala Gly Gly Thr Ser Met Ala Arg Cys Thr Gly Cys Ala Gly Ser Ala
1               5                   10                  15

Gly Thr Cys Trp Gly Gly
            20

(2) INFORMATION FOR SEQ ID NO: 12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

TGAGGAGACG GTGACCGTGG TCCCTTGGCC CC                                          32

(2) INFORMATION FOR SEQ ID NO: 13:

(i) SEQUENCE CHARACTERISTICS:
        (A) LENGTH: 5 amino acids
        (B) TYPE: amino acid
        (C) STRANDEDNESS: not relevant
        (D) TOPOLOGY: linear (ii) MOLECULE TYPE: peptide (v) FRAGMENT TYPE: internal (xi) SEQUENCE DESCRIPTION: SEQ ID NO: 13:

Phe Asn Val Glu Tyr
1               5

(2) INFORMATION FOR SEQ ID NO: 14:

(i) SEQUENCE CHARACTERISTICS:
        (A) LENGTH: 7 amino acids
        (B) TYPE: amino acid
        (C) STRANDEDNESS: not relevant
        (D) TOPOLOGY: linear (ii) MOLECULE TYPE: peptide (v) FRAGMENT TYPE: internal (xi) SEQUENCE DESCRIPTION: SEQ ID NO: 14:

Lys Glu Ile His Leu Tyr Gln
1               5

(2) INFORMATION FOR SEQ ID NO: 15:

(i) SEQUENCE CHARACTERISTICS:
        (A) LENGTH: 7 amino acids

```
            (B) TYPE: amino acid
            (C) STRANDEDNESS: not relevant
            (D) TOPOLOGY: linear (ii) MOLECULE TYPE: peptide (v) FRAGMENT TYPE: internal (xi) SEQUENCE DESCRIPTION: SEQ ID NO: 15:

Leu Gln Asn Leu Val Ile Pro
1               5

(2) INFORMATION FOR SEQ ID NO: 16:

(i) SEQUENCE CHARACTERISTICS:
            (A) LENGTH: 5 amino acids
            (B) TYPE: amino acid
            (C) STRANDEDNESS: not relevant
            (D) TOPOLOGY: linear (ii) MOLECULE TYPE: peptide (v) FRAGMENT TYPE: internal (xi) SEQUENCE DESCRIPTION: SEQ ID NO: 16:

His Cys Leu Glu His
1               5

(2) INFORMATION FOR SEQ ID NO: 17:

(i) SEQUENCE CHARACTERISTICS:
            (A) LENGTH: 3 amino acids
            (B) TYPE: amino acid
            (C) STRANDEDNESS: not relevant
            (D) TOPOLOGY: linear (ii) MOLECULE TYPE: peptide (v) FRAGMENT TYPE: internal (xi) SEQUENCE DESCRIPTION: SEQ ID NO: 17:

Phe Asn Pro
1
```

COMMON GAMMA CHAIN BLOCKING AGENTS

RELATED APPLICATIONS

This is a continuation of U.S. Ser. No. 09/189,129, filed on Nov. 10, 1998, now issued U.S. Pat. No. 6,323,027B1, which is a continuation of PCT/US97/07870, filed May 9, 1997, which is a continuation-in-part application of U.S. Ser. No. 60/017,466 filed on May 10, 1996.

FIELD OF THE INVENTION

The invention relates to compounds which specifically interfere with the function of the common gamma chain of cytokine receptors and which are able to block cytokine responses. It also relates to cell lines which produce such compounds, compositions comprising such compounds, methods of blocking the effects of cytokines on cells, and methods of treating immunological diseases by treating patients with the compounds.

BACKGROUND OF THE INVENTION

Cytokines are important molecules produced by cells of the immune system. Cellular responses to cytokines are regulated by cell surface receptors, polypeptide chains that individually and/or coordinately bind cytokines and transmit signals that regulate activation of cellular genes. The affinities of these receptors regulate the magnitude of the cellular response, which can impact the pattern and determine the physiologic outcome. Regulation of cytokine responses can therefore determine if a cell is activated, divides, differentiates, becomes tolerant or dies. Regulation of cytokine response can also determine if auto-immune cells are permitted to survive and proliferate.

Each cytokine receptor contains one or more cytokine-specific polypeptide chains. As discussed below, when cytokines bind to their cognate receptors, signals through these multiple cell surface polypeptide chains of cytokine receptors control cell growth, activation and differentiation, and appear to be critical in regulating the generation and maintenance of immune responses (Sugamura et al., *Adv. Immunol.* 59:225–277 (1995)).

Briefly, immune responses are initiated by antigen presenting cells (APC) which display peptide fragments of processed foreign antigen in association with MHC class II molecules on their surfaces to CD4+ helper T lymphocytes (T helper cells or Th cells) which interact with these APC's. The Th cells are activated when they recognize particular epitopes of a foreign antigen displayed on the appropriate APC surface for which the Th cells express a specific T cell receptor (TcR). In addition to the TcR interaction with a peptide/MHC complex, T cells require a second cognate costimulatory signal, usually through a cell surface receptor, for eg. CD28 (Harding, *Nature* 356:607–609 (1992) interacting with ligands for CD28 expressed on APC including B7-1 and B7-2 (Bluestone, *Immunity* 2:555–559 (1995). Productive engagement of these two types of cell surface receptors primes the T cells to make and to respond to one or more cytokines secreted or released by activated cells. A key cytokine is interleukin-2 (IL-2), which stimulates and supports cell division, increasing the number of interacting cell types and hence the magnitude of the immune response.

In addition to regulating the magnitude of immune responses, the pattern of cytokines released at the onset of an immune challenge affects the subsequent choice of which immune effector pathways are activated (Paul and Seder, *Cell* 76:241–251 (1993). These cytokines are released by several cell types involved in initiating the immune response, including APC and CD4+ helper Th cells which interact with the APCs. Activated Th cells secrete cytokines which, together with the APC-derived cytokines, direct their differentiation into one of several types of Th cells. These different types of Th cells are then responsible for activating diverse effector mechanisms including killer T cell activation, B cell antibody production and macrophage activation. The choice between effector mechanisms is mediated largely by which cytokines are produced by the activated Th cells.

Th cells can be divided into three subgroups based on their cytokine secretion patterns (Fitch et al., *Ann. Rev. Immunol.*, 11, pp. 2948 (1993); Mosmann and Sad, *Immunol. Today* 17:138–146 (1996)). These subgroups are called Th0, Th1 and Th2. In humans, the Th1 pattern of cytokine secretion has been generally associated with cellular immunity and resistance to infection with viruses and intracellular parasites. The Th1 cytokines such as IFN γ and IL-2 tend to activate macrophages, natural killer cells and cytotoxic T cells. Other cytokines produced by APCs, such as IL-7 and IL-15, may also participate in the activation of these cytotoxic functions. In addition to their protective functions, Th1 cytokines promote deleterious inflammatory responses such as delayed type hypersensitivity. Pathological Th1 responses are also associated with a number of organ-specific and systemic autoimmune conditions and with chronic inflammatory diseases, and play an important role in cellular rejection of tissue grafts and organ transplants. In contrast, the Th2 pattern of cytokine secretion (IL-4, IL-5, IL-6, IL-9 and IL-10) promotes the fill expansion and maturation of B cells thereby providing humoral protection, for example, against extracellular pathogens (Howard et al., "T cell-derived cytokines and their receptor", *Fundamental Immunology*, 3d ed., Raven Press, New York (1993)). Th2 cytokines such as IL-4 and IL-9 also increase eosinophil and mast cell production. But like Th1 responses, deleterious Th2 responses can lead to pathologic conditions, including IgE antibodies associated with allergic responses, autoimmune antibodies such as those in idiopathic thrombocytopenia, myasthenia gravis, and systemic lupus erythematosus, and anti-graft antibodies.

The pattern and magnitude of cytokine responses can also be used to negatively regulate activated cells. The absence of appropriate cytokine dependent signaling to activated cells (physiologically, an inadequate or temporally discordant signal) usually results in their death. In some circumstances it can lead to a so called tolerant state, also called unresponsiveness or anergy, where cells survive but fail to respond to subsequent stimuli (Schwartz, *Science*, 248, 1349–1356 (1990); Jenkins et al., *J. Immunol.*, 140, 3324–3330 (1988). Thus, inhibition of cytokine signaling to activated cells may represent a physiological means of regulating for eg. autoreactive cells. It also may be therapeutically useful in treating autoimmune and inflammatory diseases.

One way to block cytokine responses is to target the receptor. In the case of IL-2, the receptor is composed of three distinct polypeptide chains: alpha, beta and γ common (hereinafter "gc"). The alpha chain specifically binds to IL-2 but has no capacity to signal the cell which expresses it. The beta chain binds IL-2 poorly ($K_D$=1 micromolar), but with the alpha chain creates a two chain receptor with an affinity that exceeds that of either chain alone. The gc chain binds IL-2 very weakly, if at all, but combines with the alpha and beta chains to create a three chain receptor with very high affinity [10 picomolar] for IL-2 (Sugamura et al., *Adv.*

*Immunol.* 59:225–277(1995)). Other combinations of the IL-2 receptor chains are also possible. For example, on NK cells the beta and gc chains combine to form an IL-2 receptor of intermediate affinity ($K_D$=1 nanomolar).

The gc chain is a cell surface polypeptide component of cytokine receptors and forms part of the receptors for several other interleukins besides IL-2 such as IL-4, 7, 9, and 15. The extracellular region of the gc chain of these IL receptors (IL-R) is composed of 2 FNIII type domains, each comprised of 7 strands connected by loop sequences which are presumed to form intermolecular contacts (see structural model derived for the IL-4/IL-4 chain gc chain complex, Gustchina et al., Proteins: Structure, Function and Genetics 21:140 (1995)), and for the IL-2/IL-2R complex, Bamborough et al., *Structure* 2:839–851(1994)).

In the case of the IL-4 receptor, the gc chain is paired only with a cytokine binding alpha chain; no additional beta chain has been identified to date. The same is true for the IL-7 and IL-9 receptors; each brings its own cytokine binding alpha chain to combine with the gc chain to create a complete cooperating two chain receptor. The receptor for IL-15 is composed of an alpha chain specific for IL-15 together with the beta chain of the IL-2 receptor and the gc chain. The participation of two and sometimes three polypeptide chains in the functional receptor thus adds another layer of complexity to the regulation of the immune response. Since the gc chain is shared by a number cytokine receptors, blocking the function of the gc chain may affect cells that depend on signaling from IL-2, IL-4, IL-7, IL-9 or IL-15.

Several mAbs which block the function of the murine and human gc chains have been described in the literature. Sugamura and colleagues developed a mAb which binds to murine gc chain and which blocks responses to IL-4, IL-7 and IL-9. The mAb needed auxiliary molecules to inhibit IL-2 (i.e. the mAb failed to inhibit IL-2 responses when used alone). See Kondo et al., *Science,* 262, pp.1874–1877(1993); Kondo et al., *Science,* 263, pp.1453–1454; Kimura et al., *International Immunology,* 7, pp.115–120(1994). See also U.S. Pat. No. 5,582,826 (anti-human gc antibody significantly inhibiting cellular IL-2 activity requires an auxiliary antibody).

He et al. (*J. Immunol.,* 154, pp.1596–1605 (1995) reported two mAbs which bind to murine gc chain. When used without auxiliary molecules (i.e., when used alone) one mAb partially blocked IL-4 but failed to block IL-2 or IL-7, and the other mAb partially blocked IL-7 but failed to block IL-4 or IL-2. These results demonstrate that the gc chain is employed in distinct ways by different receptors. This observation indicates that screening for mAbs that bind to gc chain or that block the cellular response to a given cytokine of the group including IL-2, IL-4, IL-7 IL-9 and IL-15, will not necessarily produce mAbs that can block the cellular responses to any of the other cytokines of this group.

Moreover, given the extremely high affinity (10 pM) of this group of cytokine receptors for their respective cytokines, it would be difficult to achieve effective inhibition using a blocking agent of much lower affinity (e.g., 1–100 nanomolar affinity typical of a mAb) that is competing with cytokine for binding to the same receptor, particularly in the presence of high concentrations of cytokine.

There are no mAbs reported in the prior art that bind to gc chain and block cellular responses to IL-2 when used in the absence of auxiliary molecules. Nor has any single mAb been reported which can block cellular responses to any subset of cytokine which includes IL-2. Indeed, all mAb specific for gc chain developed to date require the addition of an auxiliary molecules i.e., a second compound which could act in concert with that agent to inhibit the cellular response to IL-2.

Monoclonal antibodies (mAbs) that block the function of the gc chain and thereby block cellular responses to cytokines which employ the gc chain in their receptors could provide useful agents to treat various Th cell-based immunological conditions. To date, however, such treatment generally has employed immunomodulatory and immunosuppressive agents as well as a number of drugs (eg. gold or penicillamine) with poorly characterized mechanisms. Three general immunosuppressive agents used currently are steroids, cyclosporine and azathioprine. These non-specific agents are generally required chronically and in high doses are associated with significant toxicity, particularly nephrotoxicity and hepatotoxicity, as well as other adverse side effects.

Useful agents of this kind would include those which block cellular responses to any one of the group of cytokines that have the gc chain in their receptors, to selected members of these, or to all members of this group.

SUMMARY OF THE INVENTION

Accordingly, the invention solves the problems discussed above and provides compositions and methods for treating immunological diseases by inhibiting cytokine signaling using gc chain blocking agents. We have found a) mabs specific for gc chain do not require auxiliary molecules to inhibit IL-2 responses and b) anti-human gc mAbs are cross reactive with non-human gc and have clinical efficacy in a non-human animal model of disease. We have also found a method of finding a class of compounds that are noncompetitive inhibitors of cytokines.

To address the problems caused by conventional treatments with non-specific immunosuppressive agents, it is an object of the invention to provide therapeutic agents which limit pathologic antigen-specific responses by providing a means to inhibit T cell responsiveness, to induce Th cell anergy, or to selectively suppress or activate Th1 vs. Th2 responses.

One aspect of the invention is a gc chain blocking agent that is a soluble gc-binding polypeptide, a soluble gc-blocking polypeptide, or a soluble gc mimetic agent. The preferred gc blocking agents of the invention have the unique property of significantly blocking a response of a cell to interleukin-2 (IL-2) without any requirement for a second compound which also affects response of the cell to IL-2. A preferred gc blocking agent is a monoclonal antibody that cross competes with monoclonal antibody CP.B8 produced by hybridoma cell line ATCC No. HB-12107 for binding to gc chain, and also cross competes with Fab, F(ab')$_2$, and Fv fragments and conjugates of CP.B8. Other antibodies of the invention cross compete with monoclonal antibodies CQ.C11, AE.C9 and AK.F12 as well as Fab, F(ab')$_2$, and Fv fragments and conjugates thereof.

The gc blocking agents of the invention are also able to block a response of a cell to a cytokine that is different from IL-2 and preferred blocking agents are also able to block cytokine responses to interleukin-4 (IL-4), IL-7, IL-9 and IL-15.

Preferred gc blocking agents of the invention contain sequences that can bind to at least one of particular epitopic sequences (SEQ ID NOS:13–17) of the gc chain.

The invention further embodies a series of continuous hybridoma cell line selected from the group consisting of ATCC No. HB-12107, ATCC No. HB-12105, ATCC No.

HB-12104 and ATCC No. HB-12106, as well as specific anti human-gc monoclonal antibodies produced by these hybridoma cell lines and compositions of these monoclonal antibodies.

A further aspect of the invention is directed to particular polynucleotides obtainable from anti human-gc monoclonal antibodies. Preferred sequences are selected from the group of sequences consisting of: (a) SEQ ID NOS.: 5 and/or 6; (b) polynucleotides that hybridize to SEQ ID NOS. 5 and/or 6 under standard hybridization conditions and that encode at least part of a polypeptide having the property of significantly blocking a response of a cell to interleukin-2 (IL-2); and © polynucleotides that encode a protein encoded by any of the foregoing polynucleotide sequences.

Other compositions of the invention include a monoclonal antibody having complementary determining regions (CRDs) encoded by polynucleotide sequences selected from the group consisting of: (a) SEQ ID NOS: 5 and/or 6; (b) polynucleotides that hybridize to SEQ ID NOS: 5 an/or 6 under standard hybridization conditions; and polynucleotides that encode a protein encoded by any of the foregoing polynucleotide sequences.

Still other compositions of the invention include a monoclonal antibody having a light chain variable region CDR with an amino acid sequence selected from the group consisting of: (a) amino acids 24 to 34 of SEQ ID NO: 4; amino acids 50 to 56 of SEQ ID NO: 4 and amino acids 89 to 97 of SEQ ID NO:4. Another composition includes a monoclonal antibody having a heavy chain variable region CDR with an amino acid sequence selected from the group consisting of: (a) amino acids 28 to 32 of SEQ ID NO: 3; amino acids 47 to 61 of SEQ ID NO: 3 and amino acids 95 to 104 of SEQ ID NO: 3.

Pharmaceutical compositions of the invention comprise a gc-blocking agent that is selected from the group consisting of a gc-blocking antibody homolog, a soluble gc-binding polypeptide, a soluble gc-blocking polypeptide, and a soluble gc mimetic agent. Preferred pharmaceutical compositions include a monoclonal antibody that specifically binds to an antigenic determinant of the gc chain of cytokine receptors. Particularly preferred compositions include the CP.B8 mAb.

Methods of the invention include a method of raising an antibody against a protein antigen (such as a gc chain antigen) comprising administering an immunogen that is a non-denatured form of the protein antigen. The non-denatured form of a gc chain antigen preferably comprises a fusion molecule that includes at least part of the gc chain fused to at least part of an immunoglobulin constant region. In another method, the non-denatured form of protein antigen (e.g., gc chain) is coadministered with protein a.

A further aspect of the invention is a method for treating or reducing the advancement, severity or effects of an immunological disease in a subject, comprising the step of administering a composition which comprises a gc-blocking agent. The preferred method includes administration of a blocking agent selected from the group consisting of a gc-blocking antibody homolog, a soluble gc-binding polypeptide, a soluble gc-blocking polypeptide, and a soluble gc mimetic agent. Preferred gc blocking antibody homologs include a monoclonal antibody that specifically binds to an antigenic determinant of the gc chain of cytokine receptors. This method may be used to treat a variety of immunological diseases, including myasthenia gravis, IBD, rheumatoid arthritis, lupus, multiple sclerosis, insulin-dependent diabetes, sympathetic ophthalmia, uveitis, allergy, asthma, parasitic disease, graft versus host disease (GVHD), and psoriasis.

Another method of the invention is a method for inducing tolerance in a subject comprising the step of administering a composition which comprises a a gc-blocking agent. Preferred methods of this type administer a blocking agent selected from the group consisting of a gc-blocking antibody homolog, a soluble gc-binding polypeptide, a soluble gc-blocking polypeptide, and a soluble gc mimetic agent.

Another method of the invention is a method for inhibiting cytokine responsiveness in a subject comprising the step of administering a composition which comprises a gc-blocking agent, the preferred agent being selected from the group consisting of a gc-blocking antibody homolog, a soluble gc-binding polypeptide, a soluble gc-blocking polypeptide, and a soluble gc mimetic agent.

Yet another method of the invention is a method for treating or reducing the advancement, severity or effects of an immunological disease in a subject comprising the step of administering a composition which comprises a noncompetitive inhibitor of a cytokine receptor. This noncompetitive inhibitor is preferably a gc blocking agent that blocks either IL-2 or IL4. The method is useful for treating an immunological disease that is refractory to treatment by any competitive inhibitor of a cytokine.

Our discovery of noncompetitive inhibitors of cytokine receptors allows a further method of identifing a compound that non-competitively inhibits functioning of a cytokine receptor, the method comprising demonstrating that the capacity of the compound to inhibit the function is not attenuated by high concentrations of cytokine. Most preferably, the cytokine receptor utilizes gc as one of its receptor components.

Gc blocking agents of the present invention have the singular advantage of not requiring the addition of an auxiliary compound which could act in concert with that agent to inhibit the cellular response to IL-2.

BRIEF DESCRIPTION OF THE DRAWINGS

FIG. 3 is an array of two histograms showing immunofluorescent staining of PHA activated peripheral blood lymphocytes with anti-gc mAbs. The relative cell number is plotted against the mean fluorescence intensity. Data for individual mAbs are plotted as solid lines, and data for the MOPC 21 control Ig is plotted as indicated.

DETAILED DESCRIPTION OF THE INVENTION

Figure 1:
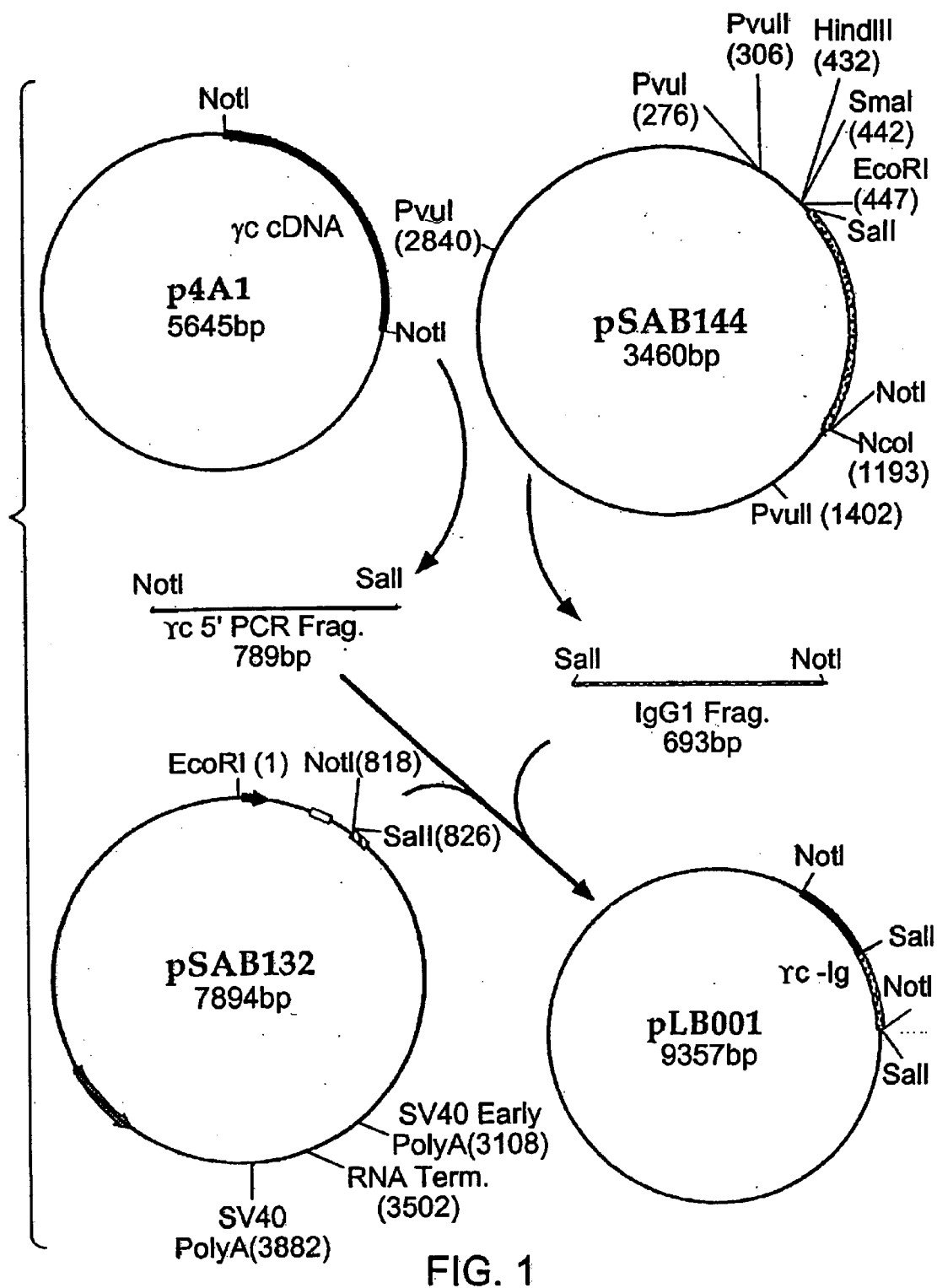
FIG. 1 is a schematic drawing showing the construction of the gc-IgG fusion construct, pLB001, which encodes the amino terminal 254 aa of mature gc chain, ten amino acids of the hinge region of human IgG1, and the CH2 and CH3 constant domains of IgG1.
Figure 2A:
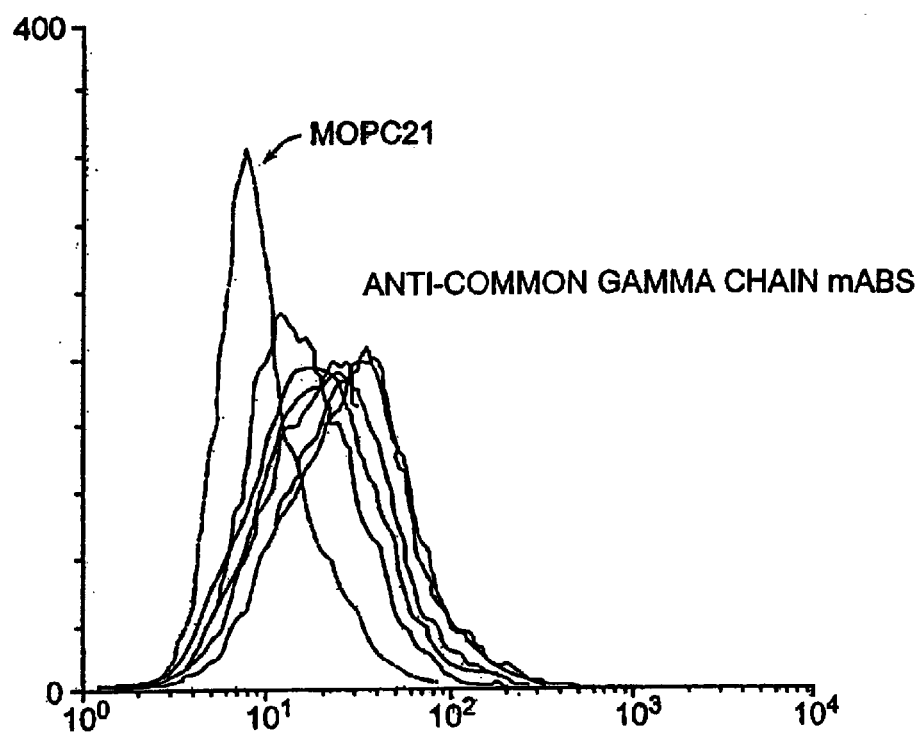
FIG. 2A, is the immunofluorescent staining of L929 gc chain transfectants with different anti-gc mAbs.
Figure 2B:
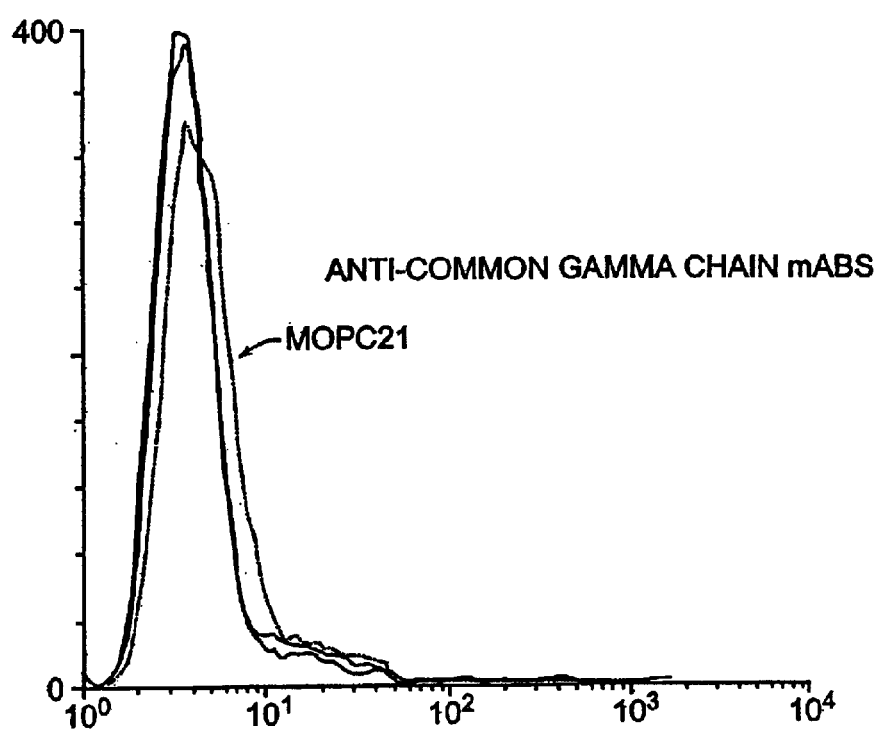
FIG. 2B is the staining of the L929 parent cells by the same antibodies. The remaining figures show staining with different anti-gc mAbs ith L929 gc chain transfectants (FIG. 2C) and staining of L929 parent cells (FIG. 2D).
Figure 2C:
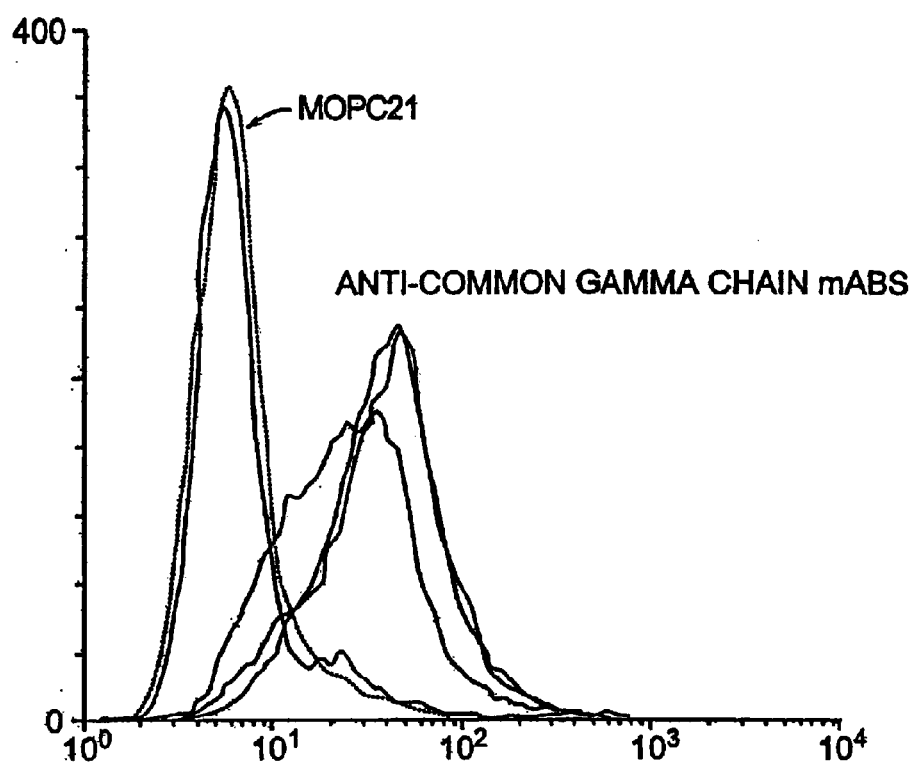
FIG. 2 is an array of four histograms showing immunofluorescent staining with anti-gc mAbs of L929 cells expression human gc chain. The relative cell number is plotted against the mean fluorescence intensity. Data for individual mAbs are plotted as solid lines, and data for the control MOPC21 Ig is plotted as indicated.
Figure 2D:
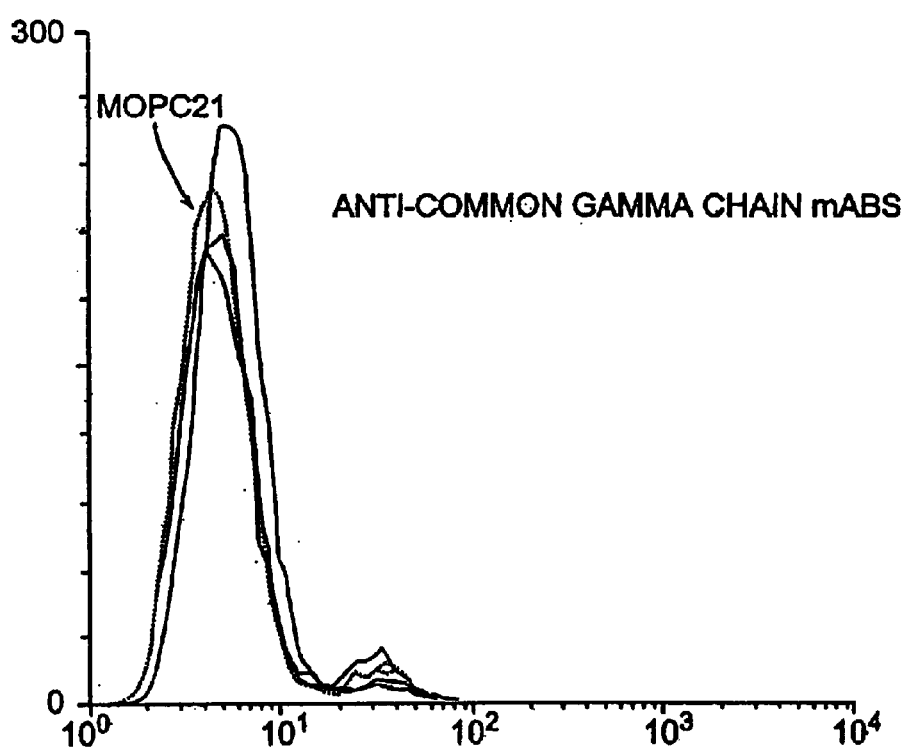

In order that the invention herein described may be fully understood, the following detailed description is set forth.

I. Definitions

The term "cytokine" refers to a molecule which mediates interactions between cells, a "lymphokine" is a cytokine released by lymphocytes.

The term "cytokine-responsive cells" refers to immune and nonimmune cell types which express cytokine receptors. Immune cell types may include but are not limited to T cells of all types, natural killer cells, mast cells, bone marrow stromal cells, monocyotes, B cells and granulocytes such as eosinophils. Nonimmune cells types may include but are not limited to fibroblasts, epithelial cells, endothelial cells, transplanted or grafted cells and tissues.

The term "T helper (Th) cells" refers to a functional subclass of T cells which help to generate cytotoxic T cells and which cooperate with B cells to stimulate antibody production. Helper T cells recognize antigen in association with class II MHC molecules.

The term "Th1" refers to a subclass of T helper cells that produce LTα, IFNγ, IL-2, and other cytokines, and which elicit inflammatory reactions generally associated with a cellular, i.e. non-immunoglobulin, response to a challenge.

"Th1-type cytokines" are those cytokines which elicit inflammatory reactions generally associated with a cellular, non-primarily-immunoglobulin-mediated response to a challenge. These cytokines may be produced by either Th1 cells or by other cells, for example by antigen presenting cells, and may include LTα, IFNγ, IL-2, IL-7, and IL-15.

The term "Th2" refers to a subclass of T helper cells that produce cytokines, including IL-4, IL-5, IL-6, IL-9 and IL-10, which are associated with an immunoglobulin (humoral) response to an immune challenge.

"Th2-type cytokines" are those cytokines which elicit inflammatory reactions generally associated with an immunoglobulin-mediated (humoral) response to a challenge. These cytokines may be produced by either Th2 cells or by other cells, and may include IL-4, IL-5, IL-6, IL-9 and IL-10.

The term "cell mediated" refers to those immunological events that result from the direct effects of T cells and their products to produce a response. This type of response is generally (but not exclusively) associated with the Th1 class of T cells. Not included in this category would be the helper effects of T cells on B cell differentiation and B cell expansion, which are generally associated with the Th2 class of T cells.

The term "delayed type hypersensitivity (DTH)" refers to an immunological response that is characterized by a slow response to an antigen with the full effect manifesting itself over a 1–3 day period. This slow response is in contrast to the relatively fast response seen in an immunoglobulin-mediated (humoral) allergic reaction. There are three types of DTH reactions: contact hypersensitivity, tuberculin-type hypersensitivity and granulomatous reactions.

The terms "immunoglobulin response" or "humoral response" refer to the immunological response of an animal to a foreign antigen whereby the animal produces antibodies to the foreign antigen. The Th2 class of T helper cells are critical to the efficient production of high affinity antibodies.

The term "Fc domain" of an antibody refers to a part of the molecule comprising the hinge, CH2 and CH3 domains, but lacking the antigen binding sites. The term is also meant to include the equivalent regions of an IgM or other antibody isotype.

The term "anti-gc chain antibody" refers to any antibody that specifically binds to at least one epitope or antigenic determinant of the gc chain of cytokine receptors.

The term "gc chain signaling" refers to molecular reactions associated with binding of ligands to gc chain-encompassing cytokine receptors and the subsequent molecular reactions which result therefrom.

The term "cross competes" means that a second antibody binds to the same or a nearby antigenic determinant as a first antibody, and competes for that antigenic determinant when both antibodies are present in a solution and in the presence of the antigen, which can be either free in solution or bound to a cell, matrix or other ligand. "Cross blocking" refers to a situation where when a first, cross competing antibody contacts its antigenic determinant and binds before a second antibody contacts the antigen, it prevents the binding of a second antibody which shares specificity for the same antigenic determinant; likewise, the second antibody blocks binding of the first when the second antibody is allowed to saturate the binding of the antigenic determinant sites before the first antibody contacts the antigen. Cross blocking generally refers to a situation in which there is interference between two mAbs regardless of which was added first. However, two mAbs which bind to the same or nearby antigenic determinants may "cross block" in one direction only: a first mAb may interfere with the binding of a second mAb if the first antibody is added prior to the addition of the second antibody, but the addition of the mAbs in the reverse order does not result in interference. This may occur, for example, if the affinity of one mAb is substantially greater than that of the other mAb for binding to that antigenic determinant. Failure to cross block at all indicates that two mAbs recognize distinct and at least somewhat distant epitopes.

The term "noncompetitive inhibitor" refers to one which blocks the formation of the receptor complex without directly competing against binding of cytokine to the receptor. The characteristic feature is that the degree of inhibition achieved at a given concentration of inhibitor is not attenuated by increasing concentrations of cytokine.

The term "competitive inhibitor" refers to one which blocks the formation of the receptor complex by preventing the binding of cytokine to the receptor. The characteristic feature is that the degree of inhibition achieved at a given concentration of inhibitor is partially or completely overcome by increasing concentrations of cytokine to a high level, a "high concentration" of cytokine is one which exceeds the concentration of cytokine required to stimulate a cellular response that achieves a level one half of that seen at cytokine concentrations sufficient to saturate the given response.

The term "standard hybridization conditions" means salt and temperature conditions substantially equivalent to 0.5 X SSC to about 5 X SSC and 65 degrees C for both hybridization and wash. The term "standard hybridization conditions" as used herein is therefore an operational definition and encompasses a range of hybridization. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulphate, and 100 ug/ml denatured, sonicated salmon sperm DNA at 65 degrees C for 12–20 hours, and washing with 75 mM NaCl/7.5 mM sodium citrate (0.5× SSC)/1% SDS at 65 degrees C. Lower stringency conditions may, for example, include hybridizing with plaque screen buffer, 10% dextran sulphate and 110 ug/ml denatured, sonicated salmon sperm DNA at 55 degrees C for 12–20 hours, and washing with 300 mM NaCl/30 mM sodium citrate (2.0 X SSC)/1% SDS at 55 degrees C. For definitions of high and low stringency, see *Current Protocols in Molecular Biology*, John Wiley & Sons, Inc. New York, Sections 6.3.1–6.3.6, (1989).

The term "expression control sequence" means a sequence of nucleotides that controls and regulates expression of genes when operatively linked to those genes.

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the polynucleotide sequence under the control of the expression control sequence and production of the desired polypeptide encoded by the polynucleotide sequence.

The term "expression vector" means a polynucleotide, most commonly a DNA plasmid, which allows expression of at least one gene when the expression vector is introduced into a host cell. The vector may, or may not, be able to replicate in a cell.

The term "isolated", when applied to polynucleotide sequences, particularly those that encode polypeptides that form at least a portion of a gc blocking agent, means an RNA or DNA polynucleotide, portion of genomic polynucleotide, cDNA or synthetic polynucleotide which, by virtue of its origin or manipulation: (I) is not associated with all of a polynucleotide with which it is associated in nature (e.g., is present in a host cell as a portion of an expression vector); or (ii) is linked to a nucleic acid or other chemical moiety other than that to which it is linked in nature; or (iii) does not occur in nature. By "isolated" it is further meant a polynucleotide sequence: (I) amplified in vitro by, for example, polymerase chain reaction (PCR); (ii) chemically synthesized; (iii) recombinantly produced by cloning; or (iv) purified, as by cleavage and gel separation.

The term "isolated", when applied to polypeptides, particularly those that are at least part of a gc blocking agent, means a polypeptide or a portion thereof which, by virtue of its origin or manipulation: (I) is present in a host cell as the expression product of a portion of an expression vector; or (ii) is linked to a protein or other chemical moiety other than that to which it is linked in nature; or (iii) does not occur in nature. By "isolated" it is further meant a protein that is : (I) chemically synthesized; or (ii) expressed in a host cell and purified away from associated proteins, as by gel chromatography.

A "heterologous promoter" as used herein is a promoter which is not naturally associated with a gene or a purified nucleic acid.

A "purified preparation" or a "substantially pure preparation" of a polypeptide, as used herein, means a polypeptide that has been separated from other proteins, lipids and nucleic acids with which it naturally occurs. Preferably, the polypeptide is also separated from substances such as antibodies or gel matrices (polyacrylamide) which are used to purify it. It is preferred that a polypeptide constitute at least 10% dry weight of the purified preparation, although it may constitute higher percentages e.g., 20, 50, 70, 80 or 95%. The purified preparation also preferably contains sufficient polypeptide to allow protein sequencing. This weight may vary over a wide range, i.e., from 1 microgram to 100 milligram of the polypeptide.

A "substantially pure nucleic acid" (e.g., a substantially pure DNA or RNA) is a nucleic acid which is not immediately contiguous with one or both of the coding sequences with which it is normally contiguous in the naturally occurring genome of the organism from which the nucleic acid is derived. The term includes, for instance, recombinant DNA which is incorporated into a vector such as an autonomously replicating plasmid or virus, or into the genomic DNA of a procaryote or eukaryote or which exists as a separate molecule such as cDNA or genomic DNA fragment produced by polymerase chain reaction PCR or restriction endonuclease treatment independent of other DNA sequences. Substantially pure DNA also includes a recombinant DNA which is part of a hybrid gene encoding additional sequences.

"Homologous" as used herein, refers to the sequence similarity between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are homologous in that position. The percentage homology between two sequences is a function of the number of matching or homologous position shared by the two sequences divided by the number of positions compared×100. For instance, if 6 of 10 of the positions in two sequences are matched or homologous, then the two sequences are 60% homologous. By way of example, the DNA sequences ATTGCC and TATGGC share 50% homology (3 of the 6 total positions are matched). Generally, a comparison is made when two sequences are aligned to give maximum homology.

The terms "peptide", "proteins" and "polypeptides" are used interchangeably herein.

A "purified preparation of cells" refers to an in vitro preparation of cells and not an entire intact plant or animal. In the case of cultured cells or microbial cells, it consists of a preparation of at least 10% and preferably 50% of the subject cells.

A molecule or method of the invention has "biological utility" if it has at least one of the following properties: a) it is able to inhibit the cellular response to IL-2 without the need for an auxiliary agent which also affects the cellular response to IL-2; b) it cross-competes with the CP.B8 mAb or with is Fab', Fab or Fv fragments; c) it provides a means to inhibit responsiveness to one or more cytokines employing gc chain, in addition to IL-2; d) it provides a means to act as a noncompetitive inhibitor of cytokine-induced cellular responses; or e) it reduces the advancement, severity or effects of an immunological disease in a mammal, a blocking agent has biological utility if it is an antagonist, or agonist of a polypeptide having one of the above-listed properties.

The term "nucleic acid" as used herein can include fragments and equivalents. The term "equivalent" refers to nucleotide sequences encoding functionally equivalent molecules to the gc binding agents. Equivalent nucleotide sequences include sequences that differ by one or more nucleotide substitutions, additions, or deletions such as allelic variants and will therefore include sequences that differ from the nucleotide sequences as shown, for example in SEQ ID NOS.: 5 and/or 6 due to the degeneracy of the genetic code. See Section C and G.

Practice of the present invention will employ, unless otherwise indicated, conventional techniques of cell biology, cell culture, molecular biology, transgenic biology, microbiology, recombinant DNA and immunology, which are within the skill of the art. Such techniques are described in the literature. See, for example, *Molecular Cloning: a Laboratory Manual,* 2nd edition. (Sambrook, Fritsch and Maniatis, eds.), Cold Spring Harbor Laboratory Press, 1989; *DNA Cloning*, Volumes I and II (D. N. Glover, ed), 1985; *Oligonucleotide Synthesis*, (M. J. Gait, ed.), 1984; U.S. Pat. No. 4,683,195 (Mullis et al.,); *Nucleic Acid Hybridization* (B. D. Hames and S. J. Higgins, eds.), 1984; Transcription and Translation (B. D. Hames and S. J. Higgins, eds.), 1984; *Culture of Animal Cells* (R. I. Freshney, ed). Alan R. Liss, Inc., 1987; *Immobilized Cells and Enzymes*, IRL Press, 1986; *a Practical Guide to Molecular Cloning* (B. Perbal), 1984; *Methods in Enzymology*, Volumes 154 and 155 (Wu et al., eds), Academic Press, New York; *Gene Transfer Vectors for Mammalian Cells* (J. H. Miller and M. P. Calos, eds.), 1987, Cold Spring Harbor Laboratory; *Immunochemical Methods in Cell and Molecular Biology* (Mayer and Walker, eds.), Academic Press, London, 1987; *Handbook of Experiment Immunology*, Volumes I–IV (D. M. Weir and C. C. Blackwell, eds.), 1986; *Manipulating the Mouse Embryo*, Cold Spring Harbor Laboratory Press, 1986.

II. Gc chain blocking agents

A "gc chain blocking agent" can be identified by its ability to modulate (e.g., augment and/or diminish) the effects of cytokines on cells, which cytokines employ gc chain in their receptors. Such effects are well known to those of skill in the art and include, but are not limited to, effects on cell growth, on cell activation, on cell differentiation, and on the activation of intracellular components. The cell may be an immune or a nonimmune cell. Preferably, a gc-blocking agent is identified by its ability to significantly inhibit the proliferation of T cells or a T cell line in response to cytokine. By "significantly inhibit" it is intended to mean that the gc blocking agent can inhibit T cell proliferation by at least 25% on average as compared to a negative control agent. Preferably, the gc blocking agent is capable of inhibiting by at least 40% on average as compared to a negative control. Most preferably, the cytokine is IL-2 and the gc blocking agent is directed against IL-2R.

It is a unique feature of the present invention that this inhibition of the cellular response to a given cytokine can be achieved without the addition of an auxiliary molecule (i.e., a second agent directed against a component of the receptor for the same cytokine).

Any blocker of the interaction between the gc chain of the receptor and the receptor's cognate cytokine or between the gc chain of the receptor and another cytokine receptor chain (which participates in forming a functional cytokine receptor) is useful in the methods of the invention. Such inhibitors include gc-blocking antibody homologs, anti-cytokine antibody homologs, soluble gc-blocking polypeptides, gc-binding polypeptides, small molecules, e.g., carbohydrates, and mimetic agents of each of the above and their derivatives thereof. Preferred gc blocking agents are gc-blocking antibody homologs and soluble gc-blocking polypeptides.

As discussed below (see Section III), the utility of the compositions of the invention may easily be determined by assaying their ability to block a response of a cell to a particular cytokine (e.g., IL-2) and more preferably block this response without the need for a second agent which also affects the response of the immune cell to the same cytokine (i.e., "auxiliary agent"). The ability of the compositions of the invention to block the response of a cell to IL-2 and one or more other cytokines also may be readily determined (see below).

a. gc-blocking antibody homologs:

As used herein, a "gc-blocking antibody homolog" is a protein comprising one or more polypeptides selected from immunoglobulin light chains, immunoglobulin heavy chains and antigen-binding fragments thereof (e.g. F(ab) or sFv fragments) which are capable of binding to one or more gc chain components of a cytokine receptor. The component polypeptides of an antibody homolog include, but are not limited to, intact immunoglobulins of types IgA, IgG, IgE, IgD, IgM (as well as subtypes thereof), wherein the light chains of the immunoglobulin may be of types kappa or lambda.

A "gc-blocking antibody" of the invention is a subset of the class of gc chain blocking agents which are antibodies and which are capable of significantly blocking a response of a cell to a cytokine which employs the gc chain as part of its cell surface receptor. Blocking may occur by decreasing or weakening the binding of gc chain to a ligand or to another receptor chain that is a component of a cytokine receptor, or by other means such as interfering with gc chain clustering or with cellular functions (such as second messenger compounds or other signaling mechanisms) which are generated in response to gc-ligand interactions, a blocking agent thereby diminishes the response of a cell to cytokine.

B. Production of gc-blocking antibodies

Antibodies to the cytokine receptor gc chain can be produced by conventional techniques. Antibodies can be polyclonal, or more preferably, are monoclonal. For example, a mammal such as a mouse, hamster or rabbit can be immunized with an antigen (also called an "immunogen") or with a cell expressing the antigen, to elicit an antibody response against the antigen in the animal. The immunogen is preferably a purified protein, a protein made by recombinant DNA methods or a fragment thereof, or a chemically synthesized protein or synthetic peptide. Most preferably, the immunogen is identical in sequence to a protein or protein fragment of human origin such as a gc chain polypeptide (see Examples). It is also possible to utilize an immunogen identical in sequence to a protein of non-human, mammalian origin such as the gc chain polypeptide of a mouse, although the resulting monoclonal antibodies (e.g., mouse anti-mouse mAbs) may be less preferred for therapeutic purposes than, for example, mouse anti-human monoclonal antibodies. Alternatively, tissue or a whole organ which expresses the antigen can be used to elicit antibodies. In another method, DNA encoding the antigen is injected into muscle tissue, which expresses the antigen in vivo and elicits an immune response (Donnelly et al., *Ann. N.Y. Acad. Sci.* 772:4046 (1995)). The progress of immunization can be monitored by detection of antibody titers in plasma or serum. Standard ELISA or other immunoassay can be used with the antigen to assess the level of antibodies. Following immunization, antisera can be obtained and, if desired, polyclonal antibodies isolated from the sera.

We have discovered that if a non-denatured form protein immunogen is not used, methods of producing antibodies against the protein are not successful. That is, we have discovered a method whereby antibodies can be raised against a protein antigen by administering as an immunogen a non-denatured from of that protein antigen. Therefore, in a preferred embodiment of the invention, the mammal is immunized with non-denatured gc chain antigen. This non-denatured antigen shares epitopes with the biologically relevant form of gc; i.e. it retains a conformation comprised of non-contiguous sequences in the peptide chain of the intact gc molecule. Conventional immunization procedures; e.g. emulsification in Freund's complete or incomplete adjuvant would tend to denature the conformation of the intact protein and destroy the conformation or biologically relevant epitopes. In a preferred embodiment of the invention, one would immunize a mammal with a non-denatured form of gc and if other features of a denaturing adjuvant were desired, inject this material at an alternate site. In another embodiment, the gc molecule is 'fused' to an Fc region (gc-Ig), using standard recombinant techniques, and mounted on a protein-a agarose bead, which would serve to present the molecule in a conformationally intact form, while also providing a costimulatory signal for B cells. Alternatively, the gc-Ig construct could be bound to another carrier and co-administered with a denaturing or non-denaturing adjuvant or without adjuvant. In another embodiment, the gc molecule may be 'fused' to a small peptide in such a way so as not to interfere with its biological function or its conformation. Monoclonal antibodies to these small peptides can then be used to orient the presentation of gc, either as a soluble complex or mounted on an insoluble carrier. In another embodiment, a conformationally relevant epitope is modeled, using structural information, in the form of a linear peptide, and immunized with a denaturing or non-denaturing adjuvant. Any of these embodiments may be injected intra peritoneally, subcutaneously, intradermal, intrasplenically, or intranodally. Immunization prior to fusion preferably uses intravenous challenge with a form of gc compatible with this route, usually in solution. These forms may include gc in solution, gc-Ig in solution, gc-peptide in solution, gc-peptide prebound to a mAb anti-peptide in solution, gc bound to a carrier in solution, or other forms of the molecule designed to retain conformation or biologically relevant structure.

To produce monoclonal antibodies, antibody producing cells (lymphocytes) can be harvested from an immunized animal and fused with myeloma cells using standard somatic cell fusion procedures thus immortalizing these cells and yielding hybridoma cells. Such techniques are well known in the art. For example, the hybridoma technique originally developed by Kohler and Milstein, *Nature* 256:495–497, 1975) as well as other techniques such as the human B-cell hybridoma technique (Kozbar et al., *Immunol. Today* 4:72, 1983) and the EBB-hybridoma technique to produce human monoclonal antibodies (Cole et al., *Monoclonal Antibodies in Cancer Therapy*, Allen R. Bliss, Inc., pages 77–96, 1985) can be used. Hybridoma cells can be screened immunochemically for production of antibodies specifically reactive with the antigen and monoclonal antibodies isolated.

One of the essential tools for discovering monoclonal antibodies with desired blocking properties is an appropriate screen or selection system in which the preferred mAbs are rendered conspicuous by their performance. In the preferred embodiment of the present invention, a screen for blocking antibodies would include the ability of the monoclonal antibody to capture gc chain or a fragment or derivative thereof from solution or to bind to cells expressing gc chain, and to inhibit the binding of a cytokine to a receptor or to block the function of a cytokine on a cell. It will be recognized by one skilled in the art, that these screens can be arranged to discover monoclonal antibodies whose activities are conspicuous in one or more of these assays.

Another method of generating specific antibodies or antibody fragments reactive against gc chain is to screen expression libraries encoding immunoglobulin genes, or portions thereof, expressed in bacteria with the antigen (or a portion thereof). For example, complete Fab fragments, $V_H$ regions, $F_V$ regions and single chain antibodies can be expressed in bacteria using phage expression libraries. (Ward et al., *Nature* 341:544–546, 1989; Huse et al., *Science* 246:1275–1281, 1989; and McCafferty et al. *Nature* 348:552–554, 1990.) Expression libraries may be constructed from cDNA derived from unimmunized or immunized animals, such as mammals, particularly human or non-human primates. Alternatively, the SCID-hu mouse can be used to produce antibodies, or fragments thereof.

Antibodies can be fragmented using conventional techniques and the fragments screened for utility in the same manner as described above for whole antibodies, e.g. the ability to inhibit an interaction between gc chain and a gc chain ligand such that it can inhibit gc chain signaling. For example, $F(ab')_2$ fragments can be generated by treating antibody with pepsin. The resulting $F(ab')_2$ fragment can be treated to reduce disulfide bridges to produce Fab' fragments.

The present invention is further intended to include derivatives of antibodies or fragments thereof which retain a desired functional property, e.g., the ability to inhibit an interaction between gc chain and a gc chain ligand. Antibody derivatives include chimeric molecules, humanized molecules, molecules with reduced effector functions, bispecific molecules, and conjugates of antibodies or antibody portions with toxins or radionuclides. An antibody, or fragment thereof, produced in a non-human subject can be recognized to varying degrees as foreign when the antibody is administered into a human subject and an immune response against the antibody may be generated in the subject. One approach for minimizing or eliminating this problem is to produce chimeric, humanized, or primatized antibody derivatives, i.e., antibody molecules comprising portions which are derived from non-human antibodies (e.g., derived from mice or monkeys) and portions which are derived from human antibodies. Chimeric antibody molecules can include, for example, the variable region from an antibody of a mouse, rat or other species, with human constant regions, a variety of approaches for making chimeric antibodies have been described. (See, for example, Morrison et al., *Proc. Natl. Acad. Sci. U.S.A.* 81,6851 (1985); Takeda et al., *Nature* 314, 452 (1985), Cabilly et al., U.S. Pat. No. 4,816,567; Boss et al., U.S. Pat. No. 4,816,397; Tanaguchi et al., EP 171496; European Patent Publication 0173494, United Kingdom Patent GB 2177096B.) In a further modification, humanized antibodies have only the hypervariable domains of the variable region of non-human origin and have other parts of the variable region of the antibody, especially the conserved framework regions of the antigen-binding, domain, of human origin. Such humanized antibodies can be made by any of several techniques known in the art, (e.g., Teng et al., *Proc. Natl. Acad. Sci. U.S.A.* 80, 7308–7312 (1983); Olsson et al., *Meth. Enzymol.*, 92, 3–16 (1982)), and are preferably made according to the teaching of PCT Publication WO 92/06193 or EP 0239400. Humanized antibodies can be commercially produced by, for example, Scotgen Limited, 2 Holly Road, Twickenham, Middlesex, Great Britain.

In yet another available method, transgenic mice are created whose murine immunoglobulin genes have been inactivated and into which human immunoglobulin genes have been introduced. B cell lymphocytes from these transgenic mice can be immortalized as hybridomas using conventional technology. Hybridomas produced in this way secrete fully human IgG antigen-specific mAbs in good yield. See, for example, U.S. Pat. Nos. 5,591,669, 5,545,806 and 5,569,825. See also, Lonberg et al., *Nature,* 368: 856–859 (April 1994).

C. Isolated Polynucleotide Sequences

The heavy and light chain variable regions of an anti-gc antibody of the invention may be cloned and their sequence determined using techniques well known to one of skill in the art. For example, cellular RNA may be prepared from hybridoma cells by a guanidine thiocyanate extraction procedure and cDNAs encoding the variable regions cloned by RT-PCR from the total cellular RNA using the GIBCO BRL Superscript Preamplification System for First Strand cDNA synthesis following the manufacturer's recommended protocol using random hexamers for priming. For subsequent PCR amplification of cDNA, universal primers may be employed based on conserved sequences at the ends of the variable region domains. For the heavy chain variable region, the primers VH1FOR and VH1BACK may be employed (Orlandi et. al., *Proc. Natl. Acad. Sci. USA* 86:3833, (1989)). For the light chain variable region, one of a series of primers also previously described may be employed (Orlandi et. al., id.; Jones and Bendig, *Bio/Technology* 9:88 (1991)). The respective PCR products may then be blunted, kinased and subcloned into a sequencing vector for sequencing. See Example 2.

Preferred gc-blocking antibodies of this invention are those which cross-compete with the CP.B8 mAb or fragments of its variable region. We have identified preferred polynucleotide sequences encoding various portions of CP.B8. The invention therefore provides an isolated, substantially pure nucleic acid e.g., RNA or DNA, having or comprising a nucleotide sequence which encodes a polypeptide, the amino acid sequence of which includes, or is the sequence, of a gc blocking agent. This includes double stranded nucleic acids as well as coding and antisense single strands as well as polynucleotides that hybridize to the identified sequences under standard hybridization conditions.

The deduced amino acid sequence for the heavy chain variable region of CP.B8 is listed below as SEQ ID NO: 3. The complementarity determining regions (CDRs) are in bold:

LQESGPGLVAPSQSLSITCTVSGFSLTSYGVHWVRQPPGK

GLEWLGVIWAGGSTNYNSALMSRLNINRDNSKSQIFLKMN

SLQTDDTAIYYCAREGSTVDSMDYWGQGTTVT

The deduced amino acid sequence of the light chain variable region for CP.B8 is shown below as SEQ ID NO.: 4. The CDRs are in bold:

DIVMTQSHKFMSTSVGDSITITCKASQDVTTAVAWYQQKPGQSPKLLIY

WASTRHTGVPDRFTGSGSGTDYTLTISSVQAEDLALYYCQQHYITPWTF

GGGTKLEI

The cDNA sequence of the light chain variable region of CP.B8 is shown below as SEQ ID NO. 5.

Light Chain

GATATCGTAATGACCCAGTCTCACAAATTCATGTCCACATCAGTAGGAGA

CAGTATCACCATCACCTGCAAGGCCAGTCAGGATGTGACTACTGCTGTAG

CCTGGTATCAACAAAAACCAGGGCAATCTCCTAAACTTCTGATTTACTGG

GCATCCACCCGGCACACTGGAGTCCCTGATCGCTTCACAGGCAGTGGATC

TGGGACAGATTATACTCTCACCATCAGCAGTGTGCAGGCTGAAGACCTGG

CACTTTATTACTGTCAGCAACATTATATCACTCCGTGGACGTTCGGTGGA

GGGACCAAGCTGGAGATCT

The cDNA sequence of the heavy chain variable region of CP.B8 is shown below as SEQ ID NO. 6.

Heavy chain

CTGCAGGAGTCAGGACCTGGCCTGGTGGCGCCCTCACAGAGCCTGTCCAT

CACTTGCACTGTCTCTGGGTTTTCATTAACCAGCTATGGTGTACACTGGG

TTCGCCAGCCTCCAGGAAAGGGTCTGGAGTGGCTGGGAGTCATTTGGGCT

GGTGGAAGCACAAATTATAATTCGGCTCTCATGTCCAGACTGAACATCAA

CAGAGACAATTCCAAGAGCCAAATTTTCTTAAAAATGAACAGTCTGCAAA

CTGATGACACAGCCATCTACTACTGTGCCAGAGAGGGTTCTACGGTAGAT

TCTATGGACTACTGGGGCCAAGGGACCACGGTCACC

Generally, preferred polynucleotides of the invention encode gc binding agents, or portions thereof, that have an amino acid sequence at least 60%, 80%, 90%, 95%, 98% or 99% homologous to an amino acid sequence encoded by the polynucleotides of SEQ ID NOS: 5 and/or 6. The polynucleotide sequences encode polypeptides that are at least 5, 10, 20, 50, 100 or 150 amino acids long. The polynucleotide encodes a polypeptide that includes at least 5, preferably at least 10, more preferably at least 20, and most preferably at least 50, 100, 150 contiguous amino acids.

In preferred embodiments, the polynucleotide encodes at least the variable region of an anti-gc antibody that is at least 20 residues in length and is preferably 50, 60, more preferably at least 70, 80, 90 or 95% homologous with the amino acid sequences encoded by SEQ ID NOS: 5 and/or 6.

The polynucleotide sequences of the invention may differ in base pair sequence from a sequence in SEQ ID NOS: 5 and/or 6 such that the encoded polypeptide can be considered a "variant" of a gc chain blocking agent (See Section G, below). These differences are such that the encoded gc chain blocking agent exhibits biological utility e.g., it is at least able to block the cellular response to IL-2 without the requirement for an auxiliary agent which also affects the response to IL-2.

The DNA sequences of the invention also includes those encoding other N-terminal or C-terminal amino acid sequences. For example, the polynucleotide may include all or a fragment of a sequence from SEQ ID NOS: 5 and/or 6 such that it encodes a protein fused, in reading frame, to additional amino acid residues, preferably to residues encoded by genomic DNA 5' to the genomic DNA which encodes a sequence from SEQ ID NOS: 5 and/or 6. The polynucleotide may also encode a recombinant fusion protein having a first gc blocking agent portion and a second polypeptide portion having an amino acid sequence unrelated to the gc blocking agent. The second polypeptide may be any of, for instance, glutathione-S-transferase, a DNA binding domain, or a polymerase activation domain. The fusion protein may be used in a two-hybrid assay.

Preferably, the polynucleotides encode the complementarity determining region (CDR) of a gc blocking agent, for example: amino acids 28 to 32 of SEQ ID NO. 3, amino acids 47 to 61 of SEQ ID NO.3; amino acids 95 to 104 of SEQ ID NO. 3; amino acids 24 to 34 of SEQ ID NO. 4; amino acids 50 to 56 of SEQ ID NO 4; and amino acids 89 to 97 of SEQ ID NO. 4.

The subject DNA sequences of the invention may include a transcriptional regulatory sequence, e.g., at least one of a transcriptional promoter or transcriptional enhancer sequence, operably linked to the a gene sequence to render the particular polynucleotide encoding the gc blocking agent suitable for use as an expression vector. In yet another embodiment, the nucleic acid which encodes at least a portion of a gc blocking agent hybridizes under stringent conditions to a nucleic acid probe corresponding to at least 12 consecutive nucleotides from SEQ ID NO: 5 and/or SEQ ID NO: 6, more preferably to at least 20 consecutive, and most preferably to at least 40 consecutive.

The invention also includes a probe or primer which comprises a substantially purified oligonucleotide. The oligonucleotide includes a region of nucleotide sequence which hybridizes under stringent conditions to at least 10 consecutive nucleotides of sense or antisense sequence from SEQ ID NO: 5 and/or SEQ ID NO: 6 or naturally occurring mutants thereof. The probe may also include a label attached thereto such as a radioisotope, a fluor, an enzyme or enzyme cofactor. The oligonucleotide may be at least 10 20, 30, 50, 100, 150 nucleotides long.

D. Soluble gc-binding polypeptides and Soluble gc-blocking Polypeptides:

"Soluble gc-binding" polypeptides that bind to an antigenic determinant of the gc chain and block a response of an cell to IL-2 or IL-2 and one or more other cytokines are useful in the present methods and include polypeptides derived from cytokine or cytokine receptor chains or from fusion constructs thereof.

"Soluble gc-blocking polypeptides" are also useful. Soluble gc blocking polypeptides may be derived from the gc chain and may particularly include the amino terminal 254 amino acids of mature gc chain (included within SEQ ID NO.2) or peptides derived therefrom, a primary screen which may be employed to assess a series of putative soluble gc blocking polypeptides or peptides is comprised of a cytokine binding assay well know to one of skill in the art (in *Current Protocols in Immunology* 1:6.1.1–6.1.15, Coligan, Kruisbeek, Marguiles, Shevach and Stober, Eds., John Wiley and Sons (1994)). Therein, the binding of a cytokine conjugated to a detection agent, such as a radiolabel, to the surface of cells in the presence and absence of a gc-binding or soluble gc-blocking polypeptide is assessed. In another and preferred assay, these polypeptides are assessed for their ability to block a response of a cell to IL-2 or IL-2 and one or more other cytokines, preferably without the need to add a second agent which does affect the response of the cell to IL-2.

E. Soluble gc Mimetic Agents: Also useful in the invention are soluble gc mimetic agents which mimic the function of soluble gc and may be peptides, semi-peptidic compounds or non-peptide compounds. Mimetic agents are capable of blocking a response of a cell to IL-2 or IL-2 and one or more other cytokines, preferably without the need to add a second agent which affects the response of the cell to IL-2. Such mimetic agents may be produced by synthesizing a plurality of peptides (e.g., 5–20 amino acids in length), semi-peptidic compounds or non-peptidic, organic compounds, and then screening those compounds for blocking activity. The primary screen may be comprised of a cytokine binding assay similar to that described in Section B (above). In another and preferred assay, mimetics are assessed for their ability to block a response of a cell to IL-2 or IL-2 and one or more other cytokines, preferably without the need to add a second agent which does affect the response of the cell to IL-2. See generally, U.S. Pat. No. 4,833,092; Scott and Smith, "Searching for Peptide. Ligands with an Epitope Library", Science 249: 386–390 (1990) and Devlin et al., *Science.* 249: 404–407 (1990), all of which are incorporated herein by reference.

F. Derivatized gc Chain Blocking Agents: The gc blocking agents of the present invention may also be chemically modified to facilitate delivery to a target cell. One possible modification involves increasing the lipophilicity of the agent in order to increase cell surface binding and stimulate non-specific endocytosis of the gc binding agent, a wide variety of lipopeptides, fatty acids, and basic polymers (e.g., tripalmitoyl-S-glycerylcysteyl-seryl-serine; palmitic acid; polyarginine) may be linked to a gc chain blocking agent to accomplish this. See U.S. Pat. No. 5,219,990, incorporated herein by reference. The gc chain blocking agents of the invention may also be modified to increase their resistance to proteases by incorporating D-amino acids instead of L-amino acids at some or all amino acid residues. See, U.S. Pat. No. 5,219,990 supra.

Derivatized molecules, i.e., monoclonal antibody fragments such as the variable light and heavy chains, may be linked to a moiety by covalent or noncovalent linkages. The fused construct may be expressed in bacteria or yeast using standard techniques. Thus, polynucleotide sequences encoding gc blocking agents useful in the present invention, operatively linked to regulatory sequences, may be constructed and introduced into appropriate expression systems using conventional recombinant DNA techniques. The resulting fusion protein may then be purified and tested for its capacity to block immune responses to IL-2. For example, recombinant methods may be used to attach a moiety to sequences of mAb CP.B8 (see infra) by joining the polynucleotide sequence encoding for mAb CP.B8 with the polynucleotide sequence encoding the moiety and introducing the resulting construct into a cell capable of expressing the conjugate.

Two separate sequences may also be synthesized, either by recombinant means or chemically, and subsequently joined using known methods. Alternatively, the entire conjugate may be chemically synthesized as a single amino acid sequence, a preferred derivatized gc blocking agent includes a recombinantly-produced polypeptide in which a soluble gc blocking agent fused to all or part of an immunoglobulin heavy chain hinge region and all or part of a heavy chain constant region. Most preferred are gc blocking agents fused to a portion of a human IgG1 hinge region (including the C-terminal ten amino acids of the hinge region containing two cysteine residues) and the CH2 and CH3 regions of an IgG1 heavy chain constant domain. Such fusion proteins are expected to exhibit prolonged serum half lives and provide gc blocking agents which are bivalent.

Useful moieties also include, for example, cytotoxic agents of pharmaceutical agents. Useful pharmaceutical agents include biologically active peptides, polypeptides and proteins, such as cyclosporin a, steroids, retinioids, interferon and nitrogen mustard.

Chemical (i.e., non-recombinant) attachment of gc blocking agent sequences to a moiety such as a radiolabel or a biologically active material, may be effected by any means which produces a link between the two components which can withstand the conditions used and which does not significantly alter the function of either component. Many chemical cross-linking agents are known and may be used to join a gc blocking agent sequences to another moiety. Among the many intermolecular cross-linking agents are, for example, succinimidyl 3-(2-pyridyldithio)propionate (SPDP) or N,N'-(1,2-phenylene)bismaleimide are highly specific for sulfhydryl groups and form irreversible linkages; N,N'-ethylene-bis-(iodoacetamide) (specific for sulfhydryl); and 1,5-difluoro-2,4-dinitrobenzene (forming irreversible linkages with tyrosine and amino groups). Other agents include p,p'-difluoro-m,m'-dinitrodiphenylsulfone (forming irreversible linkages with amino and phenolic groups); dimethyl adipimidate (specific for amino groups); hexamethylenediisocyanate (specific for amino groups); disdiazobenzidine (specific for tyrosine and histidine); succinimidyl 4-(N-maleimidomethyl)cyclohexane-1-carboxylate (SMCC); m-maleimidobenzoyl-N-hydroxysuccinimide ester (MBS); and succinimide 4-(p-maleimidophenyl)butyrate (SMPB). The succinimidyl group of these cross-linkers reacts with a primary amine, and the thiol-reactive maleimide reacts with the thiol of a cysteine residue. See, Means and Feeney, *Chemical Modification of Proteins*, Holden-Day, 39–43, 1974; and S. S. Wong, *Chemistry of Protein Conjugation and Cross-Linking*, CRC Press, 1971. All the cross-linking agents discussed herein are commercially available and detailed instructions for their use are available from the suppliers.

G. Variants of gc chain blocking agents

The invention also includes variants of gc chain blocking agents, which can differ in amino acid sequence or in ways that do not involve sequence, or both. Variants in amino acid sequence are produced when one or more amino acids is substituted with a different natural amino acid, an amino acid derivative or non-native amino acid. Particularly preferred variants include those with sequences which differ from those specified by one or more conservative amino acid substitutions, which typically have minimal influence on the secondary structure and hydrophobic nature of the protein or peptide. Variants may also have sequences which differ by one or more non-conservative amino acid substitutions, deletions or insertions which do not significantly alter the binding specificity of the given gc chain blocking agents. Conservative substitutions typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions can be taken from the Table below, and yet others are described by Dayhoff in the *Atlas of Protein Sequence and Structure* (1988).

TABLE 1

CONSERVATIVE AMINO ACID REPLACEMENTS

| For Amino Acid | Code | Replace with any of |
|---|---|---|
| Alanine | a | D-Ala, Gly, beta-Ala, L-Cys, D-Cys |
| Arginine | R | D-Arg, Lys, homo-Arg, D-homo-Arg, Met, D-Met, Ile, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Beta-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val, Norleu |
| Phenylalanine | F | D-Phe, Tyr, D-Thr, L-Dopa, His, D-His, Trp, D-Trp, Trans 3,4 or 5-phenylproline, cis 3,4 or 5 phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), Val, D-Val |
| Threonine | T | D-Thr, Ser, D-Ser, allo-Thr, Met, D-Met, Met)O, D-Met(O), Val, D-Val |

TABLE 1-continued

CONSERVATIVE AMINO ACID REPLACEMENTS

| For Amino Acid | Code | Replace with any of |
|---|---|---|
| Tyrosine | Y | D-Tyr, Phe, D-Phe, L-Dopa, His, D-His |
| Valine | V | D-Val, Leu, D-Leu, Ile, D-Ile, Met, D-Met |

Other variants within the invention are those with modifications which increase peptide stability. Such variants may contain, for example, one or more non-peptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants. Incorporation of D- instead of L-amino acids into the polypeptide may increase its resistance to proteases. See, e.g., U.S. Pat. No. 5,219,990.

Generally, substitutions that may be expected to induce changes in the functional properties of gc blocking agents such as anti-gc chain antibodies are those in which: (I) a hydrophilic residue, e.g., serine or threonine, is substituted by a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative charge, e.g., glutamic acid or aspartic acid; or (iv) a residue having a bulky side chain, e.g., phenylalanine, is substituted for (or by) one not having such a side chain, e.g., glycine.

The gc blocking agents of this invention may also be modified by various changes such as insertions, deletions and substitutions, either conservative or nonconservative where such changes might provide for certain advantages in their use.

In other embodiments, variants with amino acid substitutions which are less conservative may also result in desired derivatives, e.g., by causing changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

In particular, the invention further includes variants and derivatives of the antibodies of the invention which are selected by expression of antibody fragments on bacteriophage with selection for improved binding affinity or changes in fine specificity. Improvement in binding affinity may be achieved by techniques such as chain shuffling and CDR shuffling (Johnson and Chiswell, *Curr. Opin. Struc. Biol.* 3:564–571 (1993); Marks, pp. 53–88 in *Antibody Engineering*, Borrebaeck, Ed., (1996)), which are well known to those of skill in the art. For use therapeutically, it may be preferred that an antibody preparation be unable to fix complement or induce other effector functions. Complement fixation can be prevented by deletion of the Fc portion of the antibody, by using antibody isotype which is not capable of fixing complement, or, less preferably, by using a complement fixing antibody in conjunction with a drug which inhibits complement fixation. Alternatively, amino acid residues within the Fc region which are important for activating complement (see e.g., Tan et al., *Proc. Natl. Acad. Sci. U.S.A.* 87: 162–166, 1990; Duncan and Winter, *Nature* 332:738–740, 1988) can be mutated to reduce or eliminate the complement-activating ability of an intact antibody. Likewise, amino acids residues within the Fc region which are important for binding of the Fc region to Fc receptors (see e.g., Canfield and Morrison, *J. Exp. Med.* 173:1483–1491, 1991; and Lund et al., *J. Immunol.* 147:2657–2662, 1991) can also be mutated to reduce or eliminate Fc receptor binding if an intact antibody is to be used.

III. Testing Compounds of the Invention for Biological utility

To determine whether or not a particular gc blocking agent actually binds to the gc chain, conventional binding assays may be used. These include immunofluorescent staining assays, ELISA assays, radioimmunoassays and the like which detect binding of gc blocking agents to human gc chain. One may employ cell suspensions which express the gc chain, or recombinant soluble forms of human gc chain which have been engineered to contain a peptide tag and which retain native conformation. (Johnson et al., *Eur. Cytokine Network* 5:23–34 (1994)). In the latter case, a mAb directed against the peptide tag can be employed to anchor the soluble protein to a solid surface. The binding of a gc blocking agent (e.g., an antibody) to human gc chain or to soluble fragments thereof may be conveniently detected through the use of a secondary antibody specific for immunoglobulins of the species from which the antibody is derived. This secondary antibody may be conjugated to a fluorochrome, to an enzyme or to a radiolabel.

One of skill in the art may easily determine, using well known methods, whether a particular gc blocking agent of the invention displays biological utility. For example, with an antibody or antibody homolog, the ability of antibodies to block cellular responses to cytokines may be measured by their ability to inhibit cytokine-induced responses of normal cells or of cell lines which express cytokine-specific receptors which encompass the gc chain. (Hamblin, *Cytokines and Cytokine Receptors*, p. 17 and references, Eds. Rickwood and Male, Oxford University Press (1993); *Human Cytokines*, pp. 83–83, 115, 172, Eds. Aggarwal and Gutterman, Blackwell Scientific Publications (1992)). These normal cells or cell lines will be responsive when exposed to cytokine (such as IL-2, IL4, IL-7, IL-9 or IL-15) in vitro, and may be dependent on cytokine stimulation for growth. The cells or cell lines should not express alternative receptors (i.e. receptors that do not employ gc chain) that allow them to respond to any of the above cytokines. The response of the normal cells or cell lines to cytokine can be readily assessed by measuring cell proliferation, such as evidenced by cellular incorporation of $^3$H-thymidine. The effect of an inhibitor agent, such as an antibody, can be determined by measuring cytokine-induced cell proliferation in the absence or presence of the potential inhibitor. While the dose of cytokine can be varied, employing a cytokine dose which induces at least 50% of the maximum stimulation by that cytokine will provide a means to assess the effectiveness of potential blocking agents, including gc chain-blocking antibodies. The dose of inhibitor may also be varied.

a preferred method for determining the ability of antibodies to block cell responses to cytokines utilizes normal cells, such as freshly isolated peripheral blood mononuclear cells (PBMC). PBMC may be activated by phytohemagluttinin (PHA), thereby polyclonally stimulating T cells to express gc chain-encompassing cytokine receptors and to release growth factors which support their polyclonal expansion. By 3–4 days after PHA stimulation, the level of endogenous cytokine production by this population is sharply diminished yet the cells are still cytokine-responsive. In order to employ these cells, they may be harvested on day 3, washed to remove any endogenous cytokines released and cultured during an overnight rest period. Alternatively cells may be harvested and employed on day 4. PHA-blasts can then be cultured with varying doses of cytokine in order to determine a cytokine dose which supports at least 50% of maximum stimulation by that factor. The ability of an inhibitor agent, such as an antibody, to block cytokine-induced growth can then be assessed with varying doses of agent. Cell growth is assayed after 36–48 hours by the incorporation of $^3$H-thymidine during the final 8–16 hours of culture. Activated T cells should be employed as the responsive population, thereby avoiding the potential for alternative (non-gc chain-containing) receptors that allow them to respond to any of the above cytokines even if response by gc chain-containing receptors is inhibited. One example of alternative receptors is a type of IL-4 receptor on B lymphocytes. (Callard et. al., *Immunology Today*, 17:108–110 (1996). If more than 15% B cells are present in the responding population, they are removed prior to addition of cytokine using negative selection techniques standard to one of skill in the art, such as by using B cell specific mAbs coupled to magnetic particles (Perceptive Diagnostic, Cambridge, Mass.). Using this preferred assay, T cell proliferation in response to a dose of cytokine sufficient to induce at least 50% of maximal stimulation, a gc-blocking antibody is intended to encompass inhibition of a cellular response to a cytokine by at least 25% on average, relative to a negative control, such as control Ig protein which recognizes an irrelevant antigen. Preferably, the mAb is capable of inhibiting by at least 40% on average, relative to a negative control. Cytokines that may be employed include IL-2, IL-4, IL-7, IL-9 and IL-15.

Using the assay described above, one may readily determine whether or not a particular antibody is capable of blocking the cell response to IL-2 or another cytokine or plurality of cytokines according to the present invention. The assay described above may also be used to determine whether an agent can block a cytokine response without requiring addition of a second agent which also affects the cellular response to the same cytokine.

Still other assays that may be employed to identify the antibodies encompassed in the present invention are those that measure activation of intracellular mediators involved in the gc chain signaling pathway upon exposure of cells to cytokine. Intracellular mediators including Jak-1 and Jak-3 kinase and various STAT proteins, and methods to measure their activation, have been described (Schindler and Darnell, *Annu. Rev. Biochem* 64:621–651 (1995); Ivashkiv, *Immunity* 3:1–4 (1995)). Alternatively, the transcriptional activation of genes such as c-fos, c-myc and c-jun (Asao et al., *Proc. Natl. Acad. Sci. USA* 90:4127–4131 (1993) may be assessed.

IV. Using Compounds of the Invention a. Common gc chain blocking agents which induce T cell unresponsiveness The ability of a gc-blocking agent of the invention to induce T cell unresponsiveness (i.e., induce T cell anergy) can be readily determined by conventional techniques known to one of skill in the art. The term "T cell unresponsiveness" as used herein refers to a reduction in or lack of T cell proliferation, or lymphokine secretion or in the induction of effector functions by a T cell upon re-exposure to the antigen or antigenic portion of the antigen. The induction of T cell unresponsiveness refers to the initial establishment of an unresponsive state.

The ability of an agent to inhibit T cell proliferation in response to one or more cytokines which employ the gc chain can be assessed in vitro as previously described above, preferably employing PHA-activated PMBC responsive to a variety of cytokines which employ gc chain (See Section III). An ability to block responses to IL-2 and one or more other cytokines is indicative of a gc-blocking agent able to induce T cell unresponsiveness after antigen stimulation. An agent which can block responses to IL-2 and a plurality of other cytokines is preferred since numerous cytokines may contribute to T cell responses.

A second assay measures the ability of a T cell to respond to a specific antigen upon restimulation with that antigen. T cells previously stimulated with a specific antigen, or antigen-specific T cell lines or clones are employed. The T cells are generated by conventional techniques (in *Current Protocols in Immunology* 1:7.19.1–7.19.7, Coligan, Kruisbeek, Marguiles, Shevach and Stober, Eds., John Wiley and Sons (1994); Goronzy et. al., in *Methods in Enzymology* 150:333–341 (1987)). After primary culture with antigen presented by APCs in the absence of a costimulatory molecule (such as a CD28-ligand) these T cells can be recovered. However, on subsequent restimulation by the specific antigen and competent APCs, the T cell population will exhibit unresponsiveness as evidenced by a significantly reduced response or a lack of response (Schwartz, *Science* 248:1349–1356 (1990)). Likewise, T cells may be stimulated by antigen and competent APCs in the presence or absence of a gc-blocking agent, such as an antibody to gc chain or other compositions of the invention. These cells can then be recovered and their ability to respond upon restimulation with antigen and competent APCs measured, for eg, by proliferation or cytokine production. While this second assay is useful, it may be limited to the extent that antigen-specific stimulation of T cells in vitro is often principally driven by IL-2 whereas numerous cytokines may be redundant in their ability to support T cell activation under physiologic conditions. These include, IL-2, IL-4, IL-7, IL-9 and IL-15. Thus, the second assay is preferably employed in addition to that referred to above.

B. Common gc chain blocking agents Which Differentially Modulate Th1 vs. Th2 Immune Activities This invention further pertains to gc chain blocking agents, such as gc blocking antibodies, which can significantly diminish cellular signaling through the gc chain of cytokine receptors following contact of the cell with Th1-type cytokines but not Th2-type cytokines, or conversely with Th2-type cytokines but not mi-type cytokines. In one embodiment, the gc chain blocking mAb is able to block the response to IL-2 (a Th1 cytokine) but does not inhibit responses to Th2-type cytokines. In another embodiment, the mAb is able to block the response to one or more of the other Th1-type cytokines, but does not inhibit responses to Th$^2$-type cytokines. Other antibodies of the invention selectively inhibit cellular responses to one or more Th2-type cytokines without blocking responses to Th1-type cytokines.

Using a preferred assay for measuring a cytokine-dependent growth response, such as the ability of PHA-activated T cells to proliferate in response to cytokine (described above), one may employ different cytokines to induce the cell response in the absence or presence of potential inhibitors. Alternatively, one may employ freshly isolated, purified T cells depleted of antigen presenting cells and stimulate their growth with a mAb directed against the TcR/CD3 directed mAb OKT3 which is immobilized on the tissue culture wells and with specific cytokine (Armitage et al., *J. Immunol.* 144:938–941 (1990)). One may thereby readily determine whether or not a particular antibody is capable of selectively blocking the cell response to some but not other cytokines. That is, one can identify antibodies according to the present invention that are able to block the response to IL-2, but not to one or more Th2-type cytokines. One can also identify antibodies according to the present invention which can block the response to one or more other Th1-type cytokines but do not block the response to one or more Th2-type cytokines besides IL-2. One can further identify antibodies which can block the cell response to one or more Th2-type cytokines but do not block the response to one or more Th1-type cytokines.

Another means to identify antibodies according to the present invention which differentially block Th1 vs. Th2 responses is to assess their effect on the differentiation of Th1 cells and Th2 cells in vitro. Freshly isolated PBMC may be activated with a mitogen, such as Con a or PHA, or with a TcR/CD3 directed mAb OKT3. In addition, various cytokines and/or cytokine-specific mAbs are included in the culture media in order to promote the differentiation of Th1 or Th2 cells. For example, any permutation of one or more of the cytokines IL-2, IL-12, and IFNγ and mAb specific for IL4 may be used to promote the differentiation of Th1 cells, whereas IL-4 may be used to promote the differentiation of Th2 cells. (Swain et al., *J. Immunol.* 145:3796–3806 (1990); Le Gros et al., *J. Exp. Med.* 172:921–929 (1990)). If purified CD4+ T cells are employed, the OKT3 should be co-immobilized with recombinant soluble costimulatory molecules, with soluble cytokines or cytokine-specific mAbs added to the culture media (Semnani et al., *J. Exp. Med.* 180:2125–2135 (1994)). Alternatively, a specific antigen presented by APC can be employed to activate T cells in culture, with very low or very high antigen doses promoting Th2 cells and mid-range antigen doses promoting Th1 cells. (Hosken et al., *J. Exp. Med.,* 182:1579–1584 (1995)). The differentiation of Th1 vs. Th2 cells can be assessed by harvesting the cells 3–5 days after primary stimulation and restimulating them as before in the absence of added cytokines or cytokine-specific mAbs. Two days after restimulation the relative levels of secreted cytokines, such as IFNγ and IL-4 or IL-5, are determined, with relatively high levels of IFNγ reflecting the development of Th1 cells and, conversely, relatively high levels of IL-4 or IL-5 indicating the development of Th2 cells. As an alternative to measuring secreted cytokines, the frequency of Th1 vs. Th2 cells that have developed can be determined by immunofluorescent detection of intracellular IFNγ and IL-4 (Openshaw et al., *J. Exp. Med.* 182:1357–1367 (1995)). Using this differentiation culture system, the effect of potential gc blocking agents on the generation of Th1 or Th2 cells can be readily determined by including such agents in the corresponding cultures during the initial 3–5 day stimulation.

C. Gene Therapy

Any of the methods known in the art for the insertion of polynucleotide sequences into a vector may be used to prepare vectors that can introduce polynucleotides of the invention into a cell. See, for example, Sambrook et al., *Molecular Cloning: a Laboratory Manual*, Cold Spring Harbor Laboratory, Cold Spring Harbor, N.Y. (1989) and Ausubel et al., *Current Protocols in Molecular Biology*, J. Wiley & Sons, NY (1992), both of which are incorporated herein by reference. Conventional vectors consist of appropriate transcriptional/translational control signals operatively linked to the polynucleotide sequence for a particular mutant proto-oncogene. Promoters/enhancers may also be used to control expression of mutant oncoproteins. Promoter activation may be tissue specific or inducible by a metabolic product or administered substance. Such promoters/enhancers include, but are not limited to, the native E2F promoter, the cytomegalovirus immediate-early promoter/enhancer (Karasuyama et al., *J. Exp. Med.,* 169: 13 (1989)); the human beta-actin promoter (Gunning et al., *Proc. Nat. Acad. Sci. USA,* 84: 4831 (1987); the glucocorticoid-inducible promoter present in the mouse mammary tumor virus long terminal repeat (MMTV LTR) (Klessig et al., *Mol. Cell. Biol.,* 4: 1354 (1984)); the long terminal repeat sequences of Moloney murine leukemia virus (MULV LTR) (Weiss et al., *RNA Tumor Viruses,* Cold Spring Harbor Laboratory, Cold Spring Harbor, N.Y. (1985)); the SV40 early region promoter (Bernoist and Chambon, *Nature,* 290:304 (1981)); the promoter of the Rous sarcoma virus (RSV) (Yamamoto et al., *Cell,* 22:787 (1980)); the herpes simplex virus (HSV) thymidine kinase promoter (Wagner et al., *Proc. Nat. Acad. Sci. USA,* 78: 1441 (1981)); the adenovirus promoter (Amata et al., *Proc. Nat. Acad. Sci. USA,* 82: 3567 (1985)).

Expression vectors compatible with mammalian host cells for use in gene therapy of tumor cells include, for example, plasmids; avian, murine and human retro viral vectors; adenovirus vectors; herpes viral vectors; and non-replicative pox viruses. In particular, replication-defective recombinant viruses can be generated in packaging cell lines that produce only replication-defective viruses. See *Current Protocols in Molecular Biology*: Sections 9.10–9.14 (Ausubel et al., eds.), Greens Publishing Associates, 1989.

Specific viral vectors for use in gene transfer systems are now well established. See for example: Madzak et al., *J. Gen. Virol.,* 73: 1533–36 (1992: papovavirus SV40); Berkner et al., *Curr. Top. Microbiol. Immunol.,* 158: 39–61 (1992: adenovirus); Moss et al., *Curr. Top. Microbiol. Immunol.,* 158: 25–38 (1992: vaccinia virus); Muzyczka, *Curr. Top. Microbiol. Immunol.,* 158: 97–123 (1992: adeno-associated virus); Margulskee, *Curr. Top. Microbiol. Immunol.,* 158: 67–93 (1992: herpes simplex virus (HSV) and Epstein-Barr virus (HBV)); Miller, *Curr. Top. Microbiol. Immunol.,* 158: 1–24 (1992:retrovirus); Brandyopadhyay et al., *Mol. Cell. Biol.,* 4: 749–754 (1984: retrovirus); Miller et al., *Nature,* 357: 455–450 (1992: retrovirus); Anderson, *Science,* 256: 808–813 (1992:retrovirus), all of which are incorporated herein by reference.

In a specific embodiment of a gene therapy method, DNA encoding gc blocking agents are directed into mammalian cells using viral vectors. Furthermore, DNA encoding gc blocking agents may also be introduced into a target cell using a variety of well-known methods that use non-viral based strategies that include electroporation, membrane fusion with liposomes, high velocity bombardment with DNA-coated micro projectiles, incubation with calcium-phosphate-DNA precipitate, DEAE-dextran mediated transfection, and direct micro-injection into single cells. For instance, a plasmid encoding a gc blocking agent of the invention may be introduced into a tumor cell by calcium phosphate coprecipitation (Pillicer et al., *Science,* 209: 1414–1422 (1980); mechanical microinjection and/or particle acceleration (Anderson et al., *Proc. Nat. Acad. Sci. USA,* 77: 5399–5403 (1980); liposome based DNA transfer (e.g., LIPOFECTIN-mediated transfection-Fefgner et al., *Proc. Nat. Acad. Sci., USA,* 84: 471–477 (1987), Gao and Huang, *Biochem. Biophys. Res. Comm.* 179: 280–285, 1991); DEAE Dextran-mediated transfection; electroporation (U.S. Pat. No. 4,956,288); or polylysine-based methods in which DNA is conjugated to deliver DNA preferentially to liver hepatocytes (Wolff et al., *Science,* 247: 465–468 (1990), Curiel et al., *Human Gene Therapy* 3: 147–154 (1992). Each of these methods is well represented in the art. Once introduced into a target cell, DNA sequences can be identified by conventional methods such as nucleic acid hybridization using probes comprising sequences that are homologous/complementary to the inserted sequences of the vector. In another approach, the sequence(s) may be identified by the presence or absence of a "marker" gene function (e.g., thymidine kinase activity, antibiotic resistance, and the like) caused by introduction of the expression vector into the target cell. For instance, if a polynucleotide encoding a gc blocking agent of the invention is inserted into a vector having a dominant selectable marker gene such as a neomycin phosphotransferase gene under separate control of an SV40 early promoter, the sequence can be identified by the presence of the marker gene function (Geneticin resistance). Other methods of detecting the appropriate vector (e.g., PCR methods) will be readily available to persons having ordinary skill in the art. The effect of transfection with DNA encoding a gc blocking agent of the invention may be tested in vitro using any one of a number of readily available cytokine responsive cell lines. Each of these cell lines may be transfected with the appropriate plasmid and the effect of transfection on cell growth and cellular morphology may be tested using procedures described herein.

The state of the relevant gene therapy art is sufficiently advanced so that viral vectors have been employed with dramatic success in in vivo gene therapy experiments. One such vector is the adeno-associated virus (AAV). In AAV vectors, the entire AAV except for the inverted terminal repeats (ITRs) can be deleted and recombinants generated by insertion of the therapeutic gene between the ITRs. AAV vectors have been the subject of previous reviews (Flotte and Carter (1995) *Gene Therapy* 2, 357–362). Landmark issued patents include Carter and Tratschin (number 4,797, 368; issued Jan. 10, 1989) which teaches the use of AAV vectors having a foreign gene driven by an AAV transcriptional promoter, and Muzyczka, Hermonat, Berns and Samulski (U.S. Pat. No. 5,139,941; issued Aug. 18, 1992) which teaches AAV vectors using transcriptional promoters other than those derived from AAV.

Experiments initiated in mid-1994 demonstrate long-term high-level gene expression in vivo using AAV vectors. These vectors were found to be non-toxic and non-immunogenic in mice. High level gene expression was shown to persist for at least 1.5 years. Xiao, Li and Samulski *Journal of Virology* 70, 8089–8108 (1996). Since there was no evidence of viral toxicity or a cellular host immune response, these limitations of viral gene therapy, which were described previously in other systems, have been overcome. Kaplitt, et al., *Nature Genetics* 8, 148–153 (1994) describe long-term (up to 4 months) expression of tyrosine hydroxylase in the rat brain following direct intracranial injection using an AAV vector. Expression was highly efficient and the virus is safe and stable. Flotte et al. *Proc. Natl. Acad. Sci. USA* 90, 10613–10617 (1993) report stable in vivo gene expression of the CFTR gene in rabbits using an AAV vector delivered into the lung using a bronchoscope. This work has been extended by the company Targeted Genetics which has taken this same vector into human clinical trials. Fisher et al. *Nature Medicine* 3, 306–312 (1997), reported stable gene expression in mice following injection into muscle of AAV. Again, the virus was safe. No cellular or humoral immune response was detected against the virus or the foreign gene product.

Costlier et al., *Proc. Natl. Acad. Sci. USA* 93, 14082–14087 (1996), show high-level expression of the erythropoietin (Epo) gene following intramuscular injection of AAV in mice. Epo protein was demonstrated to be present in circulation and an increase in the red blood cell count was reported, indicative of therapeutic potential. Other work by this group has used AAV expressing the HSV tk gene as a treatment for cancer. High level gene expression in solid tumors has been described.

Recombinant adenoviruses (AdV) have also been used in the treatment of solid tumors in animal models and in early human clinical trials. Many of these studies used nude mouse/human xenograft models. Some examples of these modeling experiments include Clayman et al. *Cancer Research* 55, 1–6 (1995) who set up a model of human squamous cell carcinoma of the head and neck in nude mice. They found that adenovirus expressing wild type p53 prevented formation of these tumors. Hirschowitz et. al. *Human Gene Therapy* 6, 1055–1063 (1995) introduced human colon carcinoma cells into nude mice. After tumors were established, they injected these tumors directly with adenovirus expressing the *E. coli* cytosine deaminase gene (CD) then administered 5-fluorocytosine (5FC) systemically (CD plus 5FC is a enzyme/pro-drug combination similar to tk plus GCV). They observed a 4 to 5-fold reduction in tumor size. Zhang et al. *Proc. Natl. Acad. Sci USA* 93, 4513–4518 (1996) formed human breast tumors in nude mice. These tumors were injected directly with adenovirus expressing interferon-alpha. They observed tumor regression in 100% of the animals. Ko et al. *Human Gene Therapy* 7, 1683–1691 (1996) formed human prostate tumors in nude mice and found that direct intratumoral injection of adenovirus expressing wild type p53 inhibited tumor growth. All treated mice remained tumor free for at least 12 weeks after the cessation of treatment. Bischoff et al. *Science* 274, 373–376 (1996) formed human cervical carcinoma and glioblastoma tumors in nude mice. They treated these mice with an adenovirus which had a deletion of the E1B gene. In the absence of E1B, adenovirus selectively kills p53-deficient tumor cells. When injected directly into the tumors, this adenovirus caused tumor regression in 60% of the animals. Ohwada et al. *Human Gene Therapy* 7, 1567–1576 (1996) injected human colon carcinoma cells into the liver of nude mice to mimic liver metastases of colon cancer. They then injected adenovirus expressing CD into the liver near the tumor. Systemic 5FC treatment suppressed tumor growth in these animals. Bramson et al. *Human Gene Therapy* 7, 1995–2002 (1996) injected adenovirus expressing the cytokine IL-12 directly into endogenous mouse breast tumors. The majority of mice had regression of the tumors, and ⅓ remained tumor free after an extended period of time.

Retrovirus vectors were the first vectors used in human gene therapy clinical trials. Roth et al. *Nature Medicine* 2, 985–991 (1996) generated recombinant retrovirus which expressed the wild type p53 gene. This virus was introduced into nine human patients having non-small cell lung carcinoma by direct intratumoral injection using a needle inserted in a bronchoscope. Of the nine patients, three displayed tumor regression while three other patients showed stabilization of tumor growth. No clinically significant vector-related toxicity was noted.

D. Modulation of Th Activity: Methods for Inhibiting T cell Responsiveness

This invention includes compositions and methods for inhibiting antigen-specific T cell responses which are particularly useful in therapeutic situations in which it is desirable to block the generation or to decrease the magnitude or duration of a T cell response. "Inhibition of T cell responsiveness" refers to a reduction in T cell proliferation, or in lymphokine secretion, or in the induction of effector functions by a T cell upon exposure to an antigen. Examples of such therapeutic situations include autoimmune or allergic disease, and transplants of allogeneic or xenogeneic cells or tissue, such as a bone marrow or other organ transplant.

In one embodiment of the invention, T cell responses are inhibited by administration to a subject of a pharmaceutical composition which includes a gc chain blocking agent, so that the composition is present in the subject at the time of stimulation by an antigen. Examples include the administration of such a composition to a subject before homologous tissue transplantation, at the time of an autoimmune flare, or at the time of exposure to an allergen. Accordingly, the method of this invention will inhibit rejection of transplanted tissue and reduce symptoms of autoimmune and allergic disease associated with an undesired immune response.

One can determine, using well established animal models of immunological disease predictive of efficacy in man, whether or not a compound is able to inhibit T cell responses and thereby reduce the advancement, severity or effects of immunological diseases. Agents which inhibit the function of gc chain in a mammal may be tested so that an agent which inhibits the function of human gc chain in vitro can be tested in a small animal model. These models may include, but are not limited to, models of immunological disease in rats, guinea pigs and mice. Examples include autoimmune models such as experimental autoimmune encephalomyelitis, lupus, collagen arthritis, diabetes mellitus, allergen-induced airway hyper-responsiveness, graft rejection or GVHD and delayed type hypersensitivity responses. The ability to inhibit T cell responses can be readily determined by the ability to diminish or delay the disease incidence, severity, or duration, measured according to parameters established for these animal models well known to one of skill in the art. The ability to inhibit T cell responses may be observed during and after the period of administration of the gc-blocking agent.

Animal models of delayed type hypersensitivity (DTH) are particularly useful for addressing the ability of gc chain blocking agents to inhibit T cell responses in vivo. DTH is an immune reaction initiated by antigen-sensitized T lymphocytes responding upon reexposure to specific antigen by the release of lymphokines and/or by the development of specific cytotoxicity, without the participation of free antibody. Locally, it is manifested by the infiltration of cells at the site where antigen is injected. Experimental induction of DTH can be achieved by sensitization and challenge with specific antigen according to methods well known to those of skill in the art (Godfrey and Gell, *Rev. Physiol. Biochem. Pharmacol.* 84:1–92 (1978) and references therein). Antigens which may be employed include soluble proteins, contact sensitizing agents, antigen-antibody complexes, heterologous red blood cells, histoincompatible cells or grafts of histoincompatible tissue. The effects of dose, the use of adjuvant, and different routes of immunization at the sensitization phase and the time interval between sensitization and challenge have been studied extensively. The DTH response can be manifested as a local skin reaction upon challenge with specific antigen by subcutaneous or intradermal injection which is measurable by swelling at the site of challenge and by a histological picture of cellular infiltration. Thus using well established methods, one can readily determine whether or not a gc chain blocking agent is able to inhibit the generation of the DTH response. The gc chain blocking agent may be administered at the time of sensitization and/or at the challenge phase.

Given the primary role of antigen-presenting cells and T cells in the generation of DTH responses, it is well recognized that the rejection of foreign tissue, of organ transplants or of tumors is as much a form of DTH as are DTH skin reactions (Brent et. al., *Lancet* 1958/II, 561–564; Merrill et. al., *J. Clin. Invest.* 40:631–635 (1961). Likewise, the basic cell-mediated responses underlying the generation of DTH, also commonly referred to as TH1 type immune responses underlay many autoimmune diseases including, but not limited to, multiple sclerosis, insulin-dependent diabetes mellitus, rheumatoid arthritis, and inflammatory bowel disease.

The ability of gc chain blocking agents to inhibit T cell responses in vivo also can be readily determined by one of skill in the art using well established animal models of human disease. For eg., animal models of multiple sclerosis, of rheumatoid arthritis, of asthma, of inflammatory bowel disease have been established in a variety of species.

Animal models of multiple sclerosis can be induced in mice, rats, guinea pigs, and monkeys by immunization with a homogenate of central nervous system tissue, with myelin basis protein, proteolipid protein, myelin oligodendrocyte glycoprotein, and a variety of peptides derived therefrom (reviewed in Olsson, *Immunol. Rev.* 144:245–268 (1995); Gerritse et. al., *Proc. Natl. Acad. Sci.* 93:2499–2504 (1996); Miller et. al., *Immunity* 3:739–745 (1995); Yu et. al., *J. Exp. Med* 183:1777–1788 (1996); Kent et. al., *J Neuroimmunology* 58:1–10 (1995). Alternatively, this T cell dependent disease may be induced in a healthy animal by passive transfer of T lymphocytes from an animal immunized with one of the above (reviewed in Olsson, *Immunol. Rev.* 144:245–268 (1995); Perrin et. al., *J. Immunol.* 154:1481–1490 (1995); Yednock et. al., *Nature* 356:63–66 (1992); Baron et. al., *J. Exp. Med.* 177-57-68 (1993). The ability of a gc chain blocking agent to inhibit disease onset, incidence, and severity can be assessed by monitoring of animals for clinical signs of disease on a daily basis for at least 3 weeks post disease induction using a well established scoring system. The gc chain blocking agent may be administered at the time of disease induction or a various times post induction and inhibition of clinical symptoms or reversal of clinical symptoms measured. In some experimental models, a pattern of relapsing/remitting disease is established, allowing one also to assess the effect of a blocking agent on incidence and severity of clinical relapses (Yu et. al., *J. Exp. Med* 183:1777–1788 (1996); McRae et. al., *J. Neuroimmunology* 38:229–240 (1992); Kovarik et. al. *Int. J. Immunopharmac.* 17:255–263 (1995); Suckling et. al., *J. Clin. Lab. Immunol.* 21:173–176 (1986). Further evidence for the effect of a gc blocking agent on the course of disease can be obtained by histological assessment of brain tissue obtained upon sacrifice of the animals and by magnetic resonance imaging. In addition, one can readily perform immunological assays which quantify T cell reactivity to CNS components. Such immunological assays include the ability of animals to mount a DTH response upon challenge with CNS-derived proteins or peptides, and the ability of isolated T cells to respond as measured by proliferation and cytokine production in vitro when exposed to CNS-derived proteins or peptides.

Animal models of rheumatoid arthritis have been established and characterized in a variety of species, including mice, rats and non-human primates. Experimental models of arthritis with clinical and histopathological features similar to those in humans can be induced by a variety of agents, including infectious agents or their components such as the mycobacteria contained in complete Freund's adjuvant, and major protein components of cartilage such as collagen II and proteoglycans (reviewed in Wooley, *Current Opinion in Rheumatology* 3:407–420 (1991); Taurog et. al., *Methods in Enzymology* 162:339–355 (1988); Ridge et. al., *Methods in Enzymology* 162:355–373 (1988). In particular, the murine model of collagen-induced arthritis induced by immunization of the DBA/1J strain of mice with bovine collagen has been employed widely given key features shared with the human disease state, i.e. susceptibility to disease is genetically linked to the Major Histocompatibility Complex, reactivity to collagen is observed, and both T cell and B cell components appear to contribute to the disease state (Staines and Wooley, *British Journal of Rheumatology* 33:798–807 (1994); Holmdahl et. al., *Clinical and Experimental Rheumatology* 7/S-3:51–55 (1989). In addition, this model has been employed extensively for the evaluation of T cell inhibitory agents (Staines and Wooley, *British Journal of Rheumatology* 33:798–807 (1994). Such models may be established readily by one of skill in the art and employed to assess the inhibitory activity of gc chain blocking agents. The protective effect of a gc chain blocking agent may be readily assessed by administration of this agent according to one of a variety of regimens, for e.g. starting at the time of disease induction or at various times post induction. The onset, incidence and severity of disease may be quantified by daily monitoring of the animals for at least 6 weeks using a well established scoring system. In addition, joint tissue may be examined histologically in order to assess tissue injury as a measure of disease progression. In the case of collagen-induced arthritis, other assays well known to one of skill in the art also may be employed to evaluate the protective effect of a gc chain blocking agent including the analysis of the serum antibody response to collagen, in particular T cell dependent anti-collagen antibodies of the IgG2a subclass which are closely associated with disease incidence, and T cell reactivity in vitro as measured by proliferation in response to collagen.

Experimental models of allergen-induced airway hyperreactivity have been routinely employed as models of allergic disease and asthma. Models of airway hyperreactivity have been established by sensitizing animals with protein antigens administered as aerosols or by a systemic routes, e.g. intra peritoneally or subcutaneously in the adjuvant aluminum hydroxide (Renz et. al. *International Archives of Allergy and Immunology* 109:167–176 (1996); Nakajima et. al., *Am Rev Respir Dis.* 146:374–377 (1992); Krinzman et. al., *J. Clin. Invest.* 98:2693–2699 (1996); Henderson et. al., *J. Exp. Med.* 184:1483–1494 (1996); Pretolani et. al., *J. Exp. Med.* 180:795–805 (1994). Lung hyperreactivity is then elicited upon secondary exposure to the antigen in an aerosolized form. The development of allergen-induced lung hyperreactivity is highly dependent upon IL-4 production by T cells of the TH2 type (Renz et. al. *Interational Archives of Allergy and Immunology* 109:167–176 (1996). One may use protocol designs and assays well known to those of skill in the art in order to determine whether or not a gc chain blocking agent is protective in this setting, a gc chain blocking agent may be administered at the time of sensitization, just before challenge, and/or at the challenge phase. It may be administered by aerosol or systemic routes, as a single exposure or by a repeated treatment course. Lung function may be assessed by measuring airway responsiveness to inhaled methacholine using barometric whole body plethysmography. In addition, a variety of immunological assays may be employed in order to assess inhibitory activity of a particular treatment. These assays include but are not limited to the following. Cellular infiltration into the lung can be measured by quantifying the cell number and cellular composition present in bronchial alveolar lavage (BAL) fluid. In particular, eosinophil content should be evaluated. T cell reactivity can be evaluated by measuring the proliferative response when exposed to the specific antigen in vitro. In addition, T cell reactivity may be assessed by measuring IL-4 and IL-5 production upon exposure to antigen in vitro. It is well known to those of skill in the art that the contribution of B cells to the hyperreactive response can be measured by quantifying T cell dependent serum IgE and IgG1 production in response to the specific antigen.

Animal models of inflammatory bowel disease (IBD) are well known to those of skill in the art, as reviewed by Grisham (*Current Opinion Gastroenterology* 9:524–533 (1993), Powrie (*Immunity* 3:171–174 (1995) and Elson et. Al. (*Gastroenterology* 109:1344–1367 (1995), a feature common to many of these models appears to be the critical role played by the T cell in regulating intestinal immune responses. These models may be employed to determine whether or not a gc chain blocking agent inhibits the disease state using well established protocol designs and assays. For eg., see Powrie et. al., *Immunity* 1:553–562 (1994), Murthy et. al., *Digestive Disease and Sciences* 38:1722–1734 (1993), Miller et. al., see *Gastroenterology* 109:1475–1483 (1995) and *J. Pharmacology and Experimental Therapeutics* 266:468–472 (1993). Clinical symptoms routinely monitored include weight loss, diarrhea and bloody stool. Changes in one or more of these parameters with treatment by a gc chain blocking agent could readily be established. In addition, histological assessment of bowel tissue may include the morphological changes, i.e. crypt hypertrophy, mucosal and submucosal fibrosis, the degree of cellular infiltration, myeloperoxidase content as a measure of granulocyte infiltration, production of nitric oxide (NO) and presence of products of NO such as nitrotyrosine as detected by immunohistochemical methods (Miller et. al., *J. Pharmacology and Experimental Therapeutics* 266:468–472 (1993); Miller et. al., *Gastroenterology* 109:1475–1483 (1995).

E. Methods for Inducing T Cell Unresponsiveness

This invention includes compositions and methods for modulating antigen-specific T cell unresponsiveness. The terms "T cell unresponsiveness" and "T cell anergy" are used interchangeably herein. The methods of this invention provide a means for inducing or maintaining unresponsiveness of a T cell to an antigen in vitro or in vivo.

In one embodiment of the invention, T cell unresponsiveness or anergy is induced by exposing a T cell to an antigen-specific signal in the presence of a gc chain-blocking agent. Agents which inhibit stimulation of the T cell through a cytokine receptor may result in complete or partial blocking of T cell stimulation through that cytokine receptor on the T cell surface thereby resulting in a reduction or lack of response upon re-exposure to the specific antigen in the absence of the gc-blocking agent.

In one method of this invention, T cell unresponsiveness is induced by administration to a population of T cells a composition which includes a gc chain-blocking agent, such as a gc chain-blocking antibody, so that the composition is present at the time of exposure to an antigen. This method is particularly useful in therapeutic situations where it is desirable to induce an antigen-unresponsive state. Examples of such include the administration of such a composition to a subject before homologous tissue transplantation, at the time of an autoimmune flare, or at time of exposure to an allergen. In another embodiment of the invention, T cell anergy is induced in vitro by exposure of T cells contained in donor tissue (e.g., bone marrow) to cells of a recipient in the presence of a composition containing gc chain-blocking agent. This method is effective to decrease the incidence or severity of graft versus host disease. Accordingly, the method of this invention will inhibit rejection of transplanted tissue and reduce symptoms of autoimmune and allergic disease associated with an undesired immune response.

One can determine, using well established animal models of immunological disease predictive of efficacy in man such as those cited above, whether or not a compound is able to induce T cell unresponsiveness. This ability can be assessed by a reduction on disease incidence, severity or duration, or the lack thereof, both during and after the period of treatment with a gc-blocking agent. According to this method, the effect is also maintained upon re-exposure of the animal to the disease-inducing agent, such as an antigen or the presence of grafted cells or tissues, at a time when the gc-blocking agent is no longer detectable in the host animal.

F. Methods for Maintaining T Cell Unresponsiveness

In another embodiment, T cells in which unresponsiveness or anergy has been previously induced or established, such as by exposure to an antigen in the absence of a costimulatory signal, could be exposed to the gc chain-blocking agent for maintenance of an unresponsive state. This aspect of the invention is particularly useful in situations in which it is desirable to establish and preserve the antigen-unresponsive state. Examples include autoimmune disease, allergic disease, and transplants of allogeneic or xenogeneic cell or tissue, such as a bone marrow or other organ transplant. In these situations, a therapeutic regimen may have induced a state of antigen-specific T cell unresponsiveness in the subject. For example, antigen-specific T cell unresponsiveness may have been induced in a subject by inhibiting a cotsimulatory signal in T cells, such as occurs with an agent which blocks the interaction of CD28 or CTLA-4 with a CD28/CTLA-4/ligand, such as CTLA-4 Ig (Turka et al., *Proc. Natl. Acad. Sci. USA* 89:11102–11105 (1992); Lenschow et al., *Science* 257:789–792 (1992)) or with a gc chain blocking agent (see above).

In this embodiment of the invention, unresponsiveness of a T cell to an antigen is maintained by contacting the T cell with an agent, such as a gc chain blocking antibody, which inhibits stimulation of the T cell through gc chain-encompassing cytokine receptors. Agents which inhibit stimulation by binding to gc chain may result in complete or partial inhibition, so long as it is sufficient to maintain T cell unresponsiveness as defined herein. In one embodiment of the invention, T cell unresponsiveness is maintained to an antigen on an allogeneic or xenogeneic cell. Accordingly, the method of the invention can be used to treat a subject who is a recipient of the allogeneic or xenogeneic cell, for example an organ transplant recipient, and is useful for inhibiting either rejection of transplanted tissue or graft vs. host disease in a subject. In another embodiment of the invention, T cell unresponsiveness is maintained to an autoantigen or to an allergen. Accordingly, the method of the invention can be used to treat a subject suffering from an autoimmune or an allergic disease, and is useful for alleviating the symptoms of those disorders associated with an inappropriate or undesired immune response. The gc chain blocking agent employed to maintain T cell unresponsiveness in these therapeutic situations may be administered subsequent to application of the agent used to induce T cell unresponsiveness. Where the agent used to induce T cell unresponsiveness is an agent other than a gc chain blocking antibody, such as CTLA-4 Ig, the gc chain blocking agent can be administered simultaneously with the inducing agent.

In another embodiment of the invention, T cell unresponsiveness is induced or maintained to an antigen on an allogeneic or xenogeneic cell. Accordingly, the method of the invention can be used to treat a subject who is a recipient of the allogeneic or xenogeneic cell, for example an organ transplant recipient or a bone marrow transplant recipient. The method of the invention is thus useful for inhibiting transplant rejection and graft versus host disease in a subject.

In another embodiment of the invention, T cell unresponsiveness is induced or maintained to an autoantigen. Accordingly, the method of the invention can be used to treat a subject suffering from an autoimmune disease or a disorder associated with an immune response.

G. Methods for Differential Modulation of Th1 versus Th2 Immune Activities

One aspect of this invention pertains to methods for selectively treating Th1- and Th2-based pathologies. Examples of Th1-based pathologies include organ-specific and systemic autoimmune conditions, chronic cell-mediated inflammatory conditions, cellular rejection of transplanted cells or tissue, and graft vs. host disease. Examples of Th2-based pathologies include antibody-mediated disorders, including allergic rhinitis, asthma and excema.

In one embodiment of the invention, a pharmaceutical composition which includes gc chain blocking agent which differentially modulates Th1 vs Th2 immune activity is administered to a subject, so that the composition is present in the subject at the time of exposure to an antigen. Examples might be the administration of such a composition to a subject before homologous tissue transplantation, or at the time of exposure to an allergen. In another embodiment of the invention, the pharmaceutical composition is administered at the appearance of symptoms associated with an inappropriate or undesired immune response, such as an autoimmune flare. The gc chain blocking agent thereby inhibits the rejection of transplanted cells or tissue and alleviates symptoms of autoimmune or allergic disease associated with undesired immune responses.

In another embodiment of the invention, a Th1 response is selectively modulated in vitro by exposure of T cells contained in donor tissue, such as bone marrow tissue, to cells of the recipient in the presence of a pharmaceutical composition containing gc chain-blocking agent, to decrease the incidence or severity of graft versus host disease.

One can determine, using well established animal models of immunological disease predictive of efficacy in man whether or not a compound is able to selectively modulate Th1 but not Th2 based pathologies, or vice versa. The ability to gc-blocking agents to reduce incidence, severity or duration of Th1 based responses may be determined using models such as experimental autoimmune encephalomyelitis, collagen-induced arthritis, diabetes mellitus, graft rejection, GVHD and delayed type hypersensitivity responses, many of which are established in rats, mice and guinea pigs. The ability of gc-blocking agents to reduce incidence, severity or duration of Th2 based responses may be determined using models such as allergen-induced airway hyper-responsiveness and the induction of IgE responses also established in rodent models.

H. Use of gc blocking Agents as Noncompetitive Inhibitors of Cytokine Receptor Function Our experiments and calculations suggest that, even at saturating concentrations of cytokine, the binding interaction between gc chain and the binary or ternary complex of cytokine with other receptor chains remains of low affinity (See Example 4). This further suggests that an antagonist that binds to gc and prevents it from participating in the receptor complex will not be in direct competition with the high-affinity binding of cytokines to cells and that noncompetitive inhibitors which block the formation of the signaling complex without directly competing against the binding of the natural ligand are possible. Indeed, we have identified the gc-directed CP.B8 mAb as just such a noncompetitive inhibitor of both IL-4 and IL-2-dependent proliferation of T cells (Example 4).

The potential advantages of noncompetitive inhibitors over competitive inhibitors which target high affinity cytokine binding sites are as follows:

1. a gc directed or other noncompetitive inhibitor of a cytokine receptor (e.g., IL-4R) is not in competition with the high affinity binding of cytokines to the cells. Such an inhibitor therefore needs only a sufficient affinity for its target (e.g., gc chain) to bind and sequester a sufficient fraction of that target and prevent it from participating in the formation of a signaling complex. This is not true for a competitive inhibitor, for which $IC_{50}=K_D (1+[\text{cytokine concentration}]/K_{D(cytokine)})$. Because a competitive inhibitor is in direct competition with the high affinity binding of the natural ligand, it may therefore require concentrations of inhibitor that are orders of magnitude higher than its $K_D$ for binding in order to produce inhibition in the presence of competing ligand.

2. For a competitive inhibitor, inhibition may be weak or nonexistent in the presence of high local concentrations of the natural ligand, such as might occur in restricted compartments of the body. In addition, inhibition at a given dose of inhibitor can potentially be overcome by a local up-regulation of the cytokine concentration. In contrast, the degree of inhibition achieved by a given concentration of a noncompetitive inhibitor is essentially insensitive to variations in cytokine concentration.

I. Pharmaceutical Use of the Compounds of the Invention

For use in treating a subject, a safe and effective amount of a compound of the invention is administered. By "safe and effective amount" is meant that amount which provides therapeutic efficacy at a reasonable benefit/risk ratio, as is attendant with any medical treatment, a gc chain blocking agent is administered to subjects in a biologically compatible form suitable for pharmaceutical administration in vivo, in an amount and for a time sufficient to modulate T cell responses, such as to inhibit Th cell responses, or to induce or maintain T cell unresponsiveness in the subject. By "biologically compatible form suitable for administration in vivo" is meant a form of the gc chain blocking agent to be administered in which toxic effects are outweighed by the therapeutic effects of the agent. Administration of a gc chain blocking agent as described herein is in a pharmacological form including a therapeutically active amount of agent alone or in a pharmaceutically acceptable carrier. Administration of a therapeutically active amount of the gc chain blocking agent is defined as an amount effective, at dosages and for periods of time necessary to achieve the desired result. The amount of the compound or composition which is administered will vary with such factors as a patient's age, medical status, weight, sex, and concurrent treatment with other pharmaceuticals.

The term "subject" used herein is taken to mean any mammalian patient to which therapeutics may be administered. Subjects specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts. Cells may be in any form, including but not limited to cells retained in tissue, cell clusters, immortalized, trasfected or transformed cells, and cells derived from an animal that have been physically or phenotypically altered.

The compounds of the invention may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical, a compound of the invention can be administered to a subject for therapeutic purposes, such as to inhibit rejection of an organ or bone marrow transplant, to inhibit graft versus host disease in bone marrow transplantation or to treat an autoimmune disease in a subject. The compounds and compositions of the invention are administered to treat various diseases involving the action of T-helper cells. Such diseases include a broad range of immunological diseases, as previously cited.

Dosage regimens may be adjusted to provide the optimum therapeutic response. For example, several divided doses may be administered daily or the dose may be proportionally reduced as indicated by the exigencies of the therapeutic situation.

The timing of administration of an anti-gc agent can be coordinated with administration of other therapeutic agents to a subject. For example, for maintaining T cell unresponsiveness in a subject induced by an agent which inhibits a T cell costimulatory signal in the subject (e.g., CTLA4Ig), an anti-gc agent can be administered simultaneously with the agent which inhibits a T cell costimulatory signal or subsequent to administration of the agent which inhibits a T cell costimulatory signal. Alternatively, where an anti-gc agent is maintained at an effective level in vivo, the anti-gc agent can be administered prior to administration of the agent which inhibits a T cell costimulatory signal. Alternatively, an anti-gc agent can be administered as an adjunct to other common therapeutic treatments used to inhibit an immune response against an antigen. For example, an anti-gc agent can be administered as part of a therapeutic regimen that includes administration of an immunosuppressive drug such as cyclosporin a or FK506.

The compounds of the invention are formulated in a manner consistent with appropriate medical practice. Typically, the compounds may be stored either in solution or in an anhydrous state such as lyophilized, or in any other state which preserves the activity of the compounds.

The compound of the invention may be administered in a convenient manner such as by injection (subcutaneous, intravenous, etc.), oral administration, inhalation, transdernal application, or rectal administration. Depending on the route of administration, the active compound may be coated in a material to protect the compound from the action of enzymes, acids and other natural conditions which may inactivate the compound.

To administer a compound of the invention by other than parenteral administration, it may be necessary to coat the agent with or co-administer the agent with a material to prevent its inactivation. For example, a compound of the invention may be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropyl-fluorophosphate (DEP) and trasylol. Liposomes include water-in-oil-water emulsions as well as conventional liposomes. See Strejan et al., J. Neuroimmunol 7:27 (1984)).

The compounds may be formulated with a pharmaceutically-acceptable carrier or diluent, which is any carrier which is relatively non-toxic and innocuous to a patient at concentrations consistent with the effective activity of the active ingredient so that any side effects ascribable to the carrier do not vitiate the beneficial effects of the active ingredient. The carrier must also be compatible with the other ingredients of the formulation. The term "compatible", as used herein, means that the components of the pharmaceutical compositions are capable of being commingled with the compound of the present invention, and with each other, in a manner such that there is no interaction which would substantially reduce the pharmaceutical efficacy of the pharmaceutical.

Pharmaceutical compositions suitable for injectable use include sterile aqueous solutions (where water soluble) or dispersions and sterile powders for the extemporaneous preparations of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water ethanol, polyol (for example, glycerol, propylene glycol, and liquid polyethylene glycol, and the like), and suitable mixtures thereof. The proper fluidity can be maintained, for example, by the uses of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., a compound of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., compound of the invention) plus any additional desired ingredient from a previously sterile-filtered solution thereof.

When the active compound is suitably protected, as described above, an agent may be orally administered, for example, with an inert diluent or an assimilatable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Containers for the compounds and compositions of the invention include any which will maintain these compounds and compositions in a condition suitable for medical administration to a subject. Such containers might include single or multi-use vials, prefilled syringes, or bags or other containers suitable for providing intravenous fluids to a subject. The containers might be packaged with instructions for appropriate medical use, which is any medically acceptable indication and administration regime, as would be known to one of skill in medical arts.

Deposits

Murine hybridoma cells and anti-gc antibodies useful in the present invention are exemplified by cultures deposited under the Budapest Treaty with the American Type Culture Collection, 10801 University Boulevard, Manassas, Va. 20110-2209 on May 10, 1996 and identified as:

| Hybridoma Designation | ATCC Accession Number |
|---|---|
| AF.F4 | HB-12104 |
| CQ.C11 | HB-12105 |
| AE.C9 | HB-12106 |
| CP.B8 | HB-12107 |

The following, non-limiting examples are designed to more particularly point out the features of the present invention.

EXAMPLE 1

Generation of Murine Anti-Human gc Specific mAbs.

The immunogen used to generate murine anti-human gc specific InAbs is a novel, recombinant soluble fusion construct comprising the two ectodomains of the gc chain fused at the 3' end to human immunoglobulin constant region sequence, namely the Hinge, CH2 and CH3 region sequences, and bound to Protein a Sepharose beads as described below.

a. Construction of plasmid encoding a gc-Ig fusion protein.

The full length human gc chain cDNA is cloned from a cDNA library made from the Jurkat T cell line, with cDNA flanked by BstX-1/Not-1 adaptors cloned into the BstX-1 site of the pCDM8 vector (Seed, *Nature* 329:840–842 (1987)). This library is screened with an antisense oligonucleotide probe corresponding to nucleotide 592–620 of the published sequence (*Science* 257:379–382, 1992). Clones which hybridize to the oligonucleotide probe are identified and the DNA sequence of these candidates obtained. Clone p4A1 contains a Not-1 insert (1531 bp) encoding the full length human gc chain cDNA sequence and is used for constructing the Ig fusion protein.

The DNA sequence of clone p4A1 is 65 base pairs longer at the 5' end than the 5 published cDNA sequence (*Science* 257:379–382, 1992) and presumably represents additional 5' untranslated region since it is upstream of the translation initiation codon. There is a single nucleotide difference between the published sequence and clone p4A1, within the coding region. There is a C at NT 673 of the published sequence (Takeshita et. al., *Science* 257:379–382 (1992) whereas in clone p4Ai the corresponding base is a T. Thus the protein encoded by p4A1 contains a methionine at position 220 instead of a threonine. This is within the extracellular domain and is present in the fusion protein, a gc chain-Ig fusion protein is constructed by PCR of gc chain extracellular sequence from the template plasmid p4A1. The following PCR primers are used: 5' primer 310–045 (SEQ ID NO: 7) 5'-AACTGCAGCGGCCGCCATGGTGAAGCCATCATT ACC-3' which contains a Not1 cloning site, and 3' primer 310–046 (SEQ ID NO:8) 5'-GACTTTGTCGACATTCTCTT=TGAAGTATTGC-3' which contains a Sal-1 cloning site.

The resultant 789 bp PCR fragment is cut with Not-1 and Sal-1, a 693 bp fragment encoding human IgG1 C sequence is isolated from pSAB144 (disclosed in BGP-151CP/ DO15CIP2) by digestion with Sal-l and Not-i. These fragments are ligated to the pSAB132 expression vector (disclosed in BGP-151CP/DOl5CIP2) which had been cleaved with Not-1. The resultant gc-IgG fusion construct, pLB001 (depicted in FIG. 1) encodes the amino terminal 254 aa of mature gc chain, ten amino acids of the hinge region of human IgG1, and the CH2 and CH3 constant domains of IgGl. The nucleotide sequence encoding the gc-Ig construct is shown in FIG. 18 (SEQ ID NO. 1) and the deduced amino acid sequence in FIG. 19 (SEQ ID NO. 2).

B. Transient Expression of pLB001.

The gc-IgG fusion protein is transiently expressed by COS-7 cells and purified from cell culture supernatant for preparation of the immunogen. For transient expression, 20 ug of pLB001 is electroporated into COS-7 cultured in Modified Eagles Media (Gibco BRL, Life Technologies, Gaithersburg, Md.) and which had been split 24 hours prior to 50% confluency. Electroporation conditions are .28 kV and 960 uFD. Cell culture supernatant is collected 48–72 hours post transfection. Culture supernatant is loaded onto a column of Protein a Sepharose 4B Fast Flow previously washed with Phosphate buffered saline (PBS) –0.2% sodium azide. The column is then washed with 25 mM $H_3PO_4$ pH 5.0, 100 mM NaCl in order to remove any bound bovine IgG. The gc-IgG protein is eluted with 25 mM $H_3PO_4$ pH 2.8 and immediately neutralized with 0.5M $NaPO_4$. This material ran as a band of approximately 184,000 MW on a nonreducing SDS-PAGE gel, and as an band of approximately 87,800 MW under reducing conditions.

C. Monoclonal Antibody Production.

The immunogen comprises purified gc-Ig fusion protein bound to Protein a Sepharose 4B Fast Flow resin. The resin, supplied in 20% ethanol as preservative, is first washed three times with sterile PBS, then pelleted and resuspended in a volume of PBS equal to the starting volume. This slurry and the purified gc-Ig protein are then combined in the following proportions, 100 ul of slurry is incubated with 33 ug of gc-Ig with rocking at room temperature for 1 hour, after which the mixture is further diluted to a total volume of 200 ul with PBS. Each mouse is injected with a total of 33 ug gc-Ig bound to Protein a resin in 200 ul intra peritoneally. Three female RBF mice (4–6 weeks of age) are immunized, and then boosted i.p. every 2 weeks with the same dose of gc-Ig/Protein a beads. After 3 boosts, the mice had a good titer by solid-phase ELISA and immunofluorescent staining assays. (The two assays employed to assess serum activity at this stage are also used as screens for mAb production and are described below). The mice are rested for 1.5 months and the mouse with the highest titer is then boosted 3 days prior to fusion, i.p., with 100 ug gc-Ig/protein a beads and 1 day prior to fusion i.v. with 100 ug soluble gc-Ig.

The fusion is carried out according to standard procedures, essentially as previously described by Lerner, *The Yale Journal of Biology and Medicine* 54:387–402 (1981). The spleen from the boosted mouse is removed and made into a single cell suspension. The spleen cells and the myeloma cells FL653 (Fisher Scientific, Pittsburgh, Pa.) are washed in serum free 3X Dulbecco's Modified Eagles Medium (DMEM) (Gibco BRL, Gaithersburg, Md.) and then pelleted together. The spleen:myeloma cell ratio is 6:1 and the cells are fused with a 50% PEG 3350/DMEM solution at a concentration of 0.8 mls per $2 \times 10^8$ cells in the pellet. After the fusion the pellet is resuspended into selection media, DMEM supplemented with 10% FBS, 10% NCTC 135 (Gibco BRL), $5 \times 10^{-5}$M 2 mercaptoethanol, 2 mM glutamine, 0.1 U/ml bovine insulin, 10% non-essential amino acids, 1 mM oxaloacetic acid, 0.5 mM sodium pyruvate, 2% IGEN® brand Origen Hybridoma Cloning Factor (Fisher Scientific), and AAT selection media (Sigma Chemical Co, St. Louis, Mo.). The cells are then plated out at the following concentrations in 96 well plates: $1 \times 10^5$ cells/well/75 ul, $3.3 \times 10^4$ cells/well/75 ul and $1.1 \times 10^4$ cells/well/75 ul. The plates are incubated at 37 degrees C, 10% CO2. The fusion is fed with 100 ul/well of selection media on day 3 post fusion, and media is removed and replaced on day 7. Colonies appear between 10–14 days after fusion.

D. Screening Assays.

96-Well Corning plates are coated with 50 ul/well of Goat anti-human IgG Fc-specific (Jackson ImmunoResearch, West Grove, Pa.) at 5 ug/ml in bicarbonate buffer (50 mM bicarbonate/carbonate pH 9.6) overnight at 4 degrees C. The coating solution is removed, plates are blocked with 1% normal goat serum and 1% bovine serum albumin (BSA) in PBS for 1.5 hours at room temperature, and plates are then washed with 0.1% Tween in PBS. The antigen, gc-Ig, or a control Ig fusion protein diluted in PBS-1% BSA are added at 1 ug/ml, 50 ul/well and incubated for 1 hour at room temperature. After washing, samples containing antibodies to gc-Ig, eg. antisera or hybridoma culture supernatant, are added. Samples are diluted in PBS-1% BSA containing human IgG (5 ul at 1 mg/ml) in order to provide a decoy for any anti-huIg antibodies. Hybridoma supernatant is routinely diluted 2 fold. Samples are incubated for 1 hour at room temperature, plates washed, followed by detection with Alkaline phosphatase coupled Goat anti-mouse IgG and substrate PNPP according to standard procedures. We also use a standard immunofluorescent staining technique to detect anti-gc specific antibodies which recognizes cell surface gc. Briefly, mouse sera or hybridoma culture supernatant are incubated with a gc expressing cell, eg. a murine L cell stably expressing human gc chain, human PBMC, human lymphoid cell lines are employed. The assay buffer is PBS-1% BSA-0.02% sodium azide. For negative controls we use preimmune sera and supplemented DMEM selection media, respectively. After 30 minutes at 4 degrees C, cells are washed and bound antibody detected with a phycoerythrin-conjugated Goat anti-mouse Ig reagent. A third screening assay is used in order to identify anti-gc mAbs with blocking activity, i.e. the effect of mAbs on inhibition of cytokine-driven cell proliferation (described below). This assay is later used to further define the activity of the purified mAbs. MAb are purified from hybridoma culture supernatants by adsorption to Protein A-Sepharose, the columns then washed in PBS –0.2% sodium azide, and the mAb eluted with 25 mM $H_3PO_4$ pH 5.0, 100 mM NaCl.

Figure 3A:
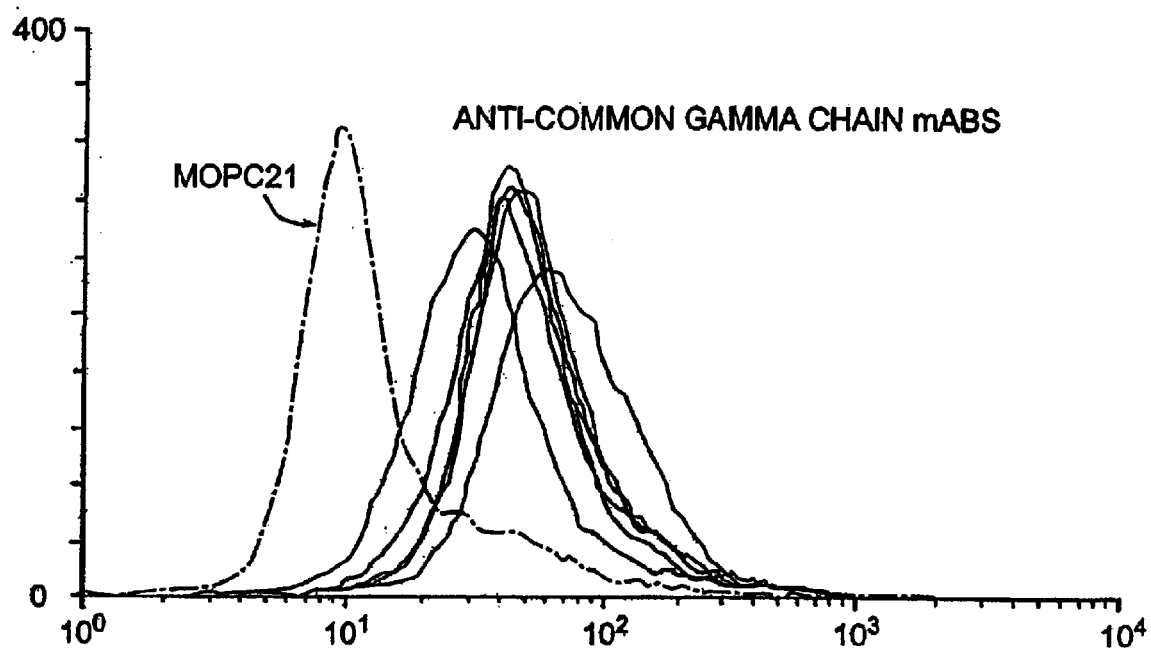
FIG. 3A shows immunofluorescent staining with one set of anti-gc mAbs and FIG. 3B shows staining with different set of anti-gc mAbs.
Figure 3B:
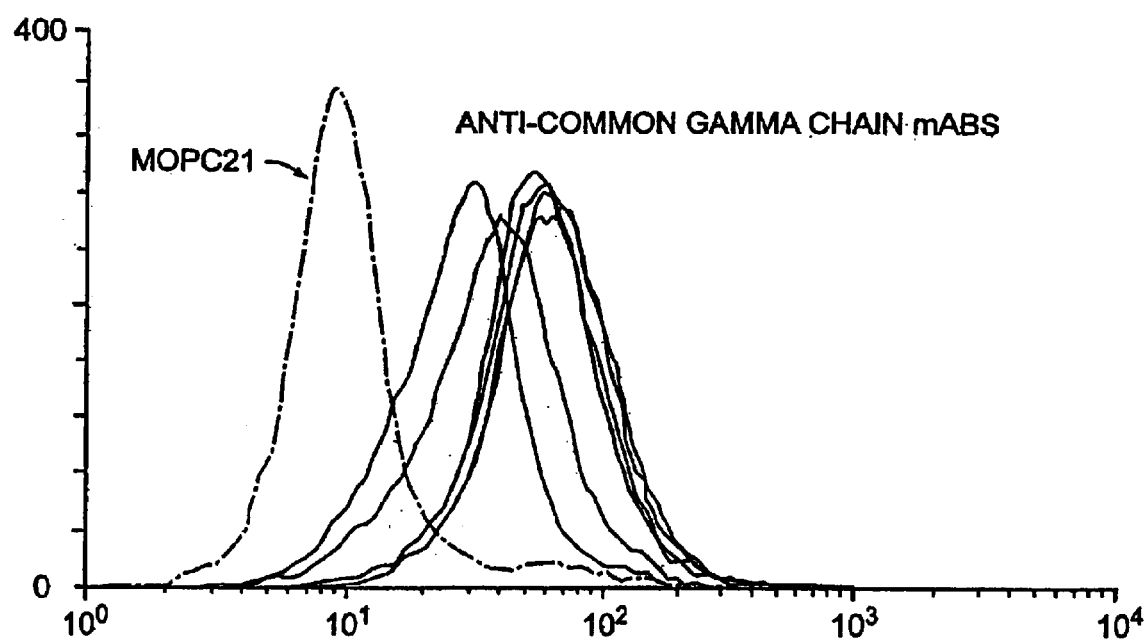

We have generated a panel of anti-human gc chain mAbs by immunizing and screening as described above. Binding of purified mAbs to an L cell transfectant stably expressing human gc chain, but not to the L cell parent was detected by standard immunofluorescent staining, is shown in FIG. 2. These data demonstrate their specificity for human gc chain. These mAbs also recognize gc chain expressed on normal human cells as shown by their binding to PHA-activated PBMC (FIG. 3).

EXAMPLE 2

Cloning of the variable regions for the light and heavy chains of CP.B8

RNA was isolated from the anti-human gc chain hybridoma line (CP.B8) and used for first strand cDNA synthesis. Two micrograms of RNA was converted to cDNA using oligo dT (GibcoBRL Superscript preamplification system). A fraction of the cDNA reaction was used as a template for amplification in a reaction using 6 uM of the light chain variable region primers ACE-149 [5' d(CTGGATATCGTA ATGACCCAGTCTCCA):SEQ ID NO: 9] and ACE-150 [5' d(GTTAGATCTCCAGCTTGGTCCC): SEQ ID NO: 10] or the heavy chain variable region primers VH-01 [5' d(AGGTSMARCTGCAGSAGTCWGG):SEQ ID NO: 11] where S=C/G, M=A/C, R=A/G and W=A/T and VH-02 [5' d(TGAGGAGACGGTGACCGTGGTCCCTTGGCCCC): SEQ ID NO: 12], 0.2 mM dNTPs, 10% DMSO (light chain only), 20 mM Tris-Cl (pH 8.8), 10 mM KCl, 10 mM $(NH_4)_2SO_4$, 2 mM $MgSO_4$, 1.5 mM $MgCl_2$, 0.1% Triton X-100, 100 Install Equation Editor and double-click here to view equation, g/ml BSA, and 1.25 units Pfu polymerase (Stratagene, La Jolla, Calif.) for 30 cycles at 94° C. for 1 min., 50° C. for 2 min. and 72° C. for 2 min. The PCR fragments were isolated from a low melt gel and then cloned using the Pharmacia Sure Clone kit into pNN05. The DNA sequence was determined and compared to the Genbank database where matches to heavy and light variable regions were found. In order to prove specificity of these sequences for the human gc chain, a signal sequence and constant region were cloned adjacent to the variable region fragments and co-transfected into Cos cells. In a FACS analysis, the supernatant from the transfected cells detected the gc chain.

EXAMPLE 3

Inhibitory Activity of Murine Anti-Human gc Specific mAbs

A. Cytokine-Dependent Growth Assays with Human Peripheral Blood Cells

Human peripheral blood mononuclear cells (PBMC) are isolated from freshly drawn blood of normal, healthy donors. Blood is collected in heparinized syringes, diluted two-fold with sterile PBS and the mixture layered over 15 ml of Ficoll-Hypaque in a 50 ml tube at room temperature. Blood is centrifuged for 30 minutes at $400 \times g_{av}$ at room temperature. PBMC are collected from the interface, and resuspended in RPMI supplemented with 10% FBS and 2 mM L-glutamine after 1 wash in PBS. The cells are counted and used in the assays described below.

For some experiments, human PBMC are enriched for T lymphocytes by depletion of the B lymphocyte and Natural Killer (NK) cell subsets using monoclonal antibodies (mAbs) to CD20 and to CD16, respectively. These mAbs are covalently coupled to magnetic particles (PerSeptive Diagnostics, Cambridge, Mass.) and incubated with the PBMC suspension according to the manufacturer's recommendations. PBMC are suspended in RPMI-10% fetal bovine serum at a fmal concentration of $5 \times 10^6$ cells/ml. Anti-CD20 coupled particles (30 particles/cell) and anti-CD16 coupled particles (30 particles/cell) are added, with coupled particles provided at $\sim 5 \times 10^8$ particles/mg. Cells are incubated with magnetic particles for 20–30 minutes rotating at 4 degrees C, and mAb-bound B cells and NK cells then separated by applying a magnetic field along the side of the cell culture tube perpendicular to gravity for a 5–10 minute period at room temperature, causing cells bound to the magnetic beads to collect at the sides of the vessel. The T cells which remain in suspension are collected by aspirating and transferring the media to a fresh tube. Immunofluorescent staining of the resultant population for different cell subsets using mAbs to detect T cells (anti-TcR, anti-CD4 and anti-CD8 mAbs), B cells (anti-CD20), NK cells (anti-CD16 and anti-CD57 mAbs) demonstrate that this population is enriched for T lymphocytes (about 95% TcR+ cells).

The PBMC or enriched T cell population is polyclonally stimulated with Phytohemagglutinin (PHA) by culturing $1 \times 10^6$ cells/ml with 1 ug/ml PHA for 4 days at 37 degrees C in a humidified incubator with 5% $CO_2$. Culture media is RPMI/10% FBS/2 mM L-glutamine/$5 \times 10^{-5}$ M 2-mercaptoethanol and antibiotics, with 10–15 ml volume per 10 cm petri dish. After 4 days, T cell blasts are harvested, washed three times with RPMI-10% FBS and replated in 96-well plates at $1 \times 10^6$ cells/ml ($5 \times 10^4$ cells /well) in the presence or absence of a source of anti-human gc antibodies, bringing the culture volume up to a total of 100 ul. Hybridoma supernatant (¼ dilution) or purified mAbs (0.1–100 ug/ml) are used. After a 30–45 minute preincubation with mAb at 37 degrees, an exogenous source of T cell growth factor is added to sustain the growth of the blasted cells. Recombinant T cell growth factors employed are IL-2 (R & D Systems, Minneapolis, Minn.), IL-4 (BioSource, Camarillo, Calif.) or IL-7 (Genzyme, Cambridge, Mass.), generally at a concentration of 1.1 ng/ml–3.3 ng/ml unless otherwise specified, added in a volume of 100 ul to bring the total microculture volume up to 200 ul. Concentrations of 1.1–3.3 ng/ml of exogenous growth factor generally support 50–80% of the maximal growth response, i.e. provide at least the 50% stimulatory dose. Cells are cultured with growth factor for 1.5–2 days, with growth measured by the incorporation of $H^3$-thymidine added during the final 8–16 hrs. of culture. 2 $\mu$Ci of $H^3$-thymidine is added in 50 ul to each well. Cultures are harvested onto Tomtec Harvester 96 Wallac filtermats, Wallac liquid scintillation cocktail added and cpm/well determined with an 1205 Betaplate Reader (Pharmacia LKB, Gaithersburg, Md.). Background cpm is defined by culturing cells in the absence of exogenous growth factor, where there is a low level of proliferation given little endogenous cytokine production by 4 day blasts (this level various between experiments). In an alternative protocol, cells are harvested after 3 days of stimulation with PHA, the blasts then washed 3 times with RPMI/10% FBS/2 mM L-glutamine/$5 \times 10^{-5}$ M 2-mercaptoethanol and antibiotics and then rested by culturing overnight at $1 \times 10^6$ cells/ml in the same media at 37 degrees C in a humidified incubator with 5% $CO_2$. Cells are then harvested, washed 3 times and then incubated with or without mAb for 30–45 minutes as described above prior to the addition of exogenous cytokines. Data are expressed as percent inhibition of T cell proliferation by calculating:

$$\frac{\text{cpm in the absence of mAb} - \text{cpm in presence of mAb}}{\text{cpm in the absence of mAb} - \text{background cpm (no exogenous cytokine)}} \times 100$$

The percent inhibition can be adjusted for any effect of an irrelevant control Ig assayed in parallel. As our anti-gc chain mAbs are all murine IgG1 antibodies, we employ the MOPC21 IgG1 myeloma protein as an irrelevant control Ig.

These growth assays are highly dependent upon the exogenous cytokine added based on the effect of neutralizing antibodies directed against these individual cytokines observed in 4–5 individual experiments (anti-IL-2 and anti-IL-4 mAbs are purchased from R&D Systems, Minneapolis, Minn.; rabbit anti-IL-7 IgG is purchased from Becton Dickinson, Bedford, Mass.).

Assays supported by exogenous IL-2 are strongly inhibited (>90%) by anti-IL-2 sera and are not inhibited (<10% blocking) by anti-IL4 or anti-IL-7 sera, demonstrating that they are specific for IL-2 induced cellular responses. As such, they are employed to identify anti-gc chain mAbs capable of inhibiting cellular responses to IL-2.

Likewise, assays supported by exogenous IL-4 are strongly inhibited by anti-IL-4 sera (>90% blocking) and are less affected by anti-IL-2 or anti-IL-7 sera (blocking ranges from 0–40%). Assays supported by exogenous IL-7 are strongly inhibited by anti-IL-7 (>90%) and are less affected by anti-IL-4 (<15% blocking) or anti-IL-2 (<40% blocking). As such, they are employed to identify anti-gc mAbs capable of inhibiting IL-4 or IL-7 signals.

Figure 4:
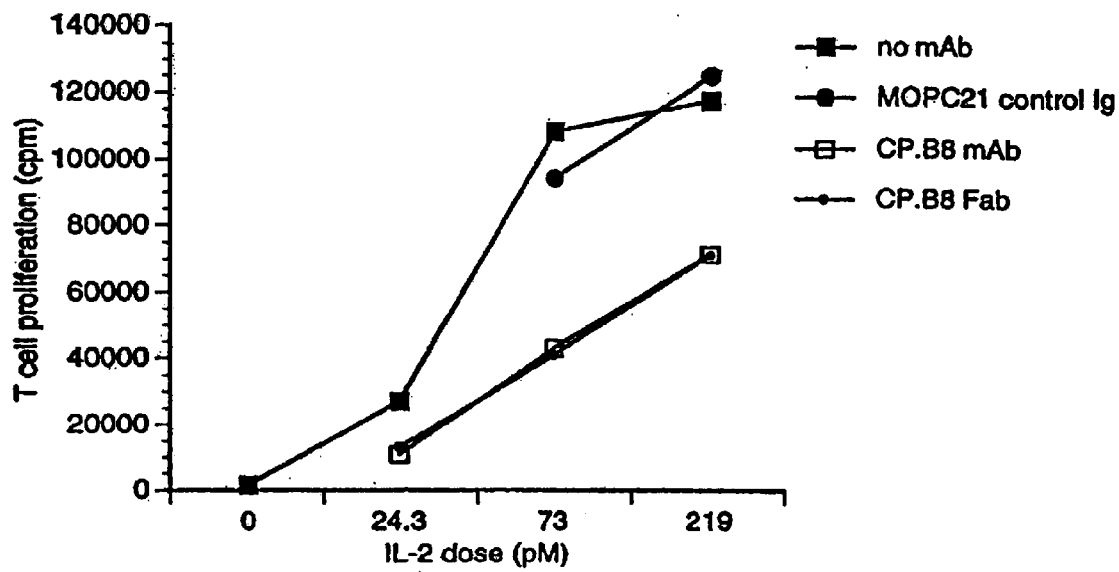
FIG. 4 is a graph showing inhibition of IL-2-induced T cell proliferation by the CP.B8 mAb and CP.B8 Fab fragment. Data points are indicated for different culture conditions as follows: filled squares are without mAb; large filled circles are with MOPC21 control Ig; open squares are with CP.B8 mAb; and small filled circles are with CP.B8 Fab fragment.
Figure 5:
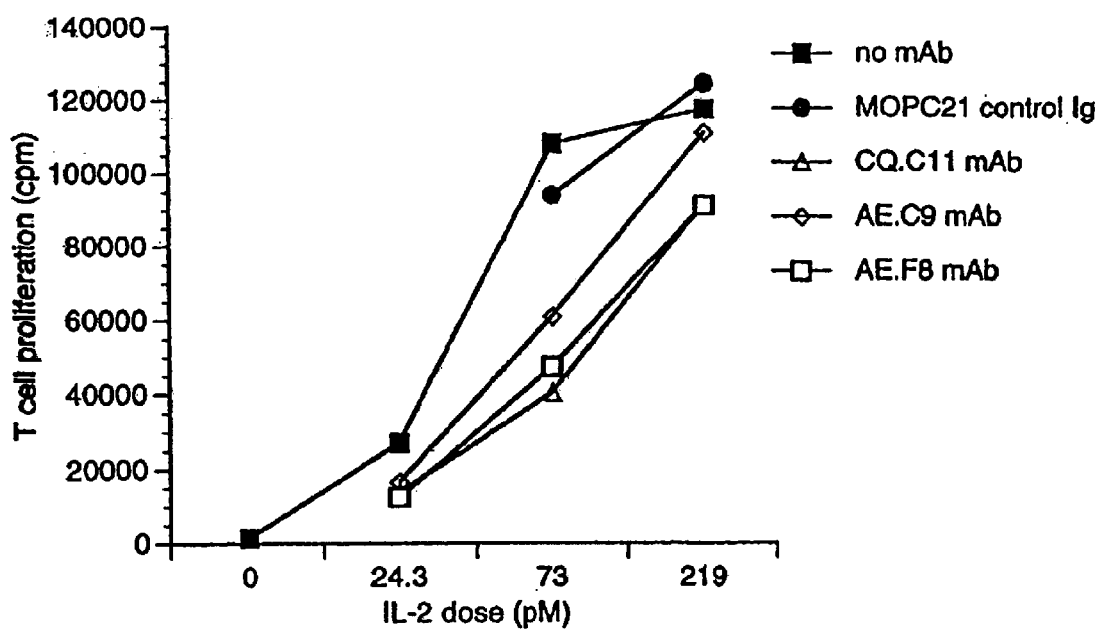
FIG. 5 is a graph showing inhibition of IL-2-induced T cell proliferation by anti-human gc chain mAbs. Data points are indicated for different culture conditions as follows: filled squares are without mAb; filled circles are with MOPC21 control Ig; open triangles are with CQ.C11 mAb; open diamonds are with AE.C9 mAb; and open squares are AE.F8 mAb.

We have established the effect of purified anti-gc chain mAbs on the cytokine-dependent growth of activated human T lymphocytes, with cell growth induced by exogenous IL-2, or IL-4, or IL-7, and measured according to the specifications described above. The MOPC-21 IgG1 myeloma protein is included as an isotype-matched control Ig. The effect of increasing doses of recombinant human IL-2 (ranging from 0 to 6630 pM) on proliferation of activated T cells indicates that a strong proliferative response can be elicited by exogenous IL-2. Fifty percent of maximum growth stimulation occurs at a concentration greater than 25 pM. The ability of the anti-human gc chain CP.B8 mAb and of its Fab fragment to inhibit this growth is shown in FIG. 4. The mAb and the Fab are each added to achieve final concentrations of 100 ug/ml. These data show strong inhibition of proliferation by the CP.B8 mAb over a wide range of IL-2 doses, including those regions of the growth curve corresponding to at least 50% of maximum stimulation. The CP.B8 mAb inhibited T cell proliferation by 51% and 44% at 73 pM and 219 pM IL-2, respectively, relative to the MOPC21 control Ig. The blocking activity of the CP.B8 Fab is also significant, parallelling that of the intact mAb. The inhibitory effect of other anti-gc chain mAbs CQ.C11, AE.C9 and AE.F8 are shown in FIG. 5. Each of these mAbs is added to achieve a final concentration of 10 ug/ml. These data again exhibit anti-gc chain mAbs which are capable of significantly blocking the IL-2 induced cell response, with 56% inhibition by CQ.C11, 35% by AE.C9 and 49% by AE.F8 relative to the control Ig under conditions wherein the response stimulated by IL-2 approaches maximum (73 pM).

Figure 6:
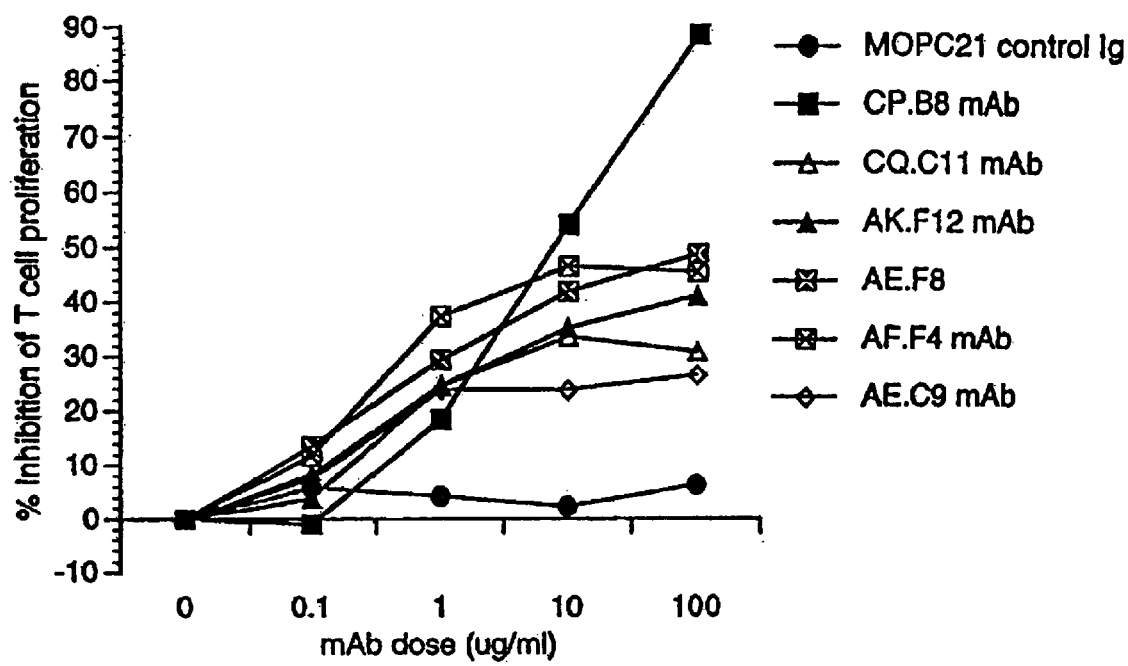
FIG. 6 is a graph showing inhibition of IL-2-induced T cell proliferation by anti-human gc chain mAbs, with IL-2 concentration of 73 pM. Data points are indicated for different culture conditions as follows: filled circles are with MOPC21 control Ig; filled squares are with CP.B8 mAb; open triangles are with CQ.C11 mAb; filled triangles are with AK.F12 mAb; filled squares with X marks are with AE.F8 mAb; open squares with X marks are with AF.F4 mAb; and open diamonds are with AE.C9 mAb.

The effect of different doses of these blocking anti-gc chain mAbs on IL-2 induced T cell growth is also examined in experiments wherein the IL-2 dose was fixed at 73 pM, thereby ensuring that stimulation would be at least 50% of maximum. We detected significant blocking by these mAbs of the IL-2 induced cell response (FIG. 6). Inhibition falls into two patterns: (1) A dose-dependent inhibition exhibited by mAb CP.B8 whose blocking increases with increasing dose of mAb, and (2) inhibition by other anti-gc mAbs which plateaus at the 1–10 ug/ml dose of mAb. The latter mAbs include CQ.C11, AK.F12 (cross competes with CQ.C11), AF.F4, AE.F8 (cross competes with AF.F4) and AE.C9. Additional experiments have established that each of these mAbs is able to block the IL-2 induced growth response by at least 25% on average, without the addition of a second compound. CP.B8 mAb is preferred based on its ability to achieve higher levels of inhibition, at least 40% inhibition on average.

Figure 7:
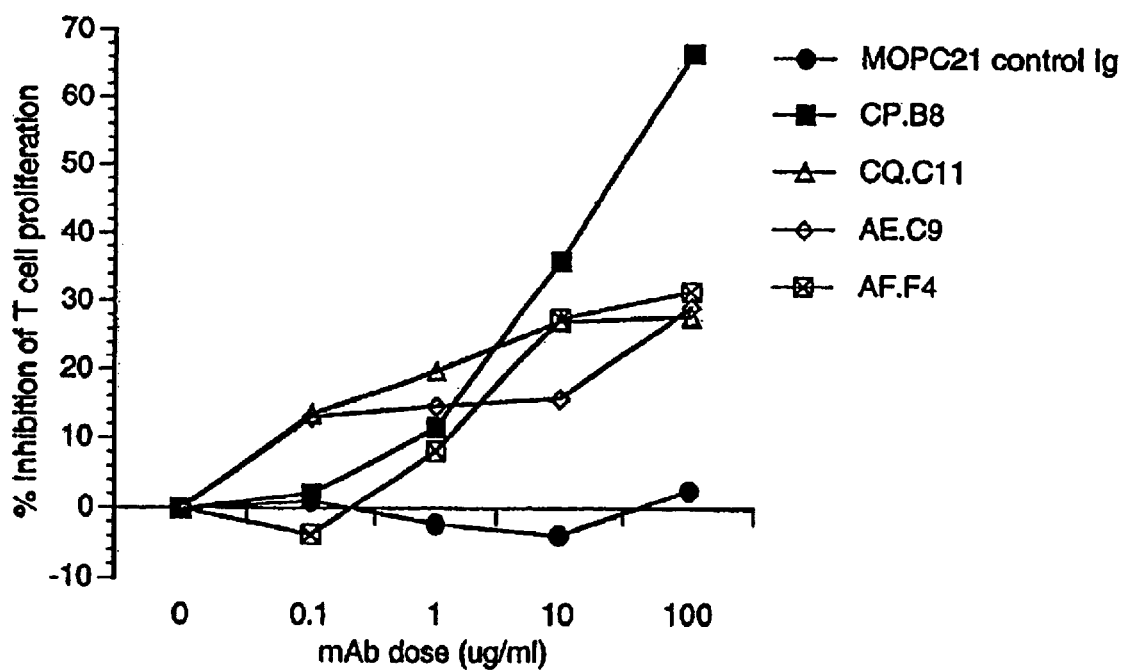
FIG. 7 is a graph showing inhibition of IL-4-induced T cell proliferation by anti-human gc chain mAbs, with IL-4 concentration of 228 pM. Data points are indicated for different culture conditions as follows:-filled circles are with MOPC21 control Ig; filled squares are with CP.B8 mAb; open triangles are with CQ.C11 mAb; open diamonds are with AE.C9 mAb; and open squares with X marks are with AF.F4 mAb.
Figure 8:
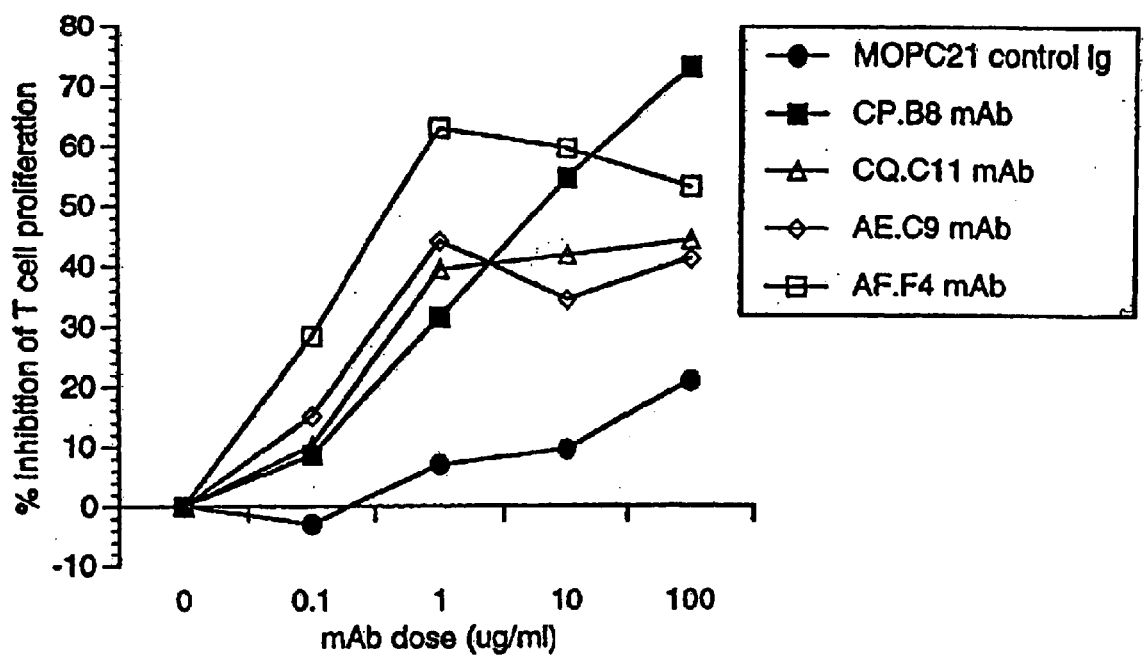
FIG. 8 is a graph showing inhibition of IL-7-induced T cell proliferation by anti-human gc chain mAbs, with IL-7 concentration of 65 pM. Data points are indicated for different culture conditions as follows: filled circles are with MOPC21 control Ig; filled squares are with CP.B8 mAb; open triangles are with CQ.C11 mAb; open diamonds are with AE.C9 mAb; and open squares are with AF.F4 mAb.

The effect of mAbs CP.B8, CQ.C11, AF.F4 and AE.C9 on IL-4 and IL-7 induced T cell growth responses are also established. For these assays, the doses of IL-4 and IL-7 are selected such that stimulation would be at least 50% of maximal (greater than 25 pM in both cases). The inhibitory activity of varying doses of anti-gc chain mAbs at a fixed dose of IL-4 (228 pM) or IL-7 (65 pM) are shown in FIG. 7 and FIG. 8, respectively. These data and additional experiments demonstrate that mAbs CP.B8, CQ.C11, AF.F4 and AE.C9 can significantly block IL-4 and of IL-7 induced responses, i.e. blocking by at least 25% on average, over that observed by the MOPC21 control Ig. Two patterns of blocking are again observed. The activity represented by the CP.B8 mAb is preferred based on its ability to achieve higher levels of blocking.

Figure 9:
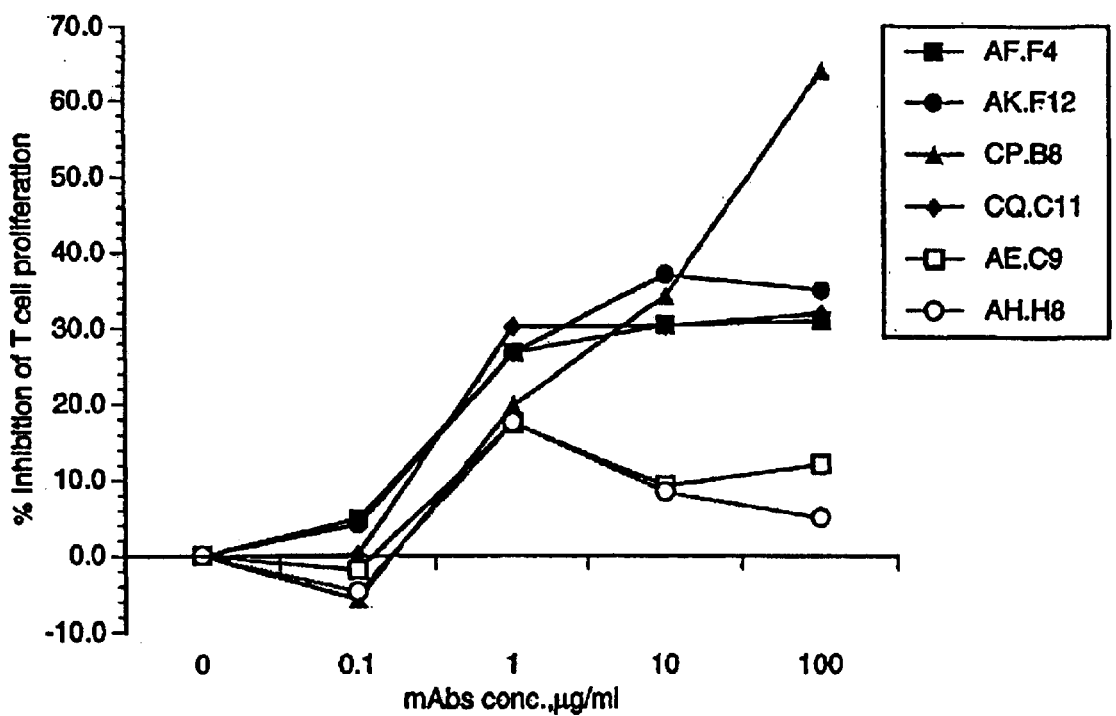
FIG. 9 is a graph showing inhibition of IL-15-induced T cell proliferation by anti-human gc chain mAbs, with IL-15 concentration of 88 pM. Data points are indicated for different culture conditions as follows: filled circles are with AK.F12 mAb; filled triangles are with CP.B8 mAb; filled diamonds are with CQ.C11 mAb; open squares are with AE.C9 mAb; closed squares are with AF.F4 mAb; and open circles are with AH.H8 mAb.

Using the same assay format as described above, 4 day PHA-blasts are stimulated with recombinant IL-15 in the presence or absence of anti-gc chain mAbs. A strong proliferative response can be elicited by exogenous IL-15 with 50% maximum proliferation ocurring at a dose of about 40 pM. The ability of anti-gc chain mAbs to elicit this response was tested at a fixed IL-15 concentration, 88 pM. FIG. 9 shows significant inhibition of IL-15 induced proliferation by a series of anti-gc chain mAbs, including CP.B8, AK.F12, CQ.C11 and AF.F4.

B. Inhibitory Effect on the Primary Mixed Lymphocyte Reaction (MLR)

Figure 10:
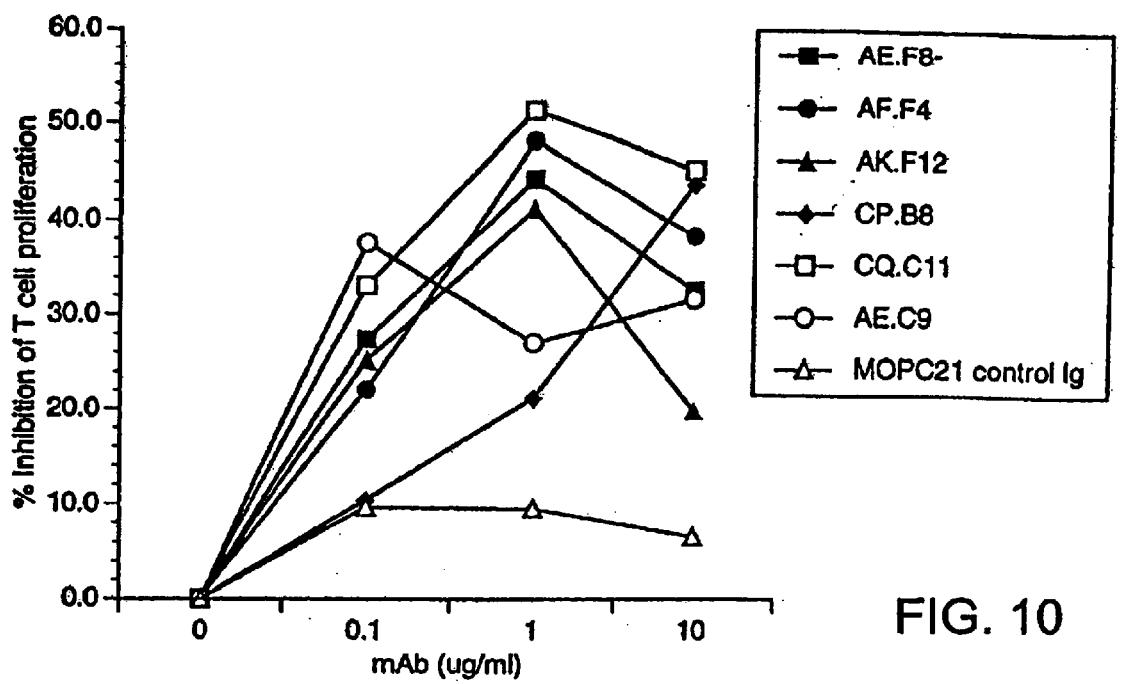
FIG. 10 is a graph showing effect of anti-gc mAbs on a human primary MLR. Percent inhibition of T cell proliferation is plotted against the concentration of added mAb in ug/ml. Data points show % blocking by different mAbs, and are indicated for different mAbs as follows: filled squares are with AE.F8 mAb; filled circles are with AF.F4 mAb; filled triangles are with AK.F12 mAb; filled diamonds are with CP.B8 mAb; open squares are with CQ.C11 mAb; open circles are with AE.C9 mAb; and open triangles are with MOPC21 control Ig.

Primary MLR cultures are set up by co-culturing enriched CD4+ human PBMC ($1\times10^5$ cells) with $2\times10^5$ allogeneic PBMC which had been exposed to 2000 rads of gamma irradiation and serve as stimulator cells in a total volume of 200 ul of RPMI media supplemented with 10% FBS, 2 mM L-glutamine, 2-ME and antibiotics in a humidified 37 degree incubator for 5 days. Proliferation of the CD4+ responder population is measured by $^3$H-thymidine incorporation during the last 16 hours of culture. The ability of anti-gc mAbs to inhibit an antigen-specific proliferative response of naive CD4+ T cells is shown (FIG. 10). In this experiment, the cpm incorporated in the absence of added mAb is 25,703 cpm and background cpm (no cytokine added) is 325 cpm. This response is greater than 50% of the maximum stimulation achievable with this combination of responder and stimulator cells. The results demonstrate significant blocking by all mAbs, many achieving 30–40% inhibition at 1 ug/ml relative to the MOPC21 control Ig.

The MLR is primarily IL-2 driven, as exemplified by 88% inhibition by anti-IL-2 sera and less than 24% inhibition by antisera directed at other cytokines including IL-4 and IL-7 in this experiment. Our data thereby establish anti-gc chain mAbs capable of blocking the proliferative response of mature, naive T cells to IL-2 produced upon antigen-activation.

EXAMPLE 4

Gc Chain Blocking Agents as Noncompetitive Inhibitors

A. Identifying target sites for noncompetitive inhibition of the IL-4 receptor

Figure 11:
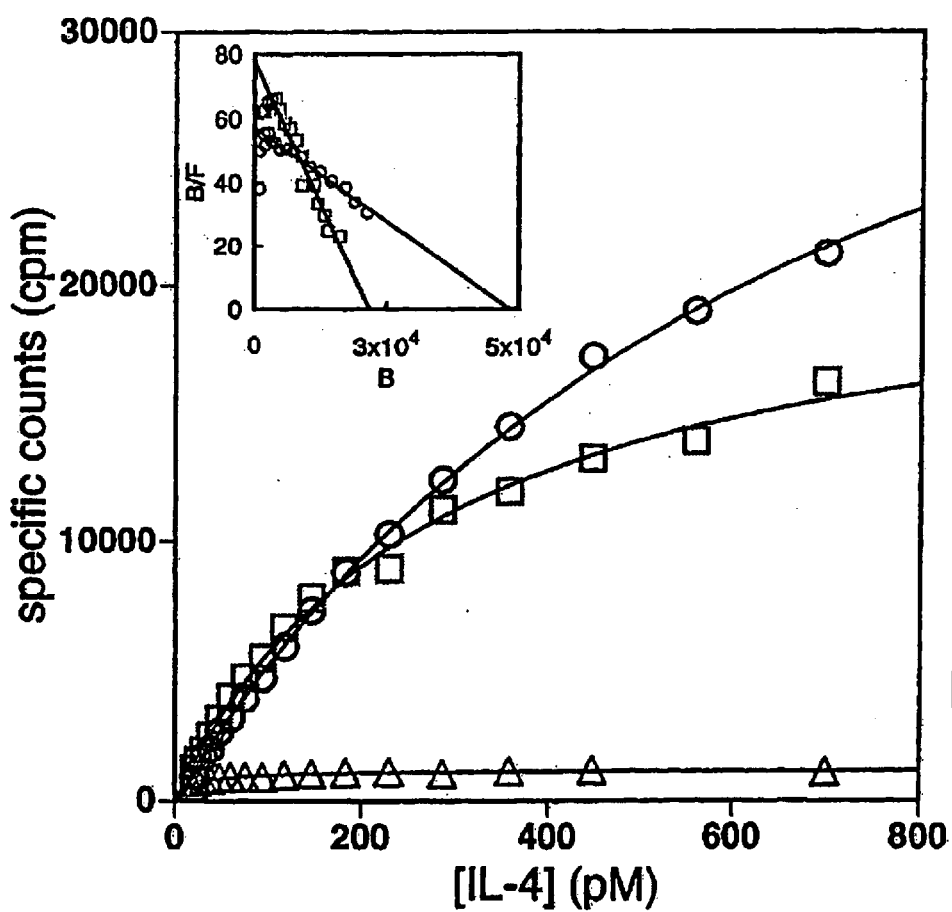
FIG. 11 is a graph showing binding of radiolabelled IL-4 to COS cells transfected with IL-4R alpha chain (squares) or cotransfected with both the IL-4R alpha chain and gc (circles). Data for mock-transfected cells are the triangles. The inset plot shows data for binding to cells expressing IL-4R alpha chain alone (squares) or IL-4R alpha chain and gc (circles) replotted in a Scatchard plot, highlighting the approximately 3 fold increase in binding affinity to IL-4R that is conferred by coexpression of gc.
Figure 12:
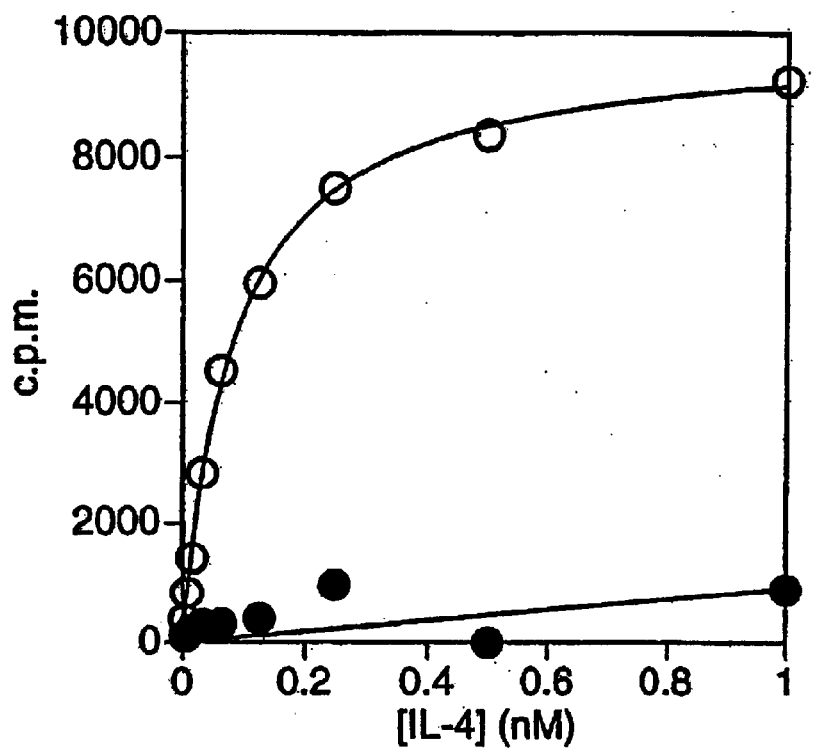
FIG. 12 is a graph showing binding of radiolabelled IL-4 to PHA-activated (open circles) and resting (closed circles) peripheral blood lymphocytes. The binding data for PHA-activated cells fit a simple hyperbolic equation
Figure 13A:
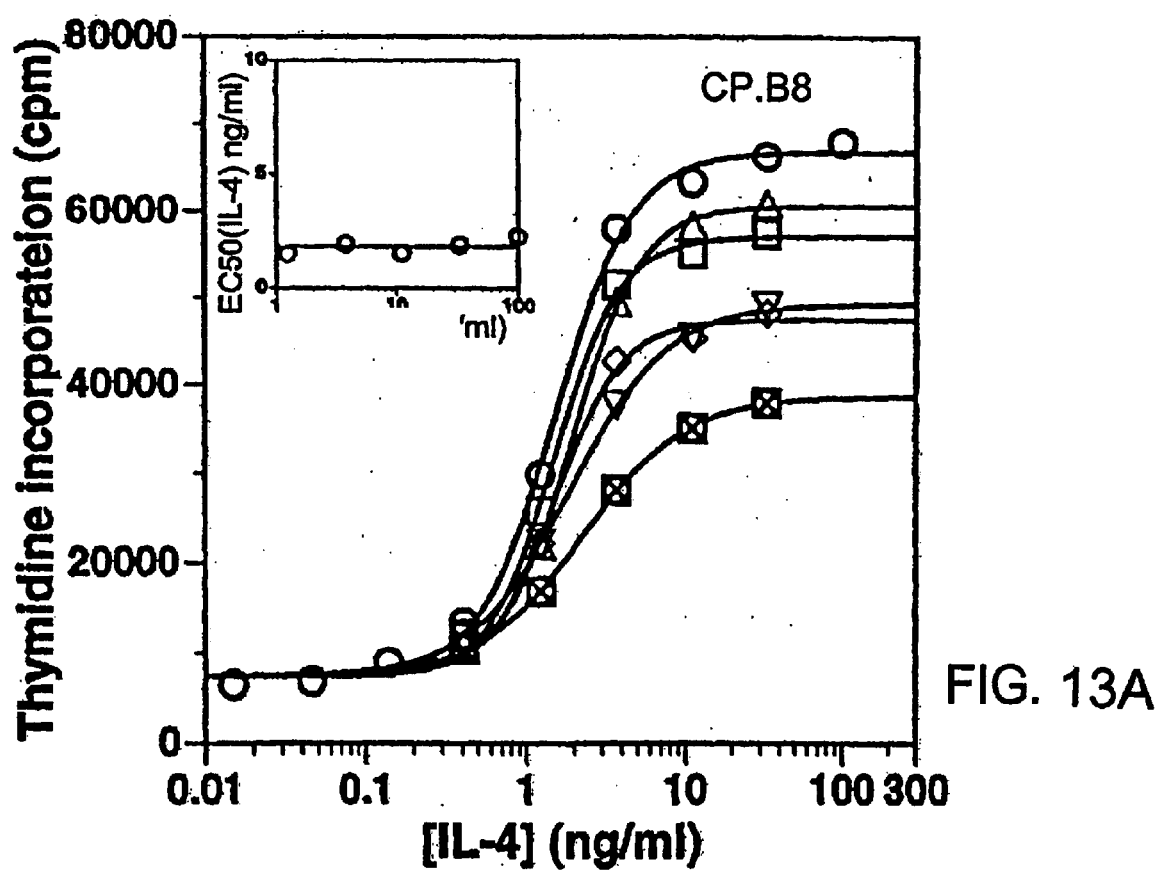
FIG. 13 is a series of plots showing the effect of CP.B8 or anti-IL-4R alpha chain mAb on IL-4 dependent proliferation of PHA-activated T cells. The effect of CP.B8 on IL-4 dependent proliferation of PHA blasts is shown FIG. 13A and the effect of mAb directed against the alpha chain of IL-4R is shown in FIG. 13C. The effect of isotype-matched control Ig proteins MOPC21 and UPC10 is shown in FIG. 13B. Open circles show the response in the absence of mAb or control Ig. Other symbols show response the effects of increasing concentrations of mAb up to a mAb concentration of 100 ug/ml (open squares with X marks are for CP.B8 and open circles with X marks are for anti-IL-4R alpha).
Figure 13B:
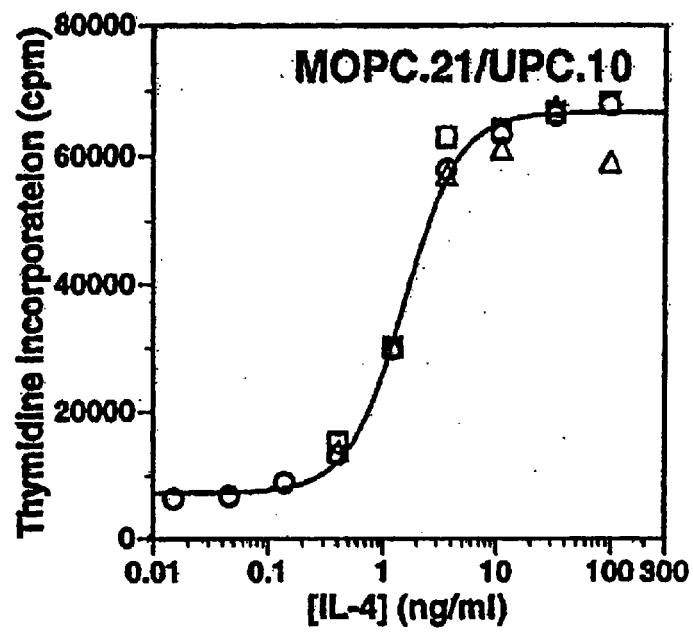
Figure 13C:
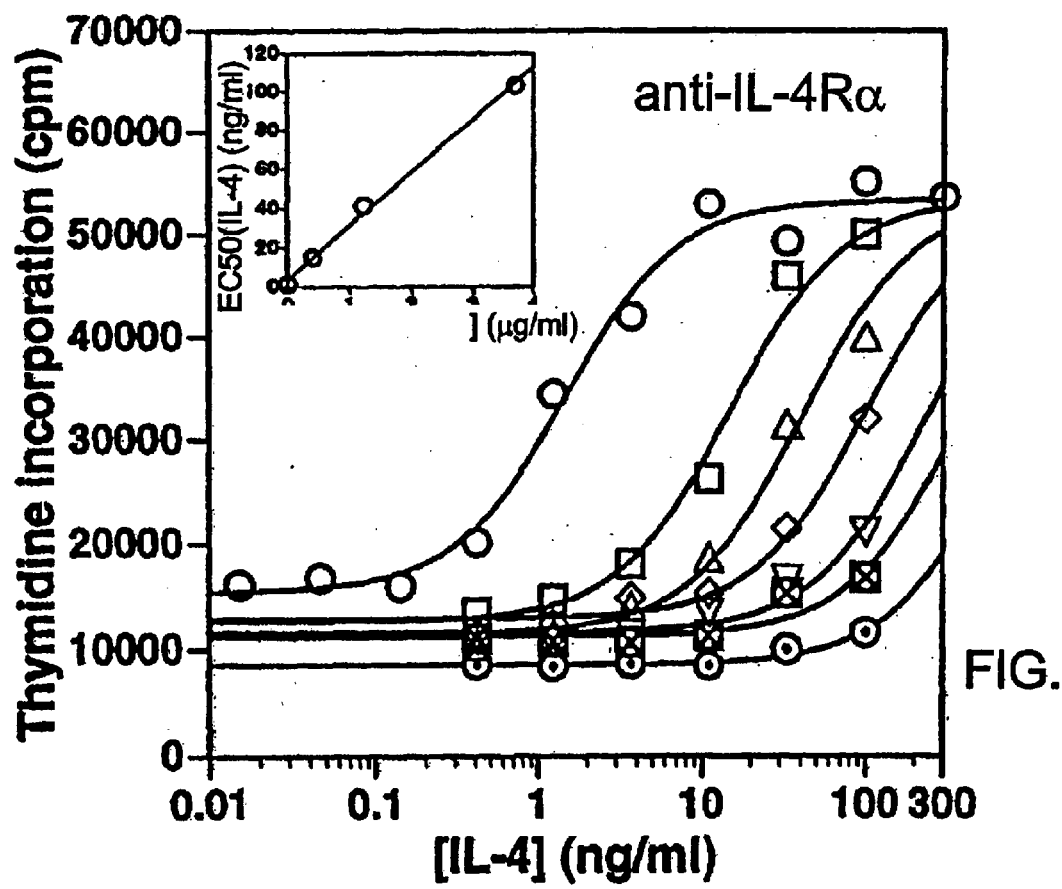
Figure 14:
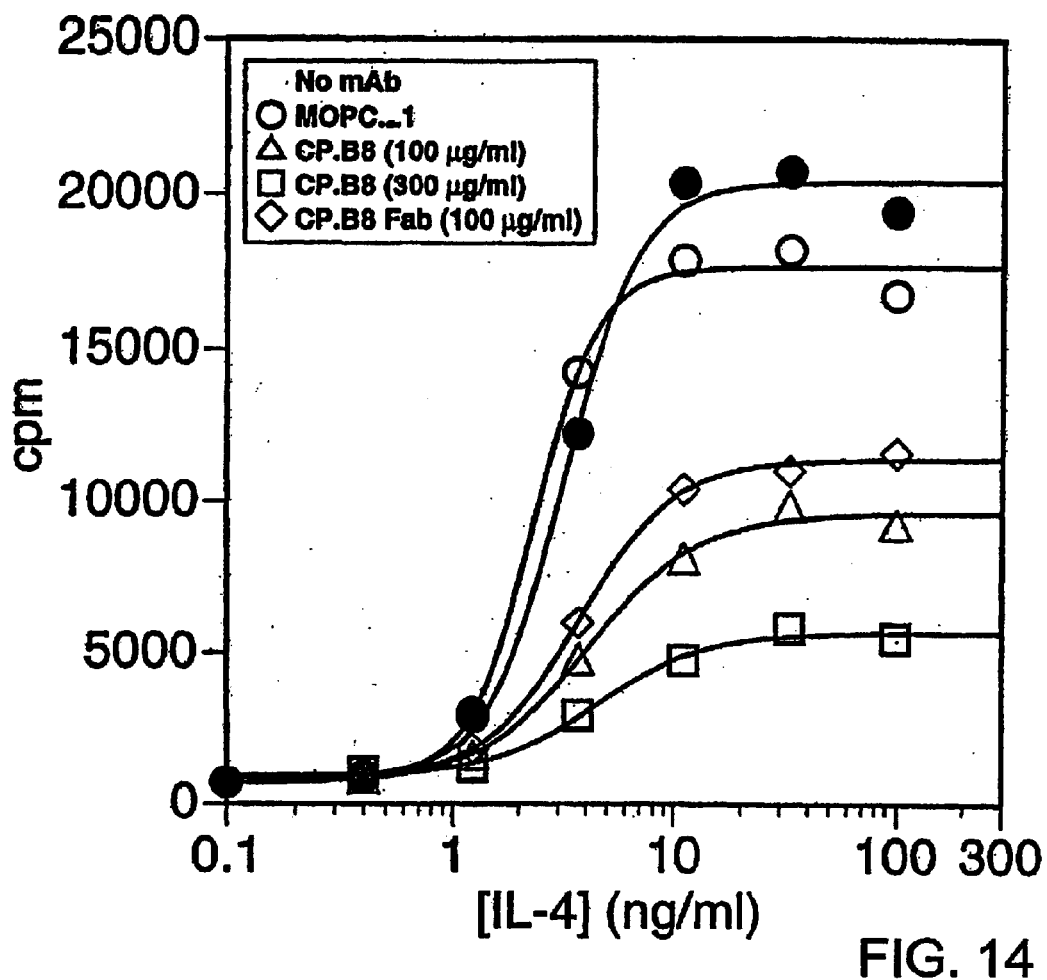
FIG. 14 is a graph showing the effect of CP.B8 (open triangle and square) and its Fab fragment (open diamond) on the dose response curve for IL-4-dependent proliferation of PHA-activated T cells. Open circles show the effect of isotype control MOPC 21 Ig and closed circles show the effect in the absence of mAb.
Figure 15A:
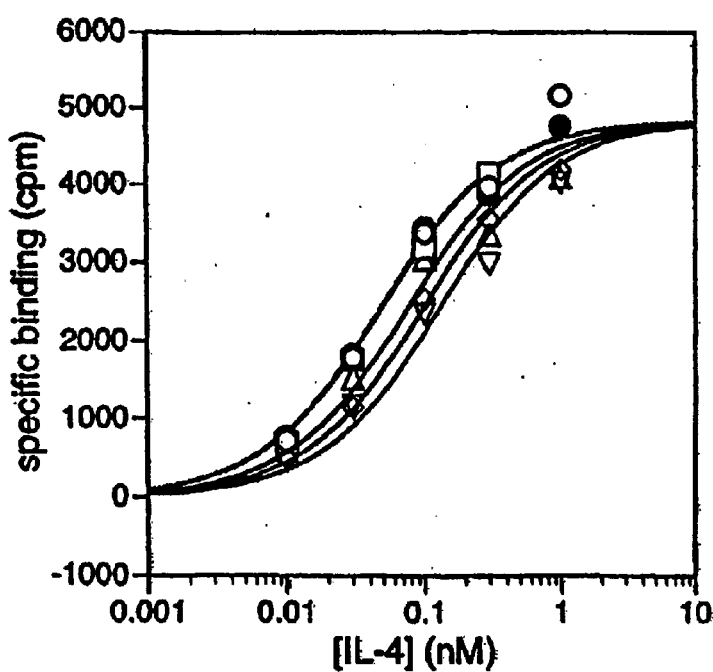
FIG. 15 is a series of graphs showing the effect of various concentrations of CP.B8 (FIG. 15A), anti-IL-4R alpha chain mAb (FIG. 15B) or MOPC 21 (FIG. 15C) on binding of radiolabelled IL-4 to PHA-activated PBLs. Filled circles show binding in the absence of mAb and open circles show the effects of increasing concentrations of mAb, in the order circles<squares<triangles<diamonds<inverted triangles, up to a mAb concentration of 100 ug/ml. CP.B8 does not block binding a high IL4 concentrations but may cause a modest decrease in the apparent affinity of binding. The expected competitive pattern of binding inhibition is shown in Panel B. The isotype control for the effect of CP.B8 has no effect (FIG. 15C).
Figure 15B:
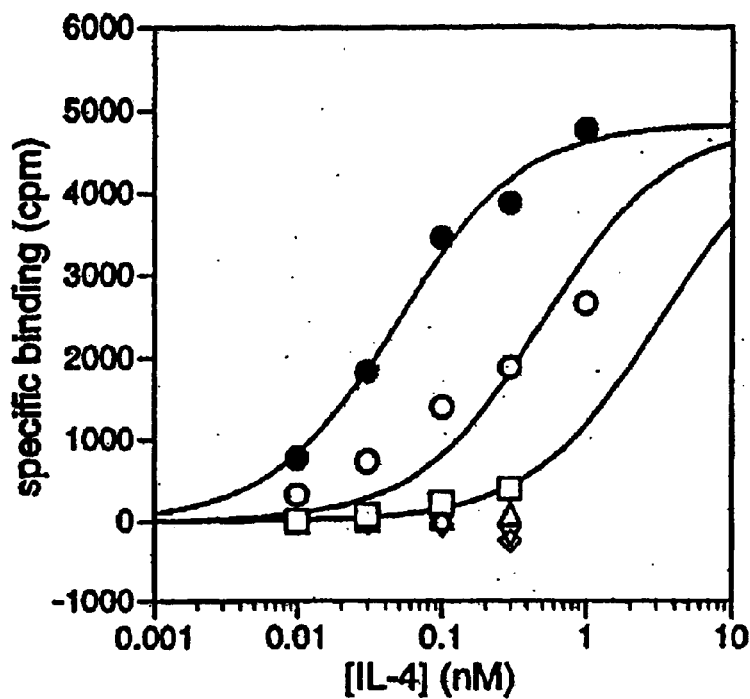
Figure 15C:
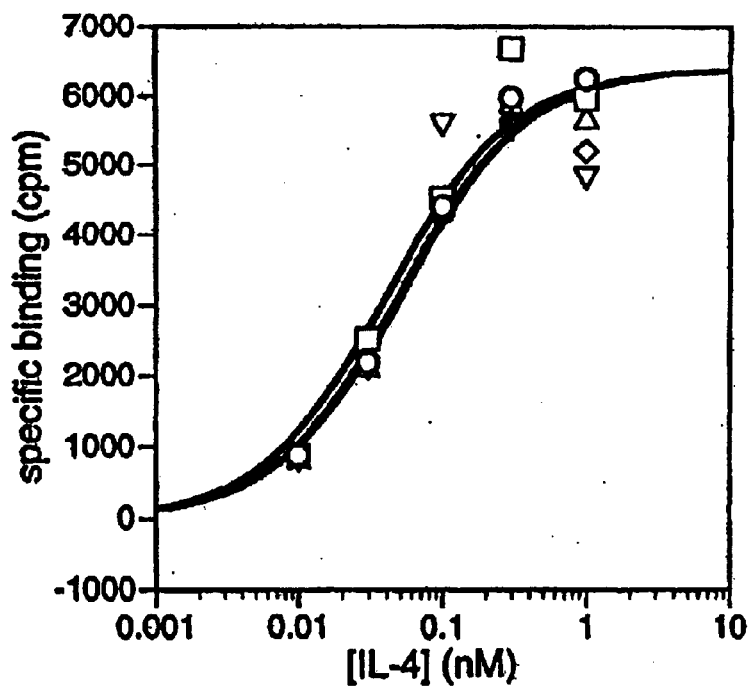
Figure 16:
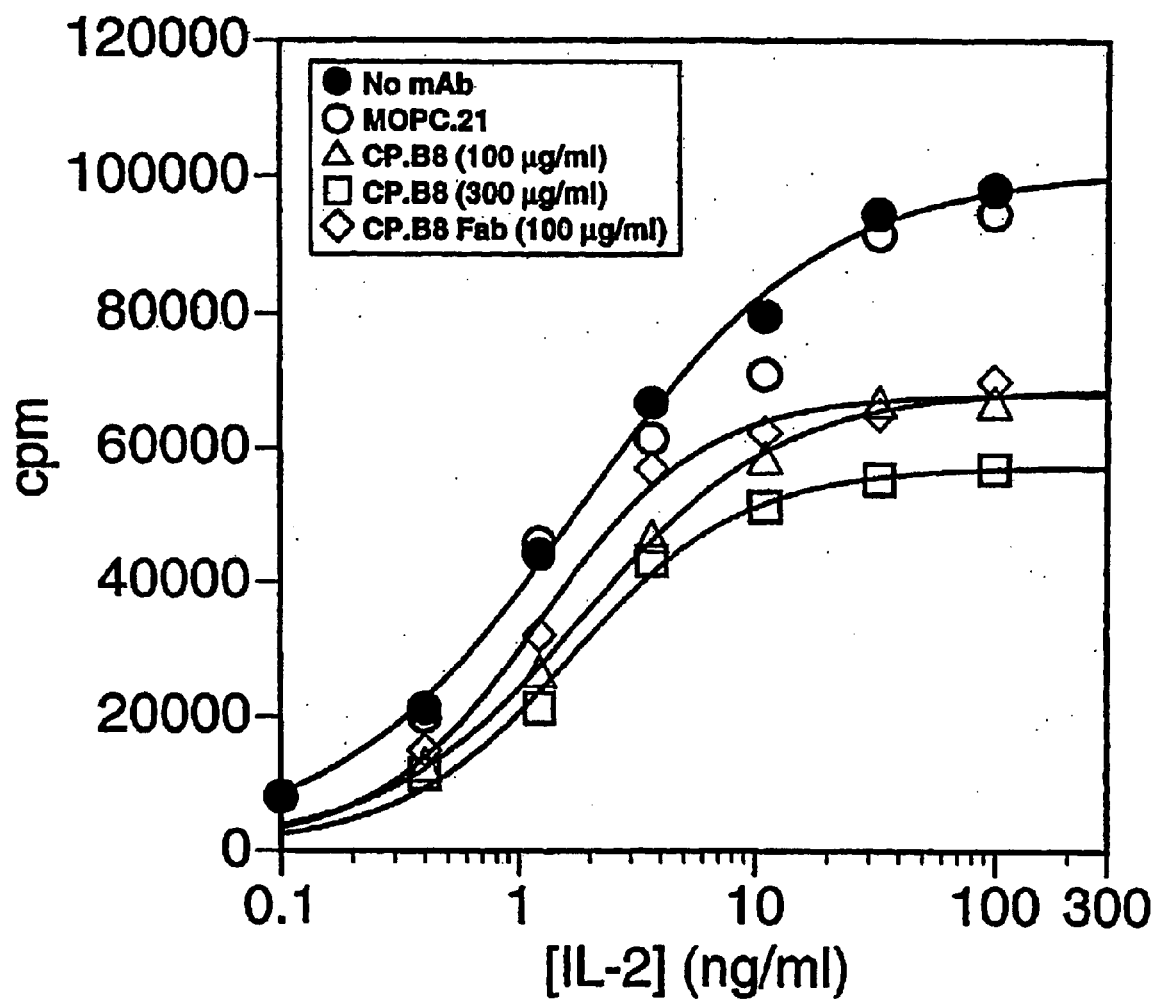
FIG. 16 is a graph showing the effect of CP.B8 (open triangle and square) and its Fab fragment (open diamond) on the dose response curve for IL-2- dependent proliferation of PHA-activated T cells. Closed circles show the effect of isotype control MOPC.21 and closed circles show the effect in the absence of mAb.

FIG. 11 shows data for the binding of IL-4 to COS cells transfected with IL-4R alpha chain or cotransfected with both the alpha chain and gc. Data for mock-transfected cells (triangles) shows that there is very little specific binding of IL-4 to Cos cells that do not express the alpha chain. It is known that IL-4 has no detectable affinity for binding to gc in the absence of IL-4R alpha chain. FIG. 11 shows that Cos cells transfected with both gc and IL-4R alpha bind IL-4 with about a 3-fold higher affinity than the $K_D$ of 760 pM observed for binding to cells transfected with human IL-4R alpha alone. The observation that gc confers only a small increase in the affinity of IL-4 for binding to cells expressing IL-4R alpha chain has been noted previously (Russel et al. *Science* 262: 1880–1883 (1993)) who found cotransfection of gc to cause a similar 3-fold increase in binding affinity. Data for the binding of IL-4 to PHA-activated T cells is shown by the open symbols in FIG. 12. Multiple determinations consistently show that the binding data fit a simple hyperbolic equation and that IL-4 binds to the cells with an affinity of $K_{D(App)}$ about 60 pM (n=4; actual values were 49,80,52 and 55 pM). The filled symbols in FIG. 12 show that there is little or no binding of IL-4 to unactivated PBLs, consistent with the known significant up-regulation of IL-4R alpha chain and of gc that occurs upon activation of T cells.

The high affinity and low affinity binding constants measured for IL-4R alpha chain in the presence and absence of cotransfected gc can be considered in terms of the scheme shown below:

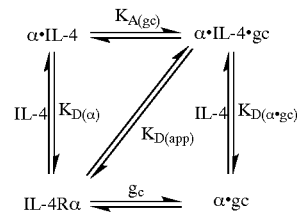

The observed $K_{D(App)}$ of about 60 pM for the binding of IL-4 to activated T cells expressing both IL-4R alpha chain and gc is shown by the diagonal pathway in the above scheme, and refers to the overall equilibrium constant for the formation of high affinity ternary complex: alpha/IL-4/gc, from free IL-4 and unassociated IL-4R alpha chain and gc. $K_{D(alpha)}$ refers to the affinity of the binding of IL-4 to IL-4R alpha in the absence of gc, which was estimated to be about 760 pM from the binding of IL-4 to transfected Cos cells shown in FIG. 11. From the above scheme, we derive the following relation to describe the affinity of gc for binding to the binary complex: alpha chain/IL-4 on the surface of activated T cells:

$$K_A = K_{D(alpha)}/K_{D(App)} = 760 \text{ pm}/60 \text{ pM} = 13$$

That is, if IL-4 binds to the alpha chain with a $K_D$=760 pM, then in order to get an overall equilibrium constant of $K_D$=60 pM for binding to activated T cells expressing both receptor chains, the equilibrium constant for the binding of gc to alpha chain/IL-4 on the cell surface must have a $K_A$ value of 13. This $K_A$ implies that, at saturating concentrations of IL-4, the IL-4R alpha chain is distributed between free alpha/IL-4 and the ternary complex: alpha chain/IL-4/gc in a ratio that favors the ternary complex by about 13:1. In the experiment in question, binding of IL-4 to cotransfected cells increased the fraction of IL-4R alpha chains involved in the ternary (signalling) complex from a low basal level in the absence of IL-4 to about 93% at saturating IL-4.

This significance is that, even at high saturating concentrations of IL-4, the binding interaction between gc and the binary complex alpha chain/IL-4 remains of fairly low affinity. Thus, the gc binding site constitutes a good point for intervention for the development of noncompetitive inhibitors which block formation of the ternary signalling complex without directly competing against the binding of the high affinity natural ligand.

B. CP.B8 is a noncompetitive inhibitor of IL-4 dependent proliferation of activated T cells The ability of high concentrations of IL-4 to overcome the inhibitory effect of CP.B8 on IL-4 dependent T cell proliferation was tested as shown in FIG. 13. Dose response curves were determined for IL-4 in the presence of various fixed concentrations of the anti gc mAb CP.B8. Similar measurements were made using a control anti IL-4R alpha mAb known to bind with high affinity to the IL-4 binding site on the alpha chain and block the binding of IL-4. FIG. 13 shows that the IL-4 dependent proliferation of PHA blasts is inhibited in a dose dependent manner by CP.B8 (Panel A) and by the mAb directed against the alpha chain of IL-4R (Panel B) but not by the respective isotype-matched controls MOPC21 and UPC10 (Panel C). In particular, Panel A shows that CP.B8 depresses IL-4 dependent proliferation over the entire IL-4 dosage range, but does not detectably alter EC50 for the cytokine's effect (data not presented). This noncompetitive pattern of inhibition, characterized by the fact that the dose response curves at different CP.B8 concentrations extrapolate to different levels of proliferation at high IL-4, shows that inhibition of CP.B8 cannot be overcome with high concentrations of cytokine. In contrast, Panel B shows that inhibition by the anti IL-4R alpha chain mAb shows a typical competitive pattern: the EC50 for IL-4 increases with increasing concentrations of mAb, and the data are consistent with the dose-response curves extrapolating to a full proliferative response at high IL-4 concentrations. This indicates that, unlike CP.B8, the effect of any given concentration of the anti-IL-4R alpha chain mAb can be overcome by a sufficiently high IL-4 concentration.

FIG. 14 shows that, in addition, the Fab fragment of CP.B8 is also active as a noncompetitive inhibitor of IL-4 dependent proliferation of activated T cells. This suggests that cross linking of gc chains, which may occur with a bivalent reagent such as a mAb, is not required to cause inhibition of an IL-4 dependent proliferative response. If the IL-4 receptor functions through a mechanism involving ligand-induced receptor chain dimerization (i.e., if IL-4 R alpha chain and gc are not significantly preassociated in the absence of bound IL-4 and it is binding of IL-4 that induces the receptor chains to associate in a ternary signalling complex: alpha chain/IL-4/gc), a mAb or similar antagonistic molecule of the invention directed towards gc might block the participation of gc in a ternary complex with IL-4R alpha chain and IL-4 but should not influence the ability of the alpha chain itself to bind to IL-4. Such an inhibitor might be expected to increase the apparent $K_D$ for IL-4 binding from the relatively high affinity seen for binding to the alpha chain alone, but it should not otherwise block or affect IL-4 binding to cells.

FIG. 15 shows the effect of various concentrations of CP.B8 on the binding of IL-4 to PHA activated T cells, together with analogous data for the effect on cytokine binding of the blocking anti-IL-4R alpha chain mAb used in the experiment in FIG. 13. FIG. 15B shows that the anti IL-4R alpha chain mAb blocks binding of IL-4 to cells competitively with respect to IL-4, as would be expected for two molecules that compete for binding to mutually exclusive sites on the same receptor chain. In contrast FIG. 15 A shows that CP.B8 does not block binding at high levels of IL-4, even at a mAb concentration of 100 ug/ml which the data in FIG. 13 show to inhibit IL-4 dependent proliferation of similar cells by over 50%. CP.B8 may, however, bring about a modest decrease in the affinity of the cells for binding IL-4, manifested by a small progressive shift of the dose response curves in FIG. 15A towards higher IL-4 concentrations as the mAb concentration is increased. This is expected because the binding of IL-4 is sensitive to the ability of gc to participate in the formation of a complex with IL-4 and the alpha chain as a result of the modest enhancement of affinity that gc confers upon IL-4R alpha chain. This is consistent with the hypothesis that binding of CP.B8 to gc prevents the recruitment of this receptor subunit into a ternary complex with IL-4 and the alpha chain.

The method and analysis summarized here provides a means to estimate the inter-chain binding affinity between two components of a multi-chain receptor in the presence of saturating concentration of cytokine, or corresponding other ligand as it occurs on the surface of potential target cells that express the receptor. An example of how the method can be applied to a receptor other than the IL-4 receptor follows:

Published data indicate that the high-affinity form of the IL-2 receptor consists of three receptor chains. Sugamura et al., *Adv. Immunol.,* 59: 225–277 (1995). One of these is a receptor specific IL-2R beta chain which, like the IL-4R alpha chain and gc, has its extracellular portion consisting of 2 FNIII domains and has an intracellular cytoplasmic portion that is known to interact with downstream signalling components such as the signalling kinase Jak1. The IL-2R alpha chain has little cytoplasmic structure. The IL-2R alpha and beta chains are preassociated on activated T cells (Landgraf et al., *J. Biol. Chem.,* 267: 18511–18519 (1992)) and this complex binds IL-2 with an affinity of $K_{D(alpha/beta)}$ of about 100 pM. Cells expressing IL-2R alpha, beta and gc bind IL-2 with a higher affinity of $K_{D(App)}$ equal to about 10 pM. Thus, application of the thermodynamic scheme devised for the IL-4 receptor leads to the calculation that gc binds alpha:beta in the presence of saturating IL-2 (i.e., to alpha/beta/IL-2) with an affinity of $K_A$ equal to about 100 pM/ 10 pM=10. The affinity of gc for other components of the IL-2 receptor appears to be comparatively weak compared to the affinity of gc for components of the IL-4 receptor, since the $K_A$ values estimated for the two receptors are roughly the same. This leads to the expectation that CP.B8 and its Fab fragment should have activity as noncompetitive inhibitors of the high affinity IL-2 receptor that is roughly comparable to their activity against the IL-4 receptor.

FIG. 16 shows that an experimental test of this expectation establishes its validity. Both CP.B8 and its Fab fragment inhibit the IL-2 dependent proliferation of activated T cells in a manner that is noncompetitive with respect to IL-2 concentrations, analgous to the observations made with the IL-4 receptor. This result indicates that the approach to identifying receptors susceptible to inhibition by noncompetitive agents directed against gc can be applied to gc-utilizing receptors other than IL-4R and that CP.B8 and other embodiments of the invention constitute noncompetitive inhibitors of this type. This approach is similarly to be expected to be useful for identification of susceptible target sites and corresponding noncompetitive inhibitors of other families of multichain receptors other than those that use gc as a component.

As a positive control for inhibition of binding by a given biotin-conjugated mAb, the mAb itself was employed as an inhibitor and near complete inhibition was demonstrated under these assay conditions. As a negative control for inhibition of binding by a given biotin-conjugated mAb, the MOPC21 control Ig was used, demonstrating little if any inhibition under these assay conditions. Table 2 shows the results. Different boxed regions indicate distinct mAb epitope groups. In some cases, several mAbs fall into the same box, indicating that they belong to the same epitope group, e.g., AF.F4, AK.F12 and CQ.C11 mAbs. In some cases, a unique specificity was exhibited as exemplified by the CP.B8 monoclonal antibody.

TABLE 2

| Unconjugated | Biotinylated mAbs | | | | | | |
|---|---|---|---|---|---|---|---|
| mAbs | CP.B8 | AF.F4 | AK.F12 | CQ.C11 | AE.F8 | AH.H8 | AE.C9 |
| MOPC21 | 0* | 0 | 11 | 0 | 0 | 0 | 7 |
| CP.B8 | 87 | 26 | 37 | 46 | 0 | 0 | 18 |
| AF.F4 | 14 | 98 | 95 | 96 | 0 | 0 | 2 |
| AK.F12 | 14 | 95 | 95 | 96 | 0 | 0 | 7 |
| CQ.C11 | 17 | 98 | 96 | 97 | 0 | 0 | 5 |
| BI.B12 | 25 | 94 | 93 | 95 | 94 | 94 | 17 |
| AE.F8 | 11 | 23 | 17 | 17 | 97 | 95 | 21 |
| CJ.F4 | 13 | 14 | 0 | 8 | 93 | 78 | 0 |
| AH.H8 | 7 | 23 | 19 | 21 | 89 | 96 | 18 |
| AE.C9 | 0 | 11 | 14 | 23 | 0 | 0 | 96 |

*Values are percent of inhibition of binding of biotinylated mAbs by unconjugated mAbs and are mean of 2 determinations.

EXPERIMENT 5 mAb Crossblocking studies

The ability of different anti-gc chain mAbs to bind gc chain at the same or nearby antigenic determinants and thereby compete with one another for binding to the gc chain can be determined by cell surface crossblocking studies. Briefly, different purified anti-gc chain mAbs (at least 10 ug/ml) or an irrelevant control Ig were allowed to bind and saturate the surface of human PHA blasts for 30 minutes at 4 degrees C in PBS-1% BSA-0.02% sodium azide buffer. Binding studies performed previously established that a 10 ug/ml dose of these mAbs is sufficient to saturate the cell surface. The ability of a biotin-conjugated anti-gc mAb to bind to the same cells was then determined. This biotin-conjugated mAb was added at a limiting concentration based on previous binding studies (less than or equal to 5 ug/ml) with 15–30 minutes binding time allowed such that their binding is suboptimal and sensitive to inhibition. The biotin anti-gc chain mAbs were added at concentrations ranging from 1 to 5 ug/ml. After 30 minutes, the cells are then washed 3 times in the same buffer and binding detected with PE-conjugated streptavidin and fluorescent activated cell sorter analysis.

Mean fluorescence intensity (MFI) values were used to calculate the degree of inhibition by a given monoclonal antibody as follows:

Percent inhibition=100×(MFI for biotin-mAb binding with inhibitor/MFI for biotin-mAb binding without inhibitor)

Independent crossblocking studies also were performed using alternative formats, i.e., solid phase assays employing recombinant gc chain polypeptide. Immobilized anti-gc chain mAb binding to recombinant soluble gc chain in the absence or in the presence of another soluble mAb was measured. Further, biotin-mAb binding to immobilized recombinant gc chain in the absence or presence of another unconjugated mAb was measured. All formats were employed to determine the crossblocking capability of the various anti-gc chain monoclonal antibodies of the invention. We noted only minor differences.

In summary, the CP.B8 mAb constitutes a unique specificity, a consistent finding based on all of the assays employed. Likewise, the AE.C9 mAb constitutes a unique specificity. The AF.F4, CQ.C11 and AK.F12 mAbs were mapped to the same epitope group and distinguished from the AE.F8 mAb based on cell surface cross blocking. However, crossblocking between the AE.F8 and AF.F4 mAbs was observed in assays which employed soluble gc chain rather than cell surface gc chain. Other anti-gc chain mAbs which crossblock with one or more of CP.B8, AE.C9, CQ.C11, AE.F8 and AF.F4 include AD.E12, BN.C2, AH.H8, BI.B12, AH.C12, CJ.F4, AG.F1, AH.C12, AD.F3, and AC.E12.

EXPERIMENT 6

Mapping the CP.B8 mAb epitope on gc chain

The CP.B8 mAb represents a preferred inhibitory activity given its ability to mediate increased blocking of cytokine responses with increasing doses of mAb. To better characterize this activity, the CP.B8 epitope on gc chain has been localized by transient expression of gc chain mutants in COS-7 cells. COS-7 cells are transiently transfected with 20 ug of DNA encoding the gc chain mutant or wildtype cDNA and 180 ug of herring sperm carrier DNA. After 2–3 days, COS-7 cells are harvested and analyzed by immnunofluorescent staining with anti-gc chain mAbs. MAbs are used at 10 ug/ml in PBS-1% BSA-0.02% sodium azide and allowed 30 minutes to bind to $1\times10^6$ COS-7 cells. Cells are then washed 2 times, and bound mAb is detected with than 30% indicate residues that are believed most critical to the CP.B8 epitope. Mutations which affect CP.B8 binding do not appear to grossly affect the conformation of the gc molecule since, for any given mutation, the binding of other mAbs is unaffected (for example, see binding of the CJF4 mAb in Table 3). These data indicate that the CP.B8 epitope includes amino acid residues selected from one or more of the following sequences of the gc chain: FNVEY (SEQ ID NO: 13); KEIHLYQ (SEQ ID NO: 14); LQNLVIP (SEQ ID NO: 15); HCLEH (SEQ ID NO. 16); and FNP (SEQ ID NO: 17).

TABLE 3

| Ala Substitutions in Connecting Loops | | Anti-gc chain mAbs (% binding to mutant gc chain/wildtype gc chain) | | | | | | |
|---|---|---|---|---|---|---|---|---|
| | Residues | CP.B8 | AE.F8 | AF.F4 | AK.F12 | CQ.C11 | BI.B12 | CJ.F4 |
| Domain 1 Loop | | | | | | | | |
| AB | FNV | 9 | 79 | 80 | nd | nd | nd | nd |
| | VEY | 0 | 80 | 75 | 0 | nd | 92 | 98 |
| CC | SDN | 68 | 74 | 77 | 71 | nd | 66 | 77 |
| | NDK | 71 | 97 | 96 | 79 | nd | 104 | 88 |
| EF | KEI | 2 | 75 | 46 | 1 | 40 | 78 | 96 |
| | IHL | 0 | 28 | 44 | 18 | nd | 115 | 130 |
| | LYQ | 13 | 67 | 50 | 15 | 65 | 61 | 81 |
| Interdomain residues: | LQN | 4 | 41 | 36 | 61 | 175 | 70 | 104 |
| | NLV | 0 | 82 | nd | 100 | 45 | 86 | 112 |
| | VIP | 21 | 92 | 80 | 95 | 117 | 78 | 77 |
| | PW | 73 | 89 | 102 | 84 | 94 | 92 | 87 |
| Domain 2 Loop | | | | | | | | |
| AB | LSE | 90 | 109 | 112 | 108 | 71 | 114 | 102 |
| | ESQ | 75 | 97 | 89 | 91 | nd | 84 | 95 |
| BC | RFL | 89 | 119 | 114 | 126 | 89 | 125 | 117 |
| | LNH | 88 | 80 | 90 | 89 | 105 | 85 | 97 |
| | HCL | 8 | 45 | 36 | 60 | 52 | 92 | 74 |
| | LEH | 0 | 45 | 43 | 54 | nd | 105 | 103 |
| FG | FNP | 28 | 96 | 110 | 61 | 67 | 80 | 73 |
| | PL | 86 | 112 | 110 | 106 | nd | 113 | 103 |
| | SAQ | 111 | 85 | 109 | 118 | 123 | 126 | 128 |

PE-conjugated goat anti-mouse Fc specific antibodies. The % of positive cells staining with the anti-gc chain mAb over an irrelevant control Ig is determined for a given gc chain mutant and for wildtype gc chain. A ratio of these values, converted to a %, is then calculated to express the relative ability of CP.B8 to bind to mutant vs. wild type gc chain. Data are adjusted for any differences in level of expression of a mutant vs. wildtype constructs by measuring the binding of a mAb specific for a 9 amino acid myc tag engineered at the 5' end of each gc chain construct. Values of 100% indicate no difference in the ability of the anti-gc chain mAb to recognize mutant vs. wildtype gc chain. Values reduced from 100% indicate amino acid mutations which affect mAb binding.

Mutants are selectively constructed based on the known structural features of the gc chain. See Gustchina et al., *Proteins: Structure, Function and Genetics* 21:140 (1995) and Bamborough et al., *Structure* 2:839–851 (1994)). Alanine substitutions are specifically introduced to scan the loop sequences (3 substitutions per mutant).

The effect of mutation on CP.B8 binding is indicated for mutants listed in Table 3. The data are expressed as a percentage reflecting the relative ability of CP.B8 to bind to a mutant gc chain as compared to its ability to bind the wild type sequence. The value "100%" indicates no effect of mutation and lower percentages indicate greater losses in binding as a result of the sequence change. Values of less

EXPERIMENT 7

Effect of CP.B8 on cytokine binding to high affinity cell surface receptors

The effect of the CP.B8 mAb on cytokine binding to the surface of 3 day PHA blasts also has been directly measured using I-$^{125}$ labelled IL-2 and I-$^{125}$ labelled IL-4. For the IL-2 assay, $2\times10^6$ PHA-blasts are incubated for 1 hour at 4 degrees C with or without increasing doses of anti-gc chain mAb in RPMI media. I-$^{125}$ labelled IL-2 is then added at a final concentration of 10 pM, the Kd for the high affinity IL-2 receptor. After 3 hours at 4 degrees, the cells are washed twice and I-$^{125}$ labelled IL-2 bound is quantified with a gamma counter. For the IL-4 assay, $2\times10^6$ PHA-blasts are incubated for 30 minutes at room temperature, with or without increasing doses of anti-gc chain 'nAb in PBS. I-$^{125}$ labelled IL-4 is then added at a final concentration of 80 pM, the Kd for the high affinity IL-4 receptor (encompassing gc chain and IL-4-specific receptor chain). After 30 minutes at room temperature, the cells are washed twice and I-$^{125}$ labelled IL-4 bound is quantified. CP.B8 blocks both IL-2 and IL-4 binding to PHA-blasts over the 1–100 ug/ml mAb dose range, achieving 50% and 27% inhibition of cytokine binding to the high affinity cellular receptors for IL-2 and IL-4, respectively. These data correlate with the inhibitory effect of CP.B8 on IL-2 and IL-4 induced biological activity.

The other anti-gc chain mAbs, including activities represented by CQ.C11, AF.F4 and AE.C9, bind to an epitope distinct from CP.B8 based on the crossblocking studies (see above). These mAbs may act by distinct mechanisms. However, each represents an activity which meets the criteria for a "gc chain blocking agent", being able to significantly inhibit the cell response to cytokine according to the present invention.

EXAMPLE 8

Figure 17:
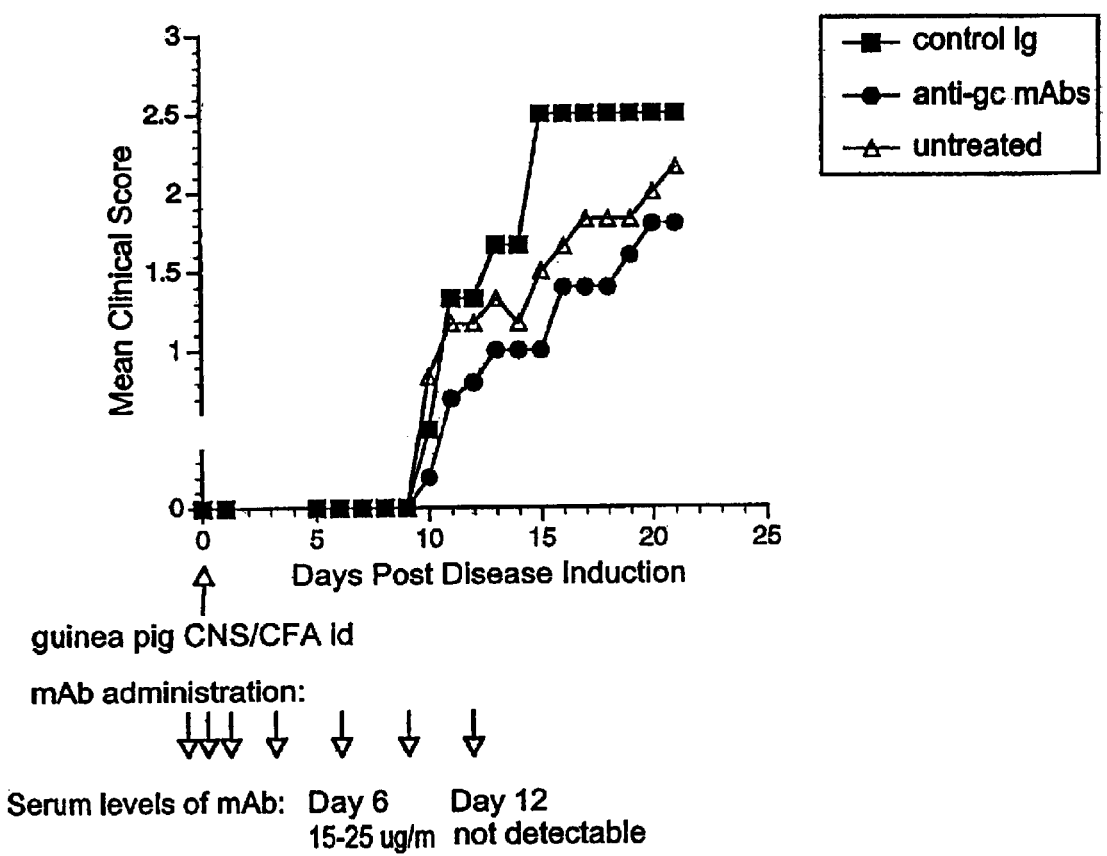
FIG. 17 is a graph plotting the mean clinical score in a guinea pig model of actively induced progressive EAE versus time as a function different mAbs as follows: filled squares are clinical results with a control Ig; filled circles are results with anti-gc mAbs and open triangles are scores for untreated animals.

Inhibitory Effect on the Induction of Disease in an Animal Model of Multiple Sclerosis The ability of anti-human gc chain mAbs to inhibit the induction of EAE was tested in a guinea pig model system of human multiple sclerosis. Mouse anti-gc chain mAbs raised against human gc chain were employed in this system based upon their crossreactivity with guinea pig gc chain. This crossreactivity was established by mAb binding to guinea pig lymphocytes as measured by immunofluorescent staining and by mAb mediated inhibition of antigen-specific guinea pig T cell proliferation in vitro. EAE was induced in female Hartley guinea pigs as previously described by Kent et. al. (*J. Neuroimmunol.* 58:1–10 (1995) by intradermal injection of 0.2 ml homogenized CNS tissue emulsified in Complete Freund's Adjuvant at the base of the neck. Clinical signs of disease are routinely induced by day 9–10 using this regimen. Groups of six animals randomly assigned into treatment groups received either PBS, mouse control Ig, or mouse anti-gc chain mAbs (a combination of the CP.B8 and CQ.C11 mAbs) beginning prior to disease induction and continuing periodically through day 12 post induction, i.e. day -1, 0, 1, 3, 6, 9, and 12. Animals were dosed at each time point with 5 mg/kg of control Ig or mAbs specific for gc chain. Administration of anti-gc chain mAbs both reduced the mean clinical score and delayed clinical disease as compared to disease onset and severity in the control Ig treated group (See FIG. 17).

Although the foregoing invention has been described in some detail by way of illustration and example for purposes of clarity of understanding, it will be obvious to one skilled in the art that certain changes and modifications may be practiced within the scope of the invention, as limited only by the scope of the appended claims.

What is claimed is:

1. A pharmaceutical composition which comprises an effective amount of a gamma common chain blocking agent wherein the agent is a monoclonal antibody selected from the group consisting of:

(a) a monoclonal antibody that cross competes with monoclonal antibody CP.B8 produced by hybridoma cell line ATCC No. HB-12107 for binding to gc chain, and also cross competes with Fab, F(ab')$_2$, and Fv fragments and conjugates of said CP.B8;

(b) a monoclonal antibody that cross competes with monoclonal antibody CQ.C11 produced by hybridoma cell line ATCC No. HB-12105 for binding to gc chain, and also cross competes with Fab, F(ab')$_2$, and Fv fragments and conjugates of said CQ.C11;

(c) a monoclonal antibody that cross competes with monoclonal antibody AF.F4 produced by hybridoma cell line ATCC No. HB-12104 for binding to gc chain, and cross competes Fab, F(ab')$_2$, and Fv fragments and conjugates of said AF.F4; and (d) a monoclonal antibody that cross competes with the monoclonal antibody AE.C9 produced by hybridoma cell line ATCC No. HB-12106 for binding to gc chain, and cross competes with Fab. F(ab')$_2$, and Fv fragments and conjugates of said AE.C9.

* * * * *